(12) United States Patent
Bairamijamal

(10) Patent No.: US 11,512,402 B2
(45) Date of Patent: Nov. 29, 2022

(54) HIGH PRESSURE PROCESS FOR $CO_2$ CAPTURE, UTILIZATION FOR HEAT RECOVERY, POWER CYCLE, SUPER-EFFICIENT HYDROGEN BASED FOSSIL POWER GENERATION AND CONVERSION OF LIQUID $CO_2$ WITH WATER TO SYNGAS AND OXYGEN

(71) Applicant: Faramarz Bairamijamal, Germantown, MD (US)

(72) Inventor: Faramarz Bairamijamal, Germantown, MD (US)

( * ) Notice: Subject to any disclaimer, the term of this patent is extended or adjusted under 35 U.S.C. 154(b) by 1392 days.

(21) Appl. No.: 14/392,066

(22) PCT Filed: Feb. 19, 2014

(86) PCT No.: PCT/EP2014/000443
§ 371 (c)(1),
(2) Date: Aug. 5, 2015

(87) PCT Pub. No.: WO2014/127913
PCT Pub. Date: Aug. 28, 2014

(65) Prior Publication Data
US 2015/0376801 A1    Dec. 31, 2015

Related U.S. Application Data

(60) Provisional application No. 61/850,685, filed on Feb. 21, 2013.

(51) Int. Cl.
*C25B 9/00*    (2021.01)
*C25B 9/23*    (2021.01)
(Continued)

(52) U.S. Cl.
CPC .............. *C25B 9/23* (2021.01); *B01D 53/002* (2013.01); *C01B 3/12* (2013.01); *C01C 1/04* (2013.01);
(Continued)

(58) Field of Classification Search
CPC .. C25B 9/00; C25B 9/06; C25B 15/00; C25B 15/02
See application file for complete search history.

(56) References Cited

FOREIGN PATENT DOCUMENTS

WO    WO2006097703    *    9/2006    ............... C01B 3/38

* cited by examiner

*Primary Examiner* — Zulmariam Mendez

(57) ABSTRACT

The present invention relates to a high pressure process for Pre-Combustion and Post-Combustion $CO_2$ capture (HP/MP/LP gasification) from a $CO_2$ gas stream (CO2-Stream) by way of $CO_2$ total subcritical condensation (CO2-CC), separation of liquid $CO_2$, higher pressure elevation of obtained liquid $CO_2$ via HP pump, superheating of $CO_2$ up to high temperature for driving of a set of $CO_2$ expander turbines for additional power generation (CO2-PG), EOR or sequestration (First new Thermodynamic Cycle). The obtained liquid $CO_2$ above, will be pressurized at a higher pressure and blended with HP water obtaining high concentrated electrolyte, that is fed into HP low temperature electrochemical reactor (HPLTE-Syngas Generator) wherefrom the cathodic syngas and anodic oxygen will be performed. In particular the generated HP oxygen/syngas will be utilized for sequential combustion ("$H_2/O_2$-torches") for super-efficient hydrogen based fossil power generation (Second new Thermodynamic Cycle).

59 Claims, 12 Drawing Sheets

(51) Int. Cl.
  *B01D 53/00*    (2006.01)
  *F22B 1/00*     (2006.01)
  *F01K 7/22*     (2006.01)
  *F01K 25/10*    (2006.01)
  *F01K 13/00*    (2006.01)
  *C25B 1/04*     (2021.01)
  *C25B 9/05*     (2021.01)
  *C25B 9/19*     (2021.01)
  *C25B 9/73*     (2021.01)
  *C01B 3/12*     (2006.01)
  *C01C 1/04*     (2006.01)
  *C05C 1/00*     (2006.01)
  *C07C 29/151*   (2006.01)
  *C07C 41/01*    (2006.01)
  *C10G 2/00*     (2006.01)
  *C10L 1/04*     (2006.01)
  *C10L 3/08*     (2006.01)
  *C25B 1/00*     (2021.01)
  *F02C 3/04*     (2006.01)
  *F02C 3/20*     (2006.01)

(52) U.S. Cl.
  CPC ............ *C05C 1/00* (2013.01); *C07C 29/1518* (2013.01); *C07C 41/01* (2013.01); *C10G 2/30* (2013.01); *C10L 1/04* (2013.01); *C10L 3/08* (2013.01); *C25B 1/00* (2013.01); *C25B 1/04* (2013.01); *C25B 9/05* (2021.01); *C25B 9/19* (2021.01); *C25B 9/73* (2021.01); *F01K 7/22* (2013.01); *F01K 13/00* (2013.01); *F01K 25/103* (2013.01); *F02C 3/04* (2013.01); *F02C 3/20* (2013.01); *F22B 1/003* (2013.01); *B01D 2256/22* (2013.01); *B01D 2257/504* (2013.01); *B01D 2258/025* (2013.01); *B01D 2258/0233* (2013.01); *B01D 2258/0283* (2013.01); *B01D 2259/65* (2013.01); *C01B 2203/0283* (2013.01); *C10L 2200/0492* (2013.01); *C10L 2290/38* (2013.01); *C10L 2290/42* (2013.01); *F23J 2900/15061* (2013.01); *Y02C 20/40* (2020.08); *Y02E 20/16* (2013.01); *Y02E 20/32* (2013.01); *Y02E 50/10* (2013.01); *Y02E 50/30* (2013.01); *Y02E 60/36* (2013.01); *Y02P 20/10* (2015.11); *Y02P 20/129* (2015.11); *Y02P 20/151* (2015.11); *Y02P 20/50* (2015.11)

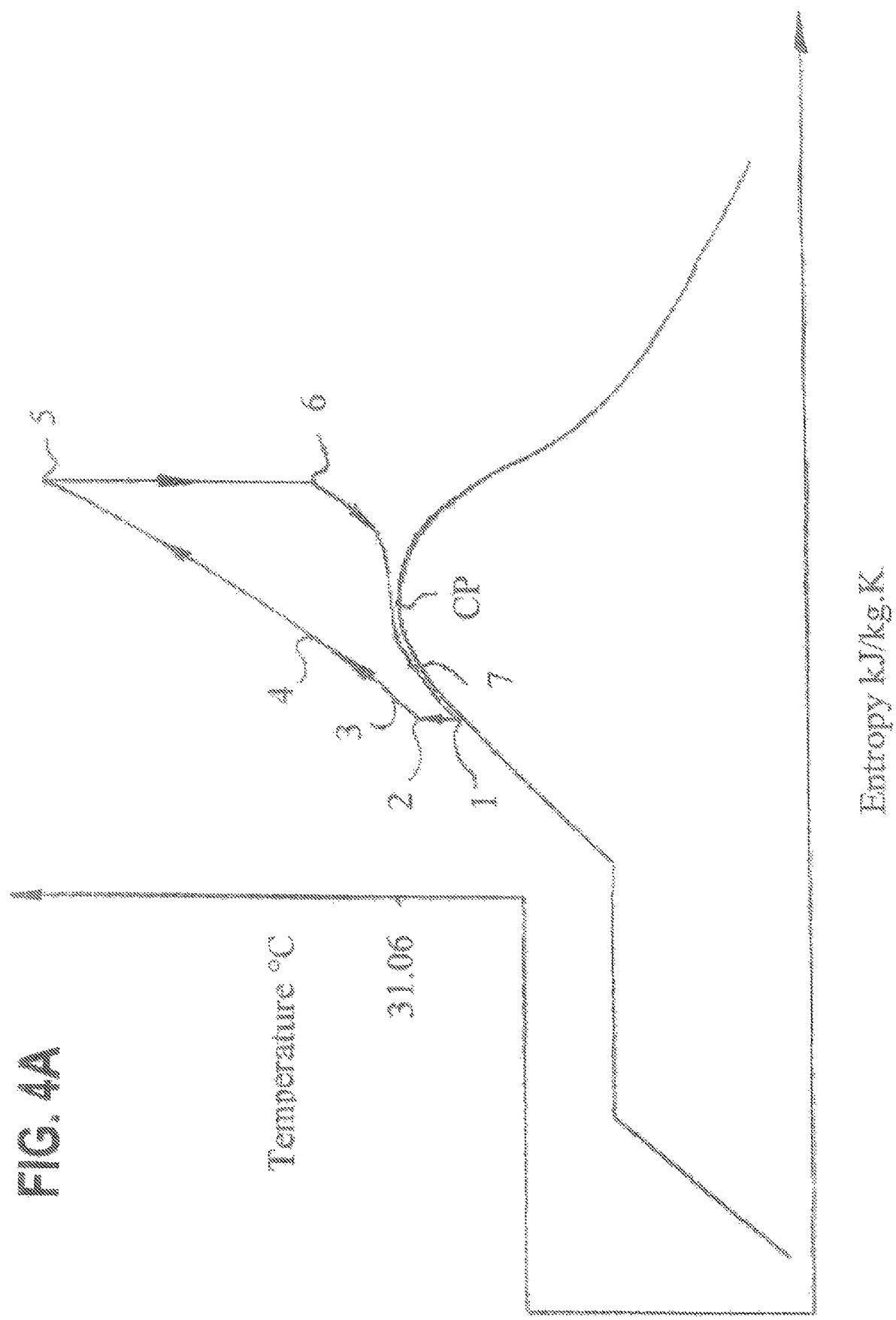

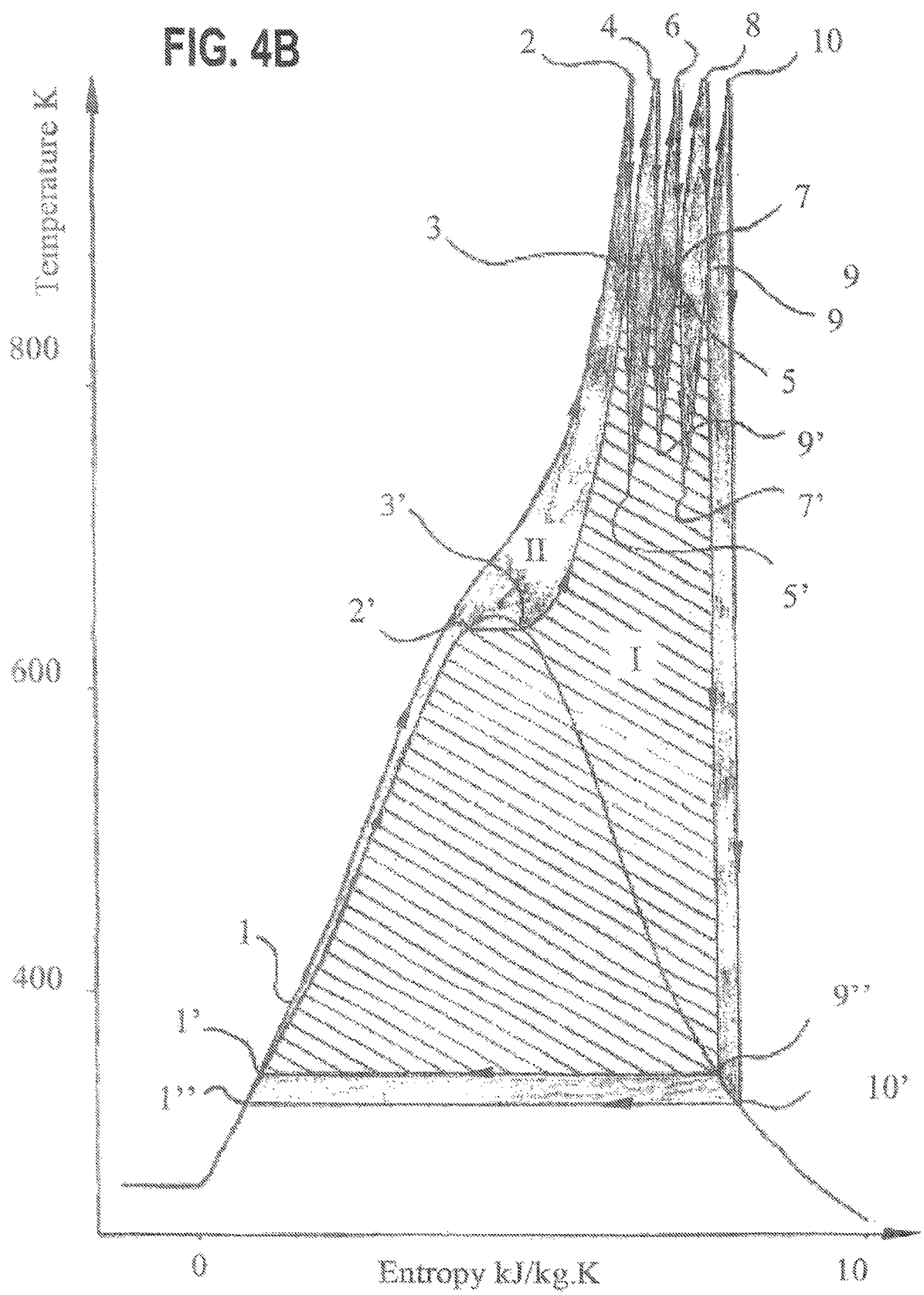

HIGH PRESSURE PROCESS FOR CO$_2$ CAPTURE, UTILIZATION FOR HEAT RECOVERY, POWER CYCLE, SUPER-EFFICIENT HYDROGEN BASED FOSSIL POWER GENERATION AND CONVERSION OF LIQUID CO$_2$ WITH WATER TO SYNGAS AND OXYGEN

CROSS-REFERENCE TO RELATED APPLICATION

This application is a continuation of application referring to the U.S. Provisional Application with the U.S. Ser. No. 14/392,066 with the priority date of Feb. 21, 2013, then filed for the PCT application of Feb. 19, 2014 with the PCT/EP2014/000443 and WO 2014/127913 A3.

The US national phase was filed Aug. 5, 2015 with U.S. Ser. No. 14/392,066 and the publication date of Dec. 3, 2015 under US 2015/0376801 A1. The most recent amendments were made in correspondence with USPTO Office on Jul. 19, 2018.

STATEMENT REGARDING FEDERALLY SPONSORED RESEARCH OR DEVELOPMENT

Not applicable

OTHER PARTIES INVOLVED TO A JOINT RESEARCH AGREEMENT

Not applicable, No other parties involved.

THE OFFICE ELECTRONIC FILING SYSTEM OF USPTO FOR THE PRESENT APPLICATION IN PRIOR

Not applicable

STATEMENT REGARDING PRIOR DISCLOSURES BY THE INVENTOR

PCT note of May 9, 2014

FIELD OF THE INVENTION

Process invention, Art Unit 1794

DESCRIPTION OF THE RELATED PRIOR ART UNDER 37 CFR 1.97 AND 1.98

Not applicable

THE SUMMARY OF THE INVENTION

The field of the present invention relates to a net-zero-carbon-emission process for the capture of carbon dioxide (as the major cause to the global warming) as well as generation of additional electricity by the conversion of the captured carbon dioxide as a new fossil energy resource via the high pressure low temperature electrochemical reaction to oxygen and syngas that can be further processed to high value products i.e. jet fuel, gasoline, methanol, dimethyl ether, ethanol, ammonia, urea, whereas the currently wasted thermal energy is reclaimed in this process for the carbon capture, conversion of carbon dioxide and generation of additional power.

The present process performs a processing for net-zero-carbon-emission super-efficient hydrogen based fossil power plants with high gross efficiency.

BRIEF DESCRIPTION OF THE SEVERAL VIEWS OF THE DRAWINGS

The related views to the drawings are presented in the Appendices A, B, C and D as follows:
Appendix A Description of the two new thermodynamic cycles with the associated thermodynamic charts presented in the FIGS. 4A, 4B, 5A, and 5B
Appendix B Description of the major embodiments via FIGS. 1 to 5
Appendix C Further elaboration for the general inventive concept of the present invention with it's three fundamental features (I), (II) and (III) that addresses the solution to the Stationary Sources of CO$_2$ emission in five principal embodiments according to the FIGS. 6 to 10
Appendix D: List of the abbreviations, acronyms, special expressions, and elements in the embodiments according to the FIGS. 1 to 10

BACKGROUND AND THE DETAILED DESCRIPTION OF THE RELATED ART

Figure 1:
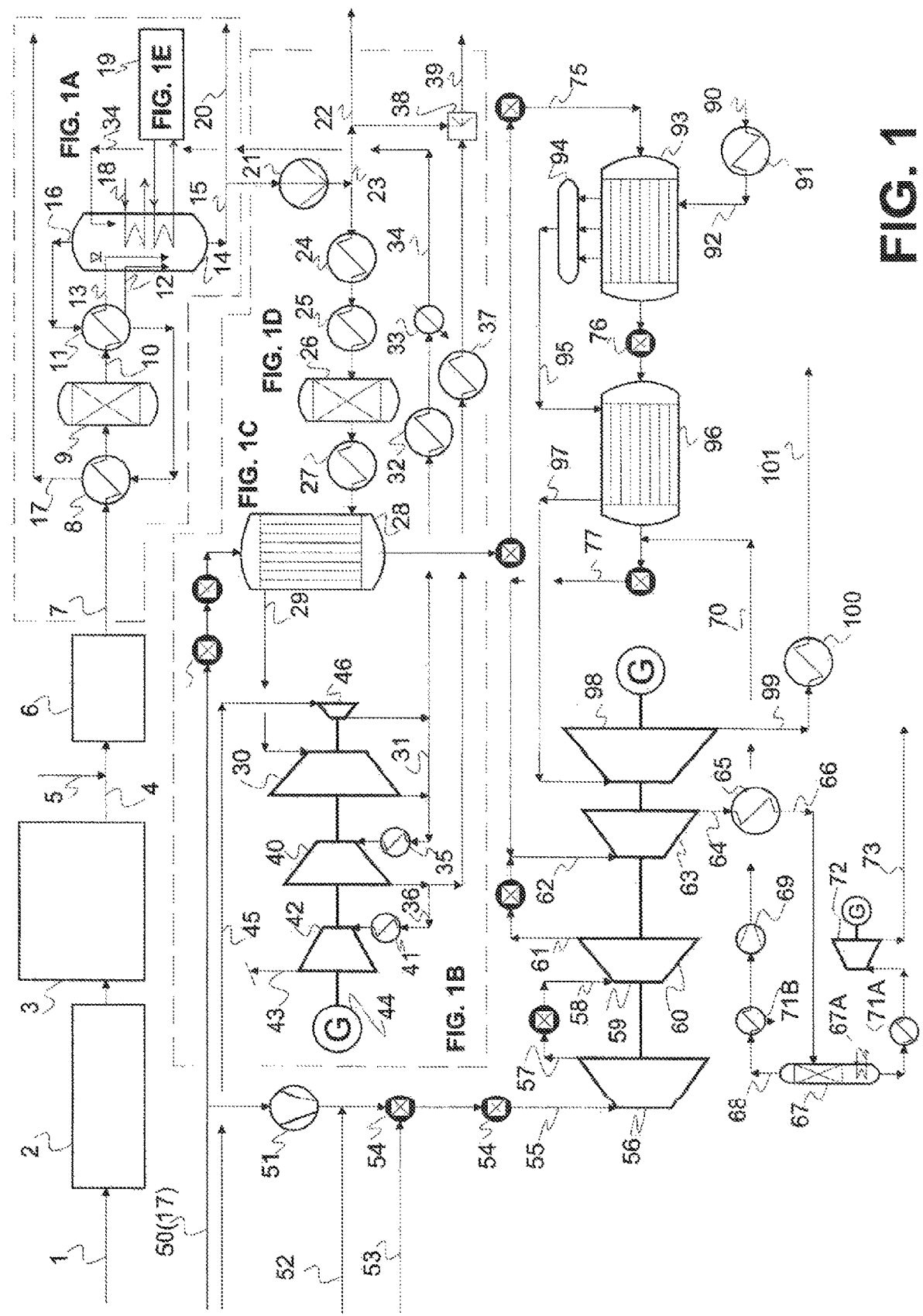

As result of increasing world population, the demand for electricity, transportation fuel and the commodity chemicals is increasing rapidly. Simultaneously, the world is encountered with threatening global warming due the emission of carbon dioxide that stems mostly out of the combustion of fossil resources for generation of electricity or conversion of fossil material into chemicals (e.g. transportation fuel, methanol, ethanol, ammonia, etc.). In addition, the higher demand of energy requires more extraction of crude oil and natural gas, while the use of coal is still troublesome or at least limited to some degree, particularly due higher CO$_2$ emission and other environmental impacts compared with natural gas. The latter fact has led part of coal power plants in United States to a change of fuel towards natural gas resulting to less CO$_2$ emission. Unfortunately, the intended measures for global reduction of CO$_2$ are mostly demised or at least lagging far behind. Other political consequences like CO$_2$ taxes are currently under discussion in some Western countries, that works at the expense of higher costs for generation of electricity an/or chemicals ultimately. The latter impact results inevitable to a misbalance in competitiveness. The increase of expenses due the separation of carbon dioxide via state-of-the-art technologies (both for pre-combustion as well as post-combustion carbon capture) and its further re-compression prior to a national pipeline (if ever ready) and sequestration, provides grave concerns in addition.

As result of these features, the Clean Energy, specifically Clean Coal developments are stalemated in recent years. Other alternatives like sustainable energy by use of biomaterial or waste-to-energy processes are by far unable to address the huge demand of energy, thus they are of marginal significance. Despite broaden outlook of gasification technologies in many perspectives-particularly the coal gasification—the extent of carbon emission and the GHG had also put the gasification process in a cul-de-sac, thus recently even some nuclear power plants are set under construction while some other are planned, as though the primary objectives of Clean Coal and the Clean Energy would be not achievable (e.g. in concord to United States Energy Independence and Security Act of 2007).

FIELD OF THE INVENTION

At the other hand the reuse of carbon dioxide as a new fossil energy resource that will reduce the GHG and the demand of primary fossil energy is also restrained due technically and economically unfeasible outcome at the present time. For instance the biological or bacteriological conversion of $CO_2$ to ethanol doesn't provide substantiated alternative due the low process yield. Respectively the commercial installation of those plants at large scale would not provide a viable way either.

The electrochemical conversion of aqueous solution of $CO_2$ was more and less subject of scientific investigation at atmospheric pressure and ambient temperature, though under the very low solubility of $CO_2$ (George Olah et al in reference [1]). A high concentrated aqueous solution requires high pressure $CO_2$ compression, absorption and cooling, that would lead to a technical-economical unreasonable scale either. The electrochemical conversion of $CO_2$ and steam under gaseous state was also investigated, without great economical aspect, however. The conversion of gaseous $CO_2$/water stream eases slightly the processing, while the required high yield of conversion at technical scale can not be met according to the mass of $CO_2$ emission (C. R. Graves et al in reference [2]). Both later electrochemical processes require a DC current that was suggested to be supplied by an external power plant; even an adjacent nuclear power plant was suggested.

The current need for a techno-economical feasible $CO_2$ capture process that resolves the GHG by significant reduction and performs the reuse of $CO_2$ in a responsive extent under simultaneously preserving the primary fossil energy resources, had initiated the present process invention. Therefore, the present process is now capable to capture and convert the $CO_2$ in feasible way up to large scale plant (e.g. 1000 MW conventional coal power plant). The capture of all Stationary Sources of $CO_2$ emission according to the new process is comprised, both, for the post-combustion capture (i.e. flue gas of all kind of fossil power plants, oil & gas, gas treatment, chemical plants, geothermal, aluminum and steel manufacturing as well pulp and paper production) and the pre-combustion capture (i.e. HP/MP and LP gasification plants). At the present time, the Stationary Sources of $CO_2$ emission reaches out to about 75% of all $CO_2$ emission globally. Thus the present process invention meets all Clean Energy objectives of United States and many other countries; namely the following prime objectives are attained:
(a) Reduction of energy reliance of the U.S. on foreign resources, e.g. crude oil and natural gas
(b) Availing the abundant coal reserve for Clean Energy
(c) Viable solution for the global climate warming and control of GHG In addition, three other goals were accomplished in order to address other current challenges; i.e.:
(d) Ultra Clean Fossil Energy, this term is ascribed to the present process for chemical and power plants due to the providing of Zero Carbon Emission, along with elimination of other emissions that is attained by the deletion of the chimney. For instance, there are no longer pollution of Black Carbon, mercury, antimony, NOx, SOx, and the radioactive constituent from fossil energy resources into the atmosphere
(e) Introduction of new surmounting measures for facilitation of super-efficient power plants, whereas the cooling tower and chimney are removed from the scenery of power generation, which are primary culprit for loss of over 40% of the primary thermal input energy
(f) Thus the way of nuclear power generation can be abandoned by economical reasons now
(g) The attainment for capturing liquid $CO_2$ within economically inexpensive conditions, resulting in the reuse of carbon dioxide to high-end commodity products like jet fuel, gasoline, methanol, DME, ethanol, fertilizers, etc., that in turn maximizes the efficacious use of fossil energy by preserving the resources. Due this fact the sequestration of carbon dioxide is no longer considerable. The profitability of EOR or IOR application of $CO_2$ for depleted oil fields via this process shall be analyzed case by case.

The objectives (a) to (g) could be achieved a general inventive concept by the operation of three fundamental features (I), (II) and (Ill) that addresses the techno-economic solution to the Stationary Source of $CO_2$ emission, wherein:
(I) harnesses the currently wasted energy of power and commodity chemical plants to the atmosphere and integrate the waste heat for post-, and pre-combustion carbon capture through a $CO_2$ cycle, that is preferably distinguished by sub-critical preheating and superheating for driving of $CO_2$ turbine and by super-critical condensation of $CO_2$ that is inherently interlinked with high pressure oxygen and syngas obtained from high pressure low temperature electrochemical generation of syngas (HPLTE-SG) and oxygen from liquid anhydrous $CO_2$ and water as electrolyte of HPLTE-SG, wherein the economically feasible operation for obtaining liquid carbon dioxide is performed with the $CO_2$-cycle with its peculiarities for cooling and condensation CO2-CC, waste heat recovery and process heat utilization by CO2-HR, supply of the required power for driving compressors or turbine-generator of the process CO2-PG (that supplies the $CO_2$ capture and backs up the electrolysis after AC/DC converter), on demand by a $CO_2$ closed cooling circuit for waste heat recovery CO2 CCC-HR, which features the $CO_2$ cycle of this invention (referred to the first new thermodynamic cycle, FIGS. 1, 2, 4A) to obtain liquid anhydrous carbon dioxide, that
(II) is then blended and cooled with purified water for reuse of carbon dioxide as a fossil energy primary resource (FIG. 3, elements 11, 12, 13, 14) at high pressure and low temperature to an electrolyte that is fed to the high pressure low temperature electrochemical reactor HPLTE-SG for generation of anodic oxygen and cathodic syngas ($CO/2H_2$), which is inherently interwined for cooling and condensation media for the above $CO_2$-cycle (FIGS. 5A and 5B), while driving turbines for AC current, which backs up the process power and the electrolysis after AC/DC converter, wherein the operation of these two section enables the post—as well the pre-combustion carbon capture (FIGS. 6, 7, 8 and 9) at techno-economically feasible extent, more specifically the operation of these two features combined with the feature III, v.i. has led to the,
(III) super-efficient hydrogen based fossil power generation with an overall efficiency of 85% to 90% (depending on location of the site and season), which is attained by the operation of the new Second Thermodynamic Cycle, wherein the cathodic pure hydrogen, preferably the hydrogen from a high pressure gasification is combusted with anodic oxygen at various pressures via torches to generate HP/IP/LP Direct Steam for superheated steam or reheating of the steam from the IP and LP sections of the turbine (FIGS. 4B and 10) in a way, that the final steam downstream of the turbine can be regained as pure water while the cathodic chemically pure syngas in stoichiometric composition of $CO/2H_2$ can be delivered to an adjacent chemical plant for high-end valuable ammonia, methanol, ethanol, fertilizer, gasoline plant that increases the overall efficiency and profitability of the site, lower costs and price of electricity, gasoline, commodity chemicals, ergo shorter period for the return of investment.

The above three fundamental principals of the present invention has evolved to five group of inventive embodiments, which are outlined via the block diagrams in FIGS. 6 to 10 with the list of state-of-the-art as well as the new inventive sections enclosed, which are applicable specifically for (1)post-combustion, (2)pre-combustion and particularly in (3)super-efficient hydrogen based fossil power generation, wherein the reuse of carbon dioxide and Zero-$CO_2$ emission from the Stationary Sources of $CO_2$ emission achieved to address the global GHG. These five block diagrams shall serve as over view of the process with their interrelation to the above I, II and III fundamentals of the invention without limiting other inventive sections of each applications, vide Appendix C.

BRIEF SUMMARY OF THE INVENTION

The present invention relates to a high pressure process for Pre-Combustion and Post-Combustion $CO_2$ capture (HP/MP/LP gasification) from a $CO_2$ gas stream (CO2-Stream) by way of $CO_2$ total subcritical condensation (CO2-CC), separation of liquid $CO_2$, higher pressure elevation of obtained liquid $CO_2$ via HP pump, superheating of $CO_2$ up to high temperature for driving of a set of $CO_2$ expander turbines for additional power generation (CO2-PG), EOR or sequestration (First new Thermodynamic Cycle). The obtained liquid $CO_2$ above will be pressurized at a higher pressure and blended with HP water obtaining high concentrated electrolyte, which is then fed into HP low temperature electrochemical reactor (HPLTE-Syngas Generator) wherefrom the cathodic syngas and anodic oxygen will be performed. In particular, the generated HP oxygen/syngas will be utilized for sequential combustion ("$H_2/O_2$-torches") for super-efficient hydrogen-based fossil power generation (new Second Thermodynamic Cycle).

BRIEF DESCRIPTION OF THE DRAWINGS

Brief and detailed descriptions for the FIGURES are presented in the Appendix B, and for the Block Diagrams are presented in the Appendix C

DETAILED DESCRIPTION OF THE INVENTION

High pressure process for both Post-Combustion and Pre-Combustion $CO_2$ capture from a $CO_2$ gas stream and/or from any $CO_2$ containing gaseous process media (referred to CO2-Stream) by way of total and/or partial condensation of $CO_2$ to liquid carbon dioxide (CO2-CC: Carbon dioxide Capture and Condensation) is invented, whereby the condensation of subcritical $CO_2$ by trespassing the liquid-vapor two-phase zone and/or more preferably supercritical-subcritical condensation above the critical point is carried out under elevated pressure merely above the critical pressure and below the critical temperature of carbon dioxide:

$P*(CO_2)=1070$ psi$=73.835$ bar $T*(CO_2)=87.8°$ F.$=31.06°$ C.

According to the present process invention it is first imperative, to cool down the $CO_2$ containing gaseous media with the available cooling media e.g. internal process media, cooling water or ambient air (air cooler, hybrid cooler) close over the critical temperature, so the condensation in this first heat exchanger(s) can be suppressed (in the context of present process invention, referred to as Over Critical Gas Cooler). Up to the over critical gas cooling, the water constituent of $CO_2$ containing gaseous media can be removed by way of condensation of water. Further on, the dehydration of $CO_2$ containing gaseous process medium takes place i.e. silica gel, organic or inorganic absorbens, so dry dehydrated $CO_2$ containing process gas (for instance, syngas containing $CO_2/CO/H_2$) can be processed to the next subcritical heat exchanger(s), wherein a partial $CO_2$ condensation of upstream gaseous media will take place in countercurrent to the undercooled gases (e.g. $H_2/CO$) after the liquid $CO_2$ separation. The condensation of major part of $CO_2$ takes place in the Main Condenser and liquid $CO_2$ collector.

This process considers the condensation of $CO_2$ from any $CO_2$ containing sources (referred to CO2-Stream), in particular as of the flue gas of fossil power plants based on coal, biomass, municipal waste, crude oil, petcoke, refined oil intermediates, bulk solid or liquid carbonaceous waste fired power plants as well as natural gas or any offgas ($H_2/CO$ of steel manufacturing) fired in the combustion chamber of gas turbine in the single cycle or combined cycle power plants.

The present process encompasses also the condensation of $CO_2$ from any other CO2-Stream i.e. aluminum production, cement industry, steel manufacturing and coke preparation from coal, geothermal source, fermentation off gas, $CO_2$ constituent in the untreated natural gas off of the well, pulp and paper manufacturing and chemical plants i.e. ammonia, methanol, ethanol, gasoline production plant and air will be considered in this process. In addition, this process comprises also the capturing of $CO_2$ from $CO_2$ containing gases obtained either from high pressure syngas (i.e. from high pressure gasifier) directly and/or middle or low pressure syngas (obtained from MP/LP gasifiers) after pressure elevation by a compressor.

The term HP syngas in the sense of this process invention according to FIG. 1, is ascribed to a syngas which is generated by HP gasifier 1, so the syngas (after the passing gas clean up 2, syngas scrubber, syngas cooler, COS hydrolysis, syngas cooling, mercury removal, Acid Gas Removal unit for removal of $H_2S$, and injection of steam/water 5, to CO-Water Shift Converter 6, either for partial conversion and stochiometric adjustment of $H_2/CO$ ratio or total conversion of CO to hydrogen by adding of water/steam into the syngas) shall be obtained in upstream of the CO2-CC unit (process stream 7), and upstream of Over Critical Gas Cooler 8 by at least a pressure, slightly above the prevailing critical pressure of carbon dioxide, more preferably it is obtained in a margin of the partial pressure of $CO_2$ that is close above the critical pressure of the carbon dioxide.

The HP gasifier according to the meaning of present process invention is ascribed to any gasification process wherein the HP gasifier is fed with natural gas, crude oil, coal slurry, biomass, more advantageously fed with carbon rich bulk solid carbonaceous material preferably in powder or dust form, i.e. coal (both in low rank and/or high rank), petcoke, biomass are fed into gasifier via high pressure dry feeding system (e.g. Aerojet Rocketdyne (former PWR) Dry Pump or HP-Dry CCS, High Pressure Dry Continuous Coal Supply in pursuant to PCT/US2010/002482 or EP 09 012 157.5) takes place. The HP/MP/LP gasifier above can be fed either with air or in advanced gasifier with oxygen, preferably that is obtained hereby from the anode of HPLTE-Syngas Generator.

The term MP or LP syngas in the meaning of present process invention, is ascribed to a syngas pressure which is generated by MP or LP gasifier 1, 2, so the syngas after passage of gas clean up, syngas scrubber, syngas cooler, COS hydrolysis, syngas cooling, mercury removal, Acid Gas Removal unit for removal of $H_2S$, and CO-Water Shift Converter 6 (either partial conversion for adjustment of $CO/H_2$ ratio or total conversion of CO to hydrogen by adding of water/steam into the syngas, whereas the obtained syngas upstream of the CO2-CC unit will have lower pressure than the critical pressure of carbon dioxide. In this case, an interim compressor (FIG. 1, 3, upper comment) shall pressurize the MP/LP syngas to a higher pressure that is preferably slightly above the critical pressure of carbon dioxide required upstream of CO2-CC and Over Critical Gas Cooler. In the latter case, the intercoolers of interim syngas compressor are encompassed within the CO2-HR Unit that comprises Heat Recovery carried out by $CO_2$ as working process media (akin to HRSG section for water-steam system).

It is from process economics perspective more advantageous, that the present process invention can be applied to for $CO_2$ removal after a HP Gasification Island, so the operation pressure of the HP row syngas downstream of gasifier and upstream of CO2-CC section prevails above the critical pressure of $CO_2$. As described v.i. this kind of gasifier are utmost preeminent gasifiers that can be installed for high efficient syngas generation for chemicals and more specifically for super-efficient hydrogen based power plants.

The condensation of carbon dioxide by an operation pressure-advantageously merely above the critical pressure-requires cooling the gaseous media down below the 31° C. that can be performed with an Auxilliary Cooling Media or process media after $CO_2$ condensation (FIG. 1, 16, 17) i.e. by cooling water, refrigerant cooling (e.g. by use of Freon), ammonia absorber cooling, ambient air and/or a combination of them, specifically via dry air cooler in the winter season or in cold regions. In the summer season or in warm regions additional cooling circuit is necessary.

Figure 3:
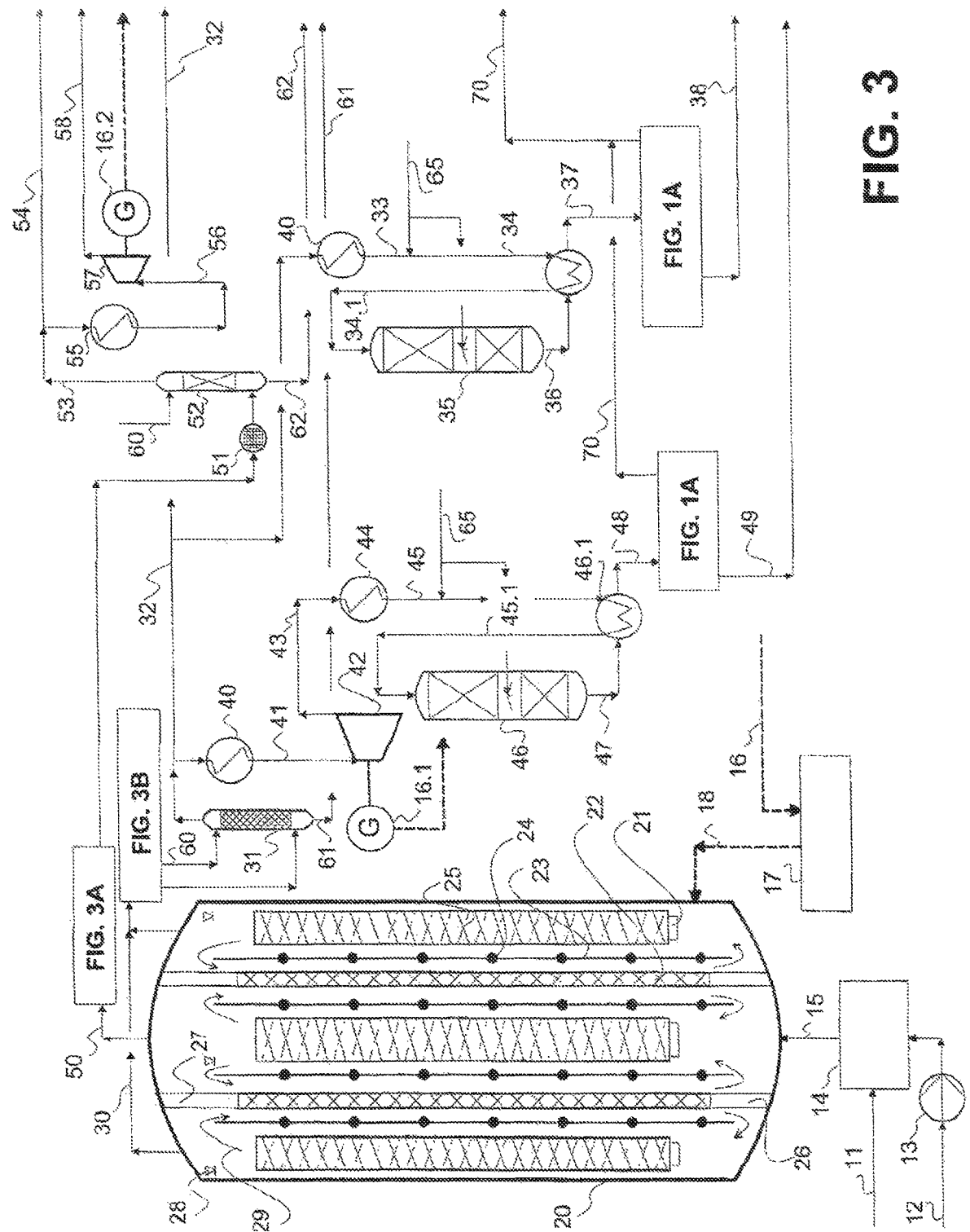

According to the present process, low temperature gaseous products of HPLTE-Syngas Generator v.i., that are cathodic $H_2/CO$ syngas and anodic $O_2$ with an average temperature of 10° to 25° C. will be involved as a process integrated cooling agent for $CO_2$ cooling and condensation as well (refer to HPLTE-Syngas Generator in FIG. 3 and the description vide infra). According to the FIG. 5 (exemplary for $O_2$ and CO, likewise for $H_2$ constituent of syngas as well), the cooling through each product stream of HPLTE-Syngas Generator can take place repeatedly for cooling of $CO_2$ either in CO2-CC section and/or for the $CO_2$ cooling and condensation in the $CO_2$ power cycle.

More preferably, the additional cooling circuit can be performed by an Auxiliary Cooling Unit (referred to as ACU) via expansion of part of the obtained liquid carbon dioxide to lower pressure level at one side of a heat exchanger, while at the other side the undercooling the carbon dioxide containing gaseous process media to the total condensation of $CO_2$ will be performed below the critical temperature of carbon dioxide in the Main Condenser. For instance, the expansion of approximately 16 lbs liquid carbon dioxide from 74 barg down to ca. 5.547 barg at −55° C. (triple point of $CO_2$ at −56.57° C.), enables the condensation of 84 lbs carbon dioxide out of the syngas mixture or any $CO_2$ containing gas. The residual traces of $CO_2$ in syngas (e.g. for ammonia process) can be removed by way of a Trim Absorber, so the $CO_2$ cleansed syngas can be forwarded to methanization reactor, prior to ammonia synthesis section.

The present process considers the release of part of the obtained liquid carbon dioxide in the margin from critical point of $CO_2$ down to the sublimation line (in the sense of temperature-entropy or pressure-enthalpy chart) that is over the sublimation line of carbon dioxide. The released $CO_2$ can be recompressed and recycled back to the upcoming $CO_2$ containing process upstream of CO2-CC. Preferably, the operation pressure of ACU is to be kept above the triple point temperature of $CO_2$ and the sublimation line of $CO_2$ at the coolant side in order to avoid the deposits of $CO_2$ solid sublimates.

The CO2-CC Unit consists specifically of Over Critical Gas Cooler(s) 8, final dehydration adsorber columns 9 (working intermittently for dehydration/regeneration mode of operation, dehydrated $CO_2$ stream 10), Subcritical Gas Cooler(s) 11, $CO_2$ Main Condenser(s) 14 and the ACU the Auxilliary Cooling Unit 19. The present CO2-CC can be inventively carried out in any region of $CO_2$ (in the sense of temperature-entropy chart or enthalpy-entropy chart of $CO_2$) i.e. subcritical condensation, condensation on critical point, particularly condensation of $CO_2$ in supercritical region with cooling systems based on low temperature gaseous products of HPLTE-Syngas Generator, which can be employed repeatedly (refer to FIG. 5 A, B exemplarily), air cooler, cooling tower, coolant system 18 (e.g. ammonia absorber coolant, Freon, refrigerating system), more preferably supported by ACU carried out by release and vaporization of part of liquid $CO_2$ process media.

In order to conduct the condensation of $CO_2$ with minimal thermal condensation energy, it is preeminent to cool first the gaseous media by supercritical gas cooler(s) close over the critical point ($CO_2$ condensate 12), then further cooling 13 by trespass the critical point down to subcritical region by subcritical gas cooler(s) and the Main Condenser, 14 with liquid $CO_2$ streams 20, and 15 (for semi-open cycle i.e. for EOR, IOR, Urea production). By this measure the minimal cooling performance will be required by the cooling agent or ACU in the summer season.

The $CO_2$ Main Condenser 14 captures also the gaseous recycle $CO_2$ stream that is directed from an interim section of the $CO_2$ back pressure turbine in the $CO_2$ power generation section (CO2-PG) or is recycled from ACU after re-compression of carbon dioxide stream.

On the grounds of carbon capture features of present process invention an utmost compact and cost efficient way for removal of $CO_2$ is fulfilled as regards to costs of investment, operation and maintenance costs—compared with Selexol, Rectisol and Benfield absorption and PSA for removal of $CO_2$ according to the state-of-the-art processes. This process encompasses the utilization of separated liquid $CO_2$ for heat recovery and additional power generation via $CO_2$ expander turbines.

The utilization of $CO_2$ is carried out by pressure elevation of liquid carbon dioxide by use of HP-Liquid $CO_2$ pump, typically in margin of 250 to 300 barg or higher pressure under steady operation of pump in $CO_2$ subcritical temperature, preferably in the margin of 10° to 25° C.

The pressure elevation via pump (either in a single or multiple pumping stages) is considered to be carried out with simultaneous indirect cooling of liquid $CO_2$ while pumping performed. The cooling of the liquid $CO_2$ centrifugal pump or reciprocating plunger pump or pump stages— such as like applied in some urea plants or for pressurization of anhydrous ammonia—comprises the employment of intercooler(s) and jacket cooling of the pump(s) as well.

The HP liquid $CO_2$ stream can preferably be processed in part for various other applications like urea manufacturing and/or after heat recovery (not depicted in FIG. 1) for HP $CO_2$ sequestration. It can be also availed for desuperheating of MP $CO_2$ stream for EOR (Enhanced Oil Recovery) or $CO_2$ MP-sequestration or delivering to national $CO_2$ pipe line.

One of peculiarities of present process invention is pertaining to availing of liquid carbon dioxide as feedstock for higher value intermediates, syngas and oxygen, through high pressure low temperature electrochemical conversion of liquid carbon dioxide and water (HPLTE-Syngas Generator). This technically and commercially viable way can be carried out now in large scale commercial plant that produces value added final products which are originally obtained from natural gas and crude oil as well. Hence this, the liquid carbon dioxide can be transported and shipped to another location and sites, where the generation of syngas can take place. This provides a tremendous remedy because the transportation and storage of liquid carbon dioxide is by far less complicated than the transportation of LNG (liquefied natural gas). Therefore, the present process considers the export of liquid carbon dioxide as an auspicious option for safe transportation of energy resources. More specifically, the present process invention comprises in one of the embodiments a HPLTE-Syngas Generator. The side stream for excess $CO_2$ is processed as HP-liquid $CO_2$ for sequential blending/cooling with purified water that will be fed into the HPLTE-Syngas Generator.

The heat recovery with HP liquefied $CO_2$ is first carried out at a pressure, typically in margin of 250 to 300 barg or higher pressure, while the vaporization of liquid $CO_2$ (also referred to as $CO_2$ regasification) takes place at the low temperature, as low as the critical temperature of $CO_2$ of 31° C.

$$T^*(CO_2)=87.8° \; F.=31.06° \; C.$$

This leads to some preeminent advantageous features that makes the liquid $CO_2$ predestined to use the entire waste heat and other heat resources that are typically wasted in chemical and fossil power plants (typically through the cooling tower, chimney or to the ambient air). The recovery of those heat sources are also extraordinary important for leveraging of gross thermal efficiency, respectively increase of electric output efficiency of a fossil or nuclear power plant and the chemical plants as well.

According to the present process the heat recovery via liquid carbon dioxide at elevated pressure comprises every kind of heat sources, wherever the potential for the heat source is equal or lower than the critical temperature of liquid carbon dioxide of 10° to 31° C., more advantageously above the critical temperature of $CO_2$ for heat recovery vs. gaseous carbon dioxide. Specifically, the following prime heat sources are involved in the present process invention:

(a) CO2-HR of residual LP steam downstream of steam backpressure turbine and/or any steam condensation turbine, either for power generation or as driving machine for other working machines i.e. compressors or pumps. The extent of the dissipated energy downstream of steam turbine imposes the utmost greatest loss of thermal energy in any power plants, both fossil and nuclear power plants. This heat is typically lost into the atmosphere by the huge cooling tower, that portrays the scenery of a thermal power plant, usually in extent of 45% and more for most coal fired power plants and even higher in case of nuclear power plants Depending on seasonal and the vacuum prevailing downstream of the steam condensation turbine, the temperature level at the waste heat side is in the margin of 120° to 130° C., in some plant with vacuum pumps down to 60° to 50° C.

(b) Other waste heat resources i.e. flue gas through the chimney of coal, biomass, oil, natural gas fired plants, stack of combined cycle gas turbine power plants, in particular the single cycle gas turbine power plants. Other wasted heats are i.e. intercoolers of compressor, expansion heat downstream of back pressure steam turbines, or other back pressure expander turbines for offgas.

(c) Waste heat recovery includes also the intercoolers of intermediate compressors employed in the site, i.e. syngas compressor of MP/LP gasifier, intercoolers of flue gas compressor (FIG. 2, 62 with Flue Gas compressions streams 65 and 66) of conventional fossil power plants (typically depicted in FIG. 2, B with both natural circulation of liquid CO2 60 and/or stimulated circulation of liquid $CO_2$ via pump 63), off gas compressor of gaseous effluent of vicinal or adjacent chemical plants (i.e. purge gas of ammonia, methanol plant, DNCG, CNCG of pulp and paper plant) and the natural gas compressor or other hydrocarbon compressors (e.g. propane, butane, ethanol, methanol containing hydro carbonic gaseous off gases). Whereby the HP evaporated $CO_2$ stream 61 leaves the evaporator 64 to superheater stage (likewise in FIG. 2 A with $CO_2$ streams 73, 76 with evaporator 71, 72 and superheater 75).

(d) The waste heat recovery in CO2-HR encompasses the heat recovery of intercoolers of ACU's $CO_2$ recompressor (principally depicted in FIG. 2, subsection B in a CCC Closed Cooling Circuit arrangement for heat recovery) and/or any other compressor involved in the overall processing namely i.e. Flue Gas, syngas, natural gas and the HP hydrogen compressor.

(e) Process waste heats in fossil power plants i.e. steam condensate reflux of power plants and ash cooler.

(f) The CO2-HR comprises the superheating upstream of $CO_2$ turbine i.e. by use of any process heat, specifically indirect process heat that is generated by way of natural gas gasification with the oxygen (preferably obtained at the anode of HPLTE-Syngas Generator), more preferably by way of high pressure gasification and/or re-superheating of regasified $CO_2$ downstream of each $CO_2$ expander turbine's section before entering of $CO_2$ to the next lower pressure section(s) of $CO_2$ expander turbine (FIG. 1, CO2-PG). More preferably, the re-superheating of carbon dioxide will be combined with the steam heat downstream of steam back pressure turbine.

(g) Process waste heats in chemical plants, i.e. heat sources downstream of low temperature exothermic reactors i.e. HT- or LT-water gas shift converter, absorption heats of thermal absorber towers (e.g. nitric acid tower), exothermic heat of solution by mixing of process media (v.i. liquid carbon dioxide and water mixture prior to HPLTE-Syngas Generator) as well as intermediate or final product cooler (i.e. ammonia-nitric acid neutralizer of ammonium nitrate fertilizer manufacturing).

(h) Waste heat of off gases, purge gases (i.e. from ammonia, methanol and ethanol synthesis) and flue gas of chemical plants (i.e. flue gas of steam reformer).

(i) Waste heat sources of auxiliary process media i.e. jacket cooling of reactors, in particular jacket cooling and screen cooling of the gasifier.

(j) The CO2-HR includes also the jacket cooling section(s) of the torch(s) implemented for Direct Steam generation and/or resuperheating in super-efficient hydrogen based power plants v.i., by way of $CO_2$ superheating and/or $CO_2$ supraheating as inherent part of CO2-HR (referred to as closed-end jacket cooling).

The above $CO_2$ heat recovery via HP liquid carbon dioxide under (a) to (f) includes the available heat sources for vaporization at 31° C. and superheating of carbon dioxide up to a margin of 150° to 200° C. Thus the captured carbon dioxide for heat recovery is primarily utilized for power generation as a driving agent for turbines. The present process commenced the supraheating (likewise in the meaning for ultra superheated steam) of carbon dioxide that is considered up to 800° C. and higher temperature. The supraheating of carbon dioxide is carried out via, (k) Integration of all ancillary heat sources and all process sensitive heat sources for supraheating of utilized liquid-gaseous carbon dioxide, specifically Hot Syngas Cooler, both, either integrated in the gasifier or downstream of the gasifier. All process sensible heats in chemical plants, i.e. cracking furnaces, nitric acid plant heat sources downstream of middle or high temperature exothermic reactors i.e. water gas shift converter, ammonia, methanol and ethanol synthesis section.

(l) Integration of $CO_2$ supraheater within the sections of combustion chamber and/or in the HRSG units of conventional fossil power plants, pulp and paper industry (i.e. black liquor recovery boiler, bark boiler) and chemical plants i.e. combustion chamber of primary steam reformer of methanol and ammonia plants.

(m) In particular, the CO2-HR of present process invention comprises the waste heat of nuclear power plants for regasification of $CO_2$ in CO2-CC, which is conventionally wasted by the cooling tower.

(n) This process includes also the use of indirect fired furnaces (similar to start-up furnace of ammonia and methanol plant) for supraheating of re-gasified carbon dioxide as well, (o) More specifically, the supraheating upstream of $CO_2$ turbine i.e. by use of any process heat, specifically indirect process heat that is generated by way of natural gas gasification with the oxygen (preferably obtained at the anode of HPLTE-Syngas Generator), more preferably by way of high pressure natural gas gasification over the critical pressure of $CO_2$ whereas a slag-free HP syngas is obtained from this heater that is then routed to the main syngas stream (downstream of gas clean-up section of Gasification Island).

(p) Specifically, the present process encompasses the supraheating of HP $CO_2$ re-gasified stream via combustion of $H_2/O_2$ stream within the context of super-efficient hydrogen based fossil power plants.

Within the compass of CO2-HR sections, both in superheating and supraheating sections, includes the injection of liquid carbon dioxide as a measure for temperature controlled optimization remedy for optimal heat recovery from various sources of heat in order to cover more heat resources under CO2-HR system.

The CO2-HR section includes the removal of dissolved carbon monoxide in the liquid carbon dioxide process media by way of thermal stripping of liquid carbon dioxide, adsorption of CO with molecular sieves, more preferably by a solid reactants i.e. magnetite according to the reaction (1) that is internally oxidized with a controlled flux of oxygen via reaction (2) with the activated iron (typically used as ammonia synthesis catalyst) or any other reducing agent that oxidizes the traces of carbon monoxide to carbon dioxide (FIG. 1, 26).

$$Fe_3O_4 + 4CO \rightarrow 3Fe + 4CO_2 \quad (1)$$

$$3Fe + 2O_2 \rightarrow Fe_3O_4 \quad (2)$$

In the present process, the removal of impurities, specifically dissolved carbon monoxide will take place, preferably downstream of $CO_2$ superheater(s) and upstream of $CO_2$ supraheater.

Figure 2:
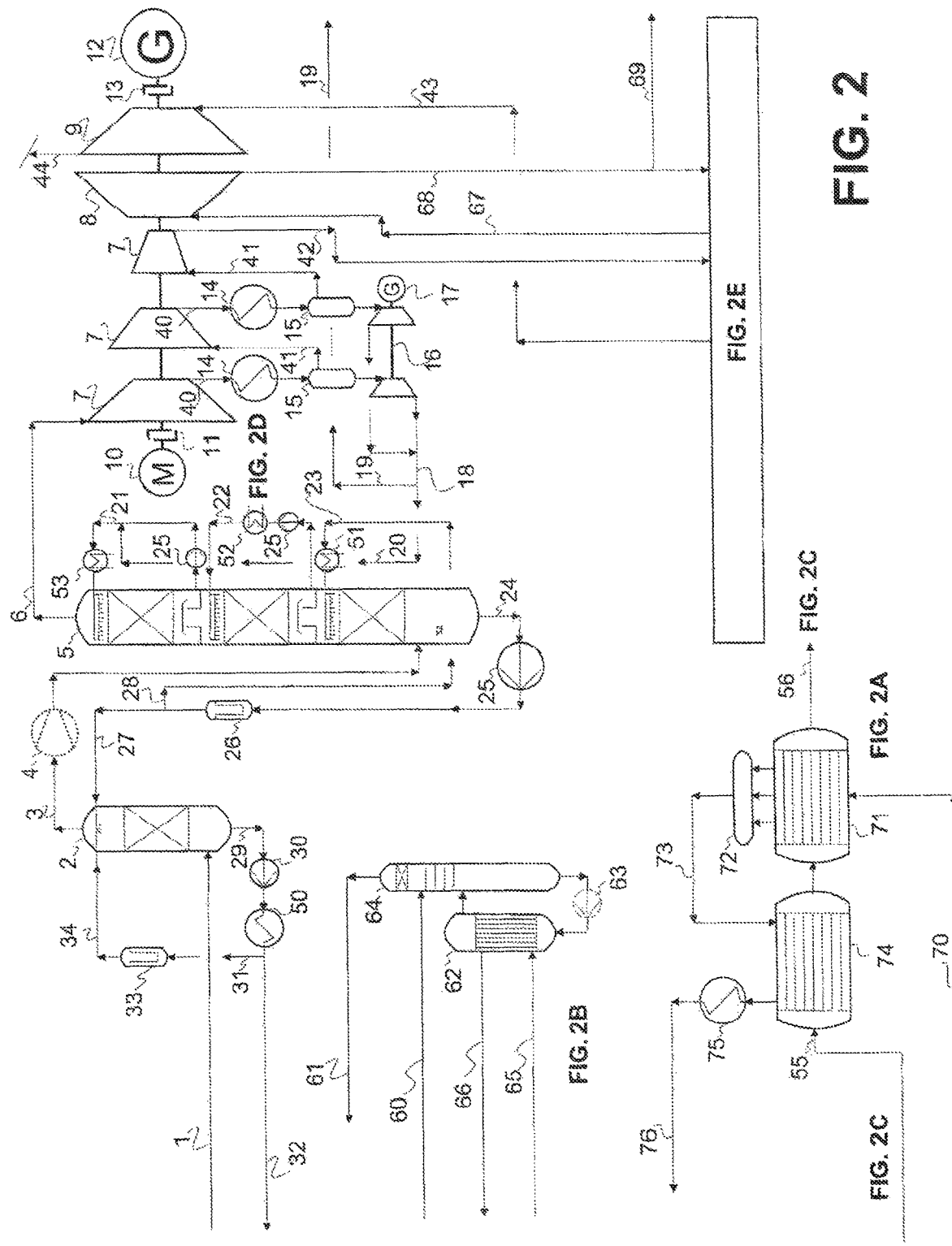

Similar like ACU, one and/or few number of centralized closed cooling circuit unit(s) is performed according to this process in order to accommodate the heat recovery from various internal resources into the captured carbon dioxide for vaporization of liquid $CO_2$ for the first stage and the second stage $CO_2$ superheaters (FIG. 2, section A). This measure is important from the following aspects:

(i) The CO2-HR can be easier centralized in the plant arrangement. Because the various waste heat sources can be dispersed in various places in the plant, the decentralized CO2-HR units would lead to a maze of piping and interdict process control system at high expense.

(ii) The working pressure of closed cooling circuit can be set for instance at 10 barg with water as heat carrier. Respectively, the operating pressure of one side of the HP heat exchangers can be set at lower working pressure that leads to less expensive equipment from design pressure point of view.

(iii) The mass flow rate of circulating closed cycle can be easier accommodated with the rate of the heats to be recovered from, (iv) the CO2-HR units can be set in a staggered arrangement according to the temperature level of waste heat sources and also in respect to process media with propensity to cause fouling in heat exchangers, which can be passed through the tubes of shell-tube heat exchangers preferably.

(v) The separation of various cooling process media (like cathodic $H_2/CO$ and anodic $O_2$ from HPLTE-Syngas Generator or steam downstream of condensation turbine) against each other is important from plant safety aspects. By use of closed cooling circuit the sources for heat recovery and/or sources for cooling media can be separated physically by shunting of CCC media that operates either under lower working pressure (for instance cathodic $H_2/CO$, anodic $O_2$, HP/MP/LP syngas from gasification plant island, MP/HP intercoolers of compressors) or at lower pressure, e.g. flue gas heat recovery, LP intercoolers of compressors. In this case, any upcoming leakage can be readily detected and allocated momentarily.

The present process for $CO_2$ utilization is further distinguished by regain of additional power generation through the utilized HP supraheated carbon dioxide. In addition, this process is capable to reduce the carbon emission down to Zero Emission Concept (by employing HPLTE-Syngas Generator v.i.).

It should be highlighted that in contrast to all actual state-of-the-art processes, the entire present process with CO2-CC, CO2-HR and use of CO2-PG for additional power generation and eventually sequestration, EOR, IOR will be profitable from economics aspects of view for the first time. The CO2-PG unit comprises typically multistage $CO_2$ back pressure expander turbines and a final turbine that works either in continuous operation or deigned for Peak operation. The first stage—the HP turbine section; is typically carried out with inlet temperature of 800° C. or higher, operating from 250 to 300 barg with a carbon dioxide to about 75 barg, merely above the critical pressure of carbon dioxide.

Since the condensation enthalpy of water is greater than the vaporization/superheating heat enthalpy of carbon dioxide the mass flow rate of two major cycles for power generation (water-steam Rankin cycle and the new First Thermodynamic Cycle with liquid & re-gasified $CO_2$) are to be accommodated from thermodynamic balances point of view. Hence that, the major part of recycling carbon dioxide will stem from HP section of $CO_2$ back pressure turbine. The recycle carbon dioxide after regenerative heat exchange and $CO_2$-HR (typically with a temperature of 45° to 40° C.) can be sent in part for MP $CO_2$ sequestration or EOR or delivered after re-liquification for $CO_2$ export according up to beverage grade.

The remaining recycle $CO_2$, or the entire recycle $CO_2$ (if no sequestration and EOR/IOR are considered) will pass through the cooling heat exchanger (air cooler, hybrid air cooler or water cooler in winter, with additional ACU for summer period or any combination of them) that provides the required cooling capacity for re-liquification of recycle carbon dioxide. The recycle LP $CO_2$ downstream of ACU and after the recompression of this side stream, merges the recycle $CO_2$ stream upstream of the $CO_2$-HR heat exchanger.

The second expander stage is distinguished by a MP $CO_2$ turbine that receives the $CO_2$ stream downstream of HP turbine section (either without re-superheating or with reheating of supraheated $CO_2$ stream) and expands the pressure down to MP export $CO_2$ for EOR/IOR or MP sequestration or delivering to national $CO_2$ pipeline. Finally, the LP $CO_2$ turbine is also considered in this process in case, part of the excess $CO_2$ shall embark for biological, bacteriological or chemical $CO_2$ conversion to higher value hydrocarbons, ethylene or other products and/or that part of excess $CO_2$ shall be released into the atmosphere for peak need of electricity or temporarily purposes.

Because the sequestration of carbon dioxide provides only a transitory solution for Green House Gases without any substantive contribution for reducing the loss of thermal energy, the present process invention comprises the chemical conversion of captured carbon as a new inexhaustible feedstock for production of products that are originally available by consumption of fossil energy resources. Hence this, a preservation of the primary fossil energy resources can be attained now.

Therefore, this process includes an electrochemical reductive conversion of liquid carbon dioxide as a precursor for manufacturing of high value commodity mother chemicals (i.e. ammonia, methanol, ethanol, DME dimethylether, propane, butane, etc.), special chemicals, automotive fuel and super-efficient hydrogen based fossil power generation which sustains the fossil energy resources. To some degree, the HPLTE-Syngas Generator is mimicking within fraction of second, what the natural process takes multiple ages for conversion of carbon dioxide to natural gas and crude oil naturally.

Further, the HPLTE-Syngas Generator is designed to perform high mass flow of syngas and oxygen, both required principally for large scale commercial co-generation plants for chemicals and power and/or power generation plants only.

The obtained HP liquid carbon dioxide from CO2-CC will be preferably pressurized by pumping to higher pressure level, blended with an organic electrolyte; more preferably purified water in a serial sequence of liquid carbon dioxide injection into water/water-$CO_2$ blend and cooling simultaneously, safely below the subcritical temperature in every sequence. The purified water fed to the present HPLTE-Syngas Generator comprises the conventional water cleaning, softening, reverse osmosis, ion exchange filters, mixed bed filter as well as biological and bacteriological purification. The pure water treatment encompasses also oxygen removal e.g. by catalytic hydrogenation of water, typically over Pd catalysts. The $CO_2$/water blend is fed into HPLTE-Syngas Generator obtaining gaseous cathodic $H_2$/CO and anodic oxygen products (FIG. 3).

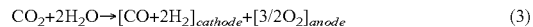

$$CO_2 + 2H_2O \rightarrow [CO + 2H_2]_{cathode} + [3/2 O_2]_{anode} \quad (3)$$

Each of the gaseous products will be directed to a pressure equalizing vessel individually also termed as gas buffer (not depicted in FIG. 3), before it will be passed further to an absorber.

According to present process, each product stream of HPLTE-Syngas Generator 30 and 50 undergoes first the dehydration i.e. via gas cooling and/or adsorption process with an adsorbens (e.g. Pillard Clay, molecular sieve, Silica Gel, etc.).

The cathodic $2H_2/CO$ is further accompanied with traces of oxygen and $CO_2$. The removal of these traces takes place (FIG. 3, 31) according to present device by way of molecular adsorption, absorption, chemisorption, non-catalytic chemical reaction in particular catalytic trickle reactor i.e. over Pd catalyst that is packed within the absorber column, converting the oxygen traces with the accompanied hydrogen to water. The absorber column absorbs the concomitant $CO_2$ with water 60 to 61 out of cathodic syngas stream 32.

$$O_2 + 2H_2 \rightarrow 2H_2O \quad (4)$$

The desorption of absorbed $CO_2$ in the discharged absorber water will be carried out either with flush pressure release or more advantageous via thermal stripping, preferably with electric heater operating as reboiler. The desorber stream (not depicted in FIG. 3) from cathodic gas absorber 31 shall combusted with oxygen and/or anodic gas desorber stream, generating heat for CO2-HR or preheating of the cathodic and anodic streams 62 upstream of each attributed back pressure expander turbine separately.

The anodic oxygen gas 50 contains traces of $H_2$/CO and $CO_2$ that are to be separated by way of molecular adsorption, absorption, chemisorption, non-catalytic chemical reaction or catalytic reaction i.e. over Pd catalyst. More preferably by way of chemical reaction over a plasma arc or an electric arc; EA (FIG. 3; 51) in a controlled manner that hydrogen will be converted with accompanied oxygen to water and CO to $CO_2$ before the absorption and immediate quenching of these trace products (obtained as water and carbon dioxide 62) can take place in the absorber column. The absorber column absorbs the concomitant $CO_2$ with water out of oxygen stream.

$$O_2 + 2H_2 \rightarrow 2H_2O \quad (4)$$

$$O_2 + 2CO \rightarrow 2CO_2 \quad (5)$$

Beside the gaseous cathodic and anodic products out of HPLTE-Syngas Generator, it is necessary to purge part of the water and/or water-carbon dioxide continuously from the liquid phase of each cathodic and anodic reaction chamber, in order to keep the required water analysis in the liquid phase. The purging of that water and/or water-carbon dioxide resembles the continuous purging of boiler water in HRSG section of conventional fossil power generation.

By virtue of the fact, that the extent of electrochemical energy-required for reductive conversion of carbon dioxide and water to $CO/2H_2$ and oxygen—is thermodynamically independent on the operation pressure of electrolysis, it makes possible, that the electrolysis can be working under high pressure without forfeiting any additional input of energy. That provides the pivotal advantage, that the electrolyt is fed via high pressure pump, while gaseous products are obtained from under high pressure and low temperature in turn. Hence that, the gaseous products can be preheated, superheated and released over an expander turbine—more preferably a set of back pressure expander turbines-, that drives a generator. The generated AC current of each generator converted to DC current backs up the electric energy for the electrolysis reaction.

Thus it is preeminent to drive the electrochemical reactor at high pressure and at subcritical low temperature as low as 10° to 25° C. as possible, in order to ensure the required DC electric energy needed from economic aspects. Therefore the HPLTE-Syngas Generator of the present process encompasses the preheating and superheating of entire and/or part of HP gaseous products (i.e. versus the CO2-HR, CO2-CC sections and that for condensation of $CO_2$ in the First Thermodynamic Cycle, FIG. 4, A along 6-7), driving at one side the back pressure expander turbines for generation of primary AC current (before the AC/DC converter), that backs up the electrochemical energy after AC/DC converter.

HP hydrogen can be prepared by way of HP water-shift converter from cathodic $2H_2/CO$ stream for HP application of hydrogen i.e. ammonia synthesis and HP Direct Steam generation. Complementary, HP oxygen (FIG. 3, 53, 54) is also considered for HP Direct Steam generation in super-efficient power plants (FIG. 1) and/or supply to HP gasifier.

The MP-$H_2$/CO and MP/LP-oxygen (FIG. 3, 56, 58) side streams are derived downstream of expander back pressure turbine for a variety of purposes, i.e. chemical products, gasoline fuels, oxygen supply to MP/LP gasifier, oxyfueling of upgraded existing conventional power plants, oxyfueling of existing power plants based on gas turbine and more advantageously MP direct and indirect steam generation for super-efficient power plants.

Since HPLTE-Syngas Generator provides affordable hydrogen and oxygen supply for small, middle and large scale commercial plants, oxyfueling and addition of hydrogen into the combustion processes are economically sound measures for improvement and retrofitting of existing plants.

For instance, MP/LP anodic oxygen obtained downstream of expander turbine of HPLTE-Syngas Gasifier provides the best opportunity for improvement and upgrading of existing conventional fossil power plants (e.g. coal, petcoke, biomass fired power plants as well as black liquor recovery boiler and bark boiler of pulp and paper manufacturing) and gas turbine power plant by way of oxyfuel processing.

In addition, the present process offers LP oxygen that can be easily added into the intake air duct of combustion chamber's blower, so oxygen enriched combustion air can be forwarded for firing while in turn, the nitrogen rich fresh air will be reduced in mass throughput. This LP oxyfueling for conventional fossil power plants performs two major advantages:

(a) The mass throughput of nitrogen passing through the process will be reduced as much as oxygen is added in to the combustion air. Respectively, the plant footprint provides reserve capacity that can be availed for additional coal feeding, which in turn, allows the increase of the plant capability leading to upgrading the plant performance, namely higher electric output.

(b) The expansion of HP preheated anodic oxygen down to repeatedly preheating to LP/atmospheric pressure (FIG. 5, A) prevailing in the air intake duct of those plants, delivers more AC/DC ancillary power that backs up the HP electrolysis of HPLTE-Syngas Generator (FIG. 3).

In the similar way the retrofitting of single cycle and/or combined cycle gas turbine power plants can be achieved. The MP anodic oxygen downstream of oxygen back pressure expander turbine can be added into the intake air of gas turbine power plants, leading to an increase of fuel capacity that delivers more electric output.

The oxyfueling of gas turbines can be readily carried out:

(c) By adding oxygen into the last air compressor's stage of gas turbine, so the mass flow rate of compressed air can be reduced, so the combustion turbine delivers more power for driving of the attached generator. This measure is applicable both for single shaft and multi-shaft gas turbine machinery as well.

(d) The additional oxygen can also be fed in to the combustion chamber of gas turbine directly, that results the same benefits mentioned above.

(e) Particularly, the oxyfueling of the processes itemized above (a), (b), (c) and (d) provides noticeable remedy for implementation of present process for total carbon capture, $CO_2$ utilization and power generation for retrofitting of existing power plants and chemical plants (described vide infra) due to reduction of nitrogen partial pressure in favor of leveraged $CO_2$ partial pressure for $CO_2$ removal according to this process.

The addition of MP/LP anodic oxygen above can be carried out with pure oxygen and/or a blend of oxygen with steam in any oxygen-steam ratio.

Thus this process performs three new ways for repowering of existing and/or incorporation in new single cycle or combined cycle plants through the $CO_2$ cycle with the First new Thermodynamic Cycle, oxyfueling and the new Second Thermodynamic Cycle with ultra-superheated Direct Steam generation.

This three measures above lead to an increase of the thermal performance of power plants and/or the chemical plants too (namely primary reformer of ammonia and methanol plants, natural gas fired furnaces for natural gas preheating of ammonia and methanol plants, furnace for molted salt heater, etc.).

MP cathodic hydrogen can be added either into the fuel gas supply of the gas turbine power plant and/or it can be directly injected into the combustion chamber of the gas turbine. In either case, the obtained steam in the combustion chamber mimics to some degree an augmentation akin to the augmentation of gas turbine with steam injection.

The other part of cathodic gaseous products can be kept under operation pressure of reactor for high pressure heat recovery, HP CO-water gas shift converter, whereby the $CO_2/H_2$ downstream of water gas shift converter, according to equation (6) v.i., can be directed to the CO2-CC section for carbon dioxide separation. Downstream of CO2-CC section for removal of carbon dioxide high pressure pure hydrogen is obtained ready for variety of applications for hydrogen based chemical production processes i.e. ammonia synthesis, hydrogenation of heavy oil, tar, oil sands, sand oil, heavy fraction, petroleum coke, and other organic residues compounds to higher value lighter hydrocarbons or for super-efficient hydrogen based fossil power generation.

In the latter case for the preparation of HP hydrogen, the entire captured re-liquefied carbon dioxide can be recycled back to the HPLTE-Syngas Generator.

$$CO + H_2O \rightarrow H_2 + CO_2 \qquad (6)$$

In another embodiment, like HP water gas shift converter, the middle pressure gaseous $CO_2/H_2$ conversion by way of water gas shift converter is also considered for middle pressure hydrogen supply after carbon dioxide removal via CO2-CC unit. Also in this case, the entire captured carbon dioxide can be recycled back to the HPLTE-Syngas Generator.

The anodic HP/MP oxygen can be delivered to gasifier, or fed to chemical processes; oxyfuel processes (oxyfuel applications i.e. for power generation in conventional fired power plants, gas turbine based power plants, black liquor recovery boiler) leading to high efficient chemical processes based on oxygen (i.e. nitric acid plants). More preferably the obtained HP oxygen will be applied for v.i. super-efficient hydrogen based fossil power generation.

Compared with the state-of-the-art oxygen preparation by way of cryogenic Air Separation, the present process provides a more cost efficient way for production of pure oxygen without employing any air compressor, towers, Cold Box, etc. Therefore the HPLTE-Syngas Generator is capable to supplant the commonly used processing of air separation for supplying of oxygen (LOX and GOX) by far.

According to present process, the prepared HP/MP cathodic syngas $2H_2/CO$ fits the stochiometric ratio for methanol synthesis section. Beside that, for each individual application of HP and MP $2H_2/CO$ stream, the $H_2/CO$ ratio can be easily adjusted through by-passing of a side stream of $2H_2/CO$ stream while the other part of stream will undergo the water gas shift conversion for manufacturing of other various mother chemicals, i.e. ethanol, SNG Synthetic Natural Gas (also referred to as Substituted Natural Gas), more specifically automotive fuel, cerosin, diesel and other chemicals.

With respect to the obtained syngas and oxygen from the liquid carbon dioxide and water, the present process invention performs an alternative and the utmost feasible way for manufacturing of high value final products (chemicals, fuel and power) which are presently available from natural gas and crude oil too. This process performs a solid solution for reduction of carbon dioxide emission from chemical and fossil power plants that is causative for global climate warming.

The present process invention for carbon capture, sequestration, utilization and power generation comprises the high pressure electrochemical conversion of $CO_2$ and water at low temperature into syngas and oxygen that is carried out inventory by HPLTE-Syngas Generator and the related devices, HP and/or MP water shift reactor, ancillary power generation via expander turbines, AC generator and the AC/DC converter (FIG. 3).

As the AC/DC converter, indicated in FIG. 3, element 17 backs up the HPLTE-SG by the DC supply line 18 primarily. Because the conversion of the AC from the generators to the needed DC for the HPLTE-SG is inevitably burdened by loss of power in the typical margin of 10%, the present process invention encompasses two other economically advantageous options, which can be embodied in the present process invention by the use of solar panel and fuel cell. As these two systems deliver DC current off the panel, the need for the conversion of AC to DC current via 17 can be reduced adequatably. The integration of supplemanray DC power gained via solar panels or generated via fuel cell—optionally with battery energy storage—backs up the HPLTE-SG supply line 18 (not depicted in FIG. 3), while greater portion of the generated AC current 16 from the generators can be dispached to the grid (FIG. 3, dashed line downstream of the generator, element 16.2). Thus thee integration of solar panel and/or fuel cell for supplementary DC supply leads to an additional increase of plant overall gross efficiency.

The integrated fuel cell panels can be fed by the anodic oxygen downstream of the last stage of the oxygen turbine at low pressure level, while the hydrogen supply can be performed after CO-water shift converters (1) from the LP section downstream of the last hydrogen turbine; or (2) from gasification process.

In yet another way, the electrolysis of any $CO_2$-water electrolyte more specifically in the HPLTE-SG can be backed up via use of thermoelectric generators that provides DC current without the loss of power through AC/DC Converter, wherein the thermal energy is converted to DC current.

The implementation of thermoelectric generator can be installed inventively in the sections for flue gas treatment, and Advanced Combustion (of the patent in continuation), CO2-HR and CO2-PG for heat recovery power generation associated with the first new thermodynamic cycle, specifically direct current generation via thermal energy conversion from the $CO_2$ cycle post the supercritical $CO_2$ turbine along the trajectory 6-7-1 of the FIG. 4. A alone or in combination with the heat exchangers for recuperator(s), $CO_2$ coolers and the $CO_2$ condensers.

Such thermoelectric generators can be also implemented for thermal energy conversion to DC current in the sections impinged with the CO2-Streams, i.e. the section for the flue gas compression and the CO2-CC section for $CO_2$ separation by cooling and condensation as well as heat recovery in the ACU of the present process.

In addition, these thermoelectric generator(s) can be implemented for the waste heat recovery to generate more back up DC power for the HPLTE-SG. The sources of these waste heat recovery are i.e. thermal conversion from the steam downstream of the steam turbine yet upstream of the cooling tower, from the flue gas at any $CO_2$ concentration prior, and/or during and/or post flue gas compressor v.s. and/or from any other CO2-Stream i.e. purge gas post the CO2-CC section.

Most importantly, the present process invention encompasses the processing for thermoelectric generators in connection with the syngas and oxygen obtained from the HPLTE-SG and deployed for the closing trajectory 6-7-1 of the first new thermodynamic cycle and/or in connection with the multi-stage syngas and oxygen turbines, i.e. specifically in the syngas and oxygen streams serving as condensing process media to obtain liquid carbon dioxide for further processing.

Equally important, the present process invention comprises the processing for thermoelectric generators in connection with the syngas and oxygen obtained from the HPLTE-SG and/or in connection with the multi-stage syngas and oxygen turbines, i.e. specifically in the syngas and oxygen re-superheating sections prior or more specifically downstream of each syngas/oxygen turbine's section as indicated in the FIGS. 5.A and 5.B. These thermoelectric generators can be installed upstream and/or downstream of the syngas-$CO_2$ condenser heat exchangers. These thermoelecyric generators can also be installed upstream and/or downstream of the oxygen-$CO_2$ condenser heat exchangers.

In the very same way, such thermoelectric generators can be installed according to the present process invention to carry out completely and/or in part the condensation of the steam downstream of the steam turbine of the second new thermodynamic cycle along the trajectory 10'-1" as presented in the FIG. 4.B.

The devise of such thermolelectric generators according to the present process invention for the supplementary DC back up power to CO2-water electrolyte at any operating pressure, most preferably for HPLTE-SG reactors are impinged with any process media of this process i.e. CO2 of the first new cycle at any pressure and temperature; and/or CO2-Stream at any concentration, pressure and temperature; syngas obtained from the HPLTE-SG at any CO/$H_2$ ration, pressure and temperature; oxygen obtained from the HPLTE-SG at any pressure and temperature; and/or any combination of the involved process media of the present process i.e. oxygen-enriched $CO_2$-containing purge gas post the CO2-CC section.

The reactor for HPLTE-Syngas Generator 20 is consisting of three main compartments (cathodic chamber, anodic chamber separated by the membrane 22 and the gas chamber to each electrode chamber that is separated from each electrode chamber by gas lock 27. The cathodic chamber, anodic chamber and the diaphragm sphere 22 in the third compartment, physically separated from the first two compartments. The compartments are placed in a concentric arrangement, whereby each anodic and cathodic chamber is equipped with separator cylinder 23, which embodies cooling coils 24, so the reaction can be carried out under isotherm condition.

The reactor is fed with water 12 and HP water-liquid $CO_2$ 11 either in two streams separately into each reaction chamber or with water-liquid $CO_2$ in one stream from the bottom. The liquid carbon dioxide is pressurized over the reaction pressure via a single stage and/or multistage pump(s), (FIG. 1, 21), while the purified water is pressurized by HP water pump 13. The two feed streams are blended by simultaneous mixing and cooling 14. More preferably, the liquid carbon dioxide is injected in number of injections into the water, blended and cooled i.e. via static mixer with integrated cooling coils in multiple numbers of stages. The cooling is carried out under subcritical temperature of carbon dioxide that no gas can be evolved while mixing. By these measures high concentrated aqueous solution of carbon dioxide in water 15 can be obtained ready for the electrolysis, in favor of high yield of gaseous products from the reactor and high mass throughput, that is specifically required for large scale commercial plants.

The electrochemical reactions are taking place in each reaction chamber under liquid-gas two phase flow regime that drives the liquid phase by principal of Mammoth Pump through the generated upwards flowing gas 29 that is evolved on the surface of each electrode. The reactor is further equipped with internal cooling coils in each compartment, preferably integrated within the cylindrical chamber separation plate 24 and/or along the recirculation space between the separation plate and diaphragm 22, in order to keep the reactor under isothermal reaction condition.

The product gas is separated from the circulating liquid phase at the topper section of reaction chamber below the liquid level 28 and extracted from the reactor 30, 50. The liquid phase will enter the diaphragm compartment from the top that is separated from the reaction chamber by concentric cylinder 23 with gas lock 27, so no gas can be entrained into the diaphragm compartment. The liquid phase flows downwards from each reaction chamber in co-current flow surrounding the diaphragm. At the lower section of diaphragm compartment the liquid phase recirculates in to the reaction chamber, joining with the make-up electrolyte. The migration of ions is carried out by passing through the porous diaphragm 22. Thus the diaphragm is embedded in the liquid phase and stands by impermeable support 26 solely and exposed to each circulating liquid phase flowing in co-current flow, so the migration of ions in the electrolyte through diaphragm is intensified from each side by intense mixing.

The HPLTE-Syngas Generator is distinguished also by special metal electrodes 25, made of electrically high conductive metal i.e. Pt, Au, Pd or other metals resistant chemically against acidic aqueous media and oxidizing oxygen on the anode as well as reducing hydrogen and carbon monoxide on the cathode. The electrodes are preferably consisting of a macro-porous matrix and/or a mesh of those metals (like Pt/Pd catalyst mesh in nitric acid manufacturing) that provides high surface area and macroscopic pores, so the evolved gaseous media can pass through quickly while the interface of liquid-electrode can be renewed momentarily. The electric contacts for electrode are performed by 21 on the electrode body. These features advance the rate of reaction in favor of gross efficiency of reactor and for high mass flow rate and low consumption of electricity that addresses the requirement for large scale plants.

Each high pressure gaseous product stream (30, 50) downstream of the reactor is conducted to a cushion gas buffer tank that equalizes the slightly pressure fluctuations caused by the reaction (schematically depicted in square figure). Downstream of each gas buffer tank, the gaseous products are subject to purification process v.s. outlined.

The purified syngas streams 32 will be either further processed for HP water shift converter 33, 34, 35, that converts the CO with water/steam 65 to additional hydrogen 36, 37, 38 and $CO_2$ 70 that can be removed by CO2-CC section depicted in FIG. 1 before the hydrogen 38 is processed further, namely for ammonia synthesis and/or super-efficient power generation or any other HP hydrogen application.

The present device invention encompasses the ancillary AC power generation 16.1, 16.2 to 16 via back pressure expander turbines 42, 57, each one driven by number of heat exchangers 40, 55, deigned as preheater for cathodic syngas and/or the anodic oxygen turbine and the AC/DC converter 17 that supplies the electrochemical direct current 18 required for the electrolysis.

The present process provides the sound technology for a new generation of hydrogen based super-efficient fossil power plants, which is designed to meet industrial requisitions for any plant size, in particular large scale commercial power plants with gross electric output performance of 1000 MW and higher.

In general, the present process for super-efficient power generation is consisting of various sections for heat recovery and five set of turbines for HP and MP ultra-superheated and/or superheated steam, HP/MP/LP-$CO_2$ turbines and an additional water turbine (e.g. Francis or Kaplan turbine for undercooled MP steam condensate) which are involved for export power and at least two set of expander turbines (multistage syngas 42 and oxygen turbines 57) for ancillary power back-up of HPLTE-Syngas Generator with the following cycles:

(a) HP generation of superheated, more preferably ultra-superheated Direct Steam and re-superheating sections from prepared hydrogen-oxygen in a semi-open cycle (c) MP superheated indirect steam from water-steam closed cycle (d) HP/MP/LP set of $CO_2$ turbines for supraheated $CO_2$ and/or re-superheated $CO_2$ stream via semi-closed liquid-gas-$CO_2$ cycle for EOR/IOR and/or closed cycle (FIG. 4, A)

(e) MP undercooled direct steam condensate turbine in a semi-closed cycle with partial recycle of water for HPLTE-Syngas Generator.

The five above cycles are driving the main turbines and generators for export power. In addition to those set of turbines, there are at two turbines employed for ancillary power generation. These are, at least one multistage expander turbine for each gaseous product of HPLTE-Syngas Generator, deigned for internal DC current power supply 18.

To (a) and (b):

The cycles (a) and (b) employ hydrogen that is either obtained downstream of CO2-CC (FIGS. 1; 17 and 50) or downstream of HP/MP/LP gasification process 52 or from HPLTE-Syngas Generator that is gained from CO constituent of syngas via water-gas shift converter 46, 35 (FIG. 3; 49/38). Other MP/LP hydrogen streams (i.e. from HPLTE-Syngas Generator streams and equipment 40, 41, 43, 44, 45, 43, to 47, 48 and finally to MP/LP hydrogen 49) and/or hydrogen from MP/LP Gasification Island FIG. 1; 50, can be compressed by 51 (in FIG. 1) to high pressure at a par with those other HP hydrogen streams 52 for HP Direct Steam generation.

The HP/MP hydrogen downstream of CO2-CC will be directed for HP/MP sequential combustion 54 with oxygen 53 via torches for 55 HP/MP Direct Steam (in FIG. 1) generation according to the equation (4) below. It is more advantageously to direct an oxygen side stream (either pure or blended with steam) into the main hydrogen stream through the torch 54.

$$O_2 + 2H_2 \rightarrow 2H_2O \qquad (4)$$

Both HP- and MP oxygen streams (in FIG. 1) for the Direct Steam generation are derived either directly downstream of HPLTE-Syngas Generator 50 and oxygen purification absorber 52 or after multistage oxygen back pressure turbine respectively (FIG. 3; 57, 58).

The semi-open cycle in (a) considers preferably HP back pressure turbines with re-superheating section (FIG. 1; along the streams 57 to 58 and 61 to 62 through the stages 56, 59, 60, 63, 98 of the turbine with LP steam 99, then pure water condensate 101), wherein the off steam 61 is joined with the 77 MP Direct Steam from MP $O_2/H_2$ combustion after heat recovery (for $CO_2$ supraheater 28, BFW 90, economizer 91 to preheated BFW 92, MP boiler 93 with demister 94 and MP steam super heater 96 v.i.; depicted in FIG. 1). Both MP Direct Steam streams (77 and 61 to 62) are conducted to MP back pressure steam turbine 63, whence the off steam 64 is condensed by CO2-HR section 65, obtaining steam condensate 66 that contains residual hydrogen 68 (further through $H_2$ compressor 69 to 70).

To (c):

The MP indirect steam, FIG. 1, 95, 97 is also generated by combustion of MP hydrogen 70, 75, 77 (from MP/LP gasification and/or MP hydrogen from HPLTE-Syngas Generator, FIG. 3; 49) with the MP oxygen (downstream of oxygen back pressure turbine) via separate water-steam closed cycle (c).

To (d):

The semi-closed cycle for HP-$CO_2$ liquid-gas (i.e. for EOR/IOR in FIG. 1, 20, and the temperature controlled 39 with liquid $CO_2$ 22 for desuperheating 38) according to (d) is consisting of liquid $CO_2$ storage tank 14 and HP pump(s) 21, both integrated in CO2-CC section, CO2-HR heat exchanger units (e.g. 32, 33, 37, 65, 71A, 71B, 100), for vaporization and superheating of carbon dioxide 24, 25, 27 by use of waste heat sources, supraheating heat exchangers of carbon dioxide by use of process heat (i.e. MP $H_2/O_2$ combustion 28 or any other heat sources, and i.e. 14 in FIG. 2 described v.i.).

The set of $CO_2$ turbines for power generation (CO2-PG) consists of $CO_2$ HP back pressure turbines (FIG. 1; 30, 40), optionally with re-superheating (35, 41) and a final atmospheric turbine 42 that can address the peak need for electricity.

According to present process invention, it is advantageous that the default pressure of HP $CO_2$ back pressure turbine 30 with generator 44, will set slightly over the critical pressure of carbon dioxide, so the power generation for the next turbine stage 40 and recycling $CO_2$ stream, 31 to CO2-HR, 32 and re-liquification, 33 to 34 can be kept in a thermodynamically optimum point. Depending on the sequestration point, EOR 39 or further applications (e.g. biological $CO_2$ conversion to hydrocarbons 43 and/or for regeneration of $CO_2$ dehydration column 9) the next stage(s) of $CO_2$ turbine can be set accordingly. Therefore part of carbon dioxide will be recycled 31 to 34 while the other part will be exported for other purposes 39, 43, whence semi-closed liquid-gas $CO_2$ cycle is ascribed to this cycle. The remaining part in this cycle is re-superheated upstream of each turbine section (31, 36 through re-heaters 35, 41).

To (e):

The residual hydrogen will be stripped out of the Direct Steam condensate 66 by a thermal desorber 67. The residual hydrogen 68 can be recycled by use of a recycle compressor 69 returned to MP hydrogen/oxygen combustion section 70. While the MP Direct Steam condensate 66 is first fed to hydrogen stripper 67, then, it can be fed after the CO2-HR 71A and undercooling into a Kaplan or Francis turbine 72 regaining additional power via cycle (e). The cycle (e) can be deemed as semi-open because of chemically pure Direct Steam condensate 73, which can be fed into the HPLTE-Syngas Generator and/or used for desuperheating of Direct Steam through the torches after a simplified final polishing.

Considering the above five cycles, generally a set of five turbines is deployed for generation of export power. While a minor part of driving force of the turbines is needed to address the driving power for $CO_2$ recompressor of ACU (FIG. 1, 46 mit regasified $CO_2$ as 45, then compressed 46 and recycled to the $CO_2$ cycle) and the recompression of MP/LP hydrogen stream 69 as well eventually as driving force for the pumps.

The present process for high pressure ultra-superheated Direct Steam generation employs number of special torches 54. The torches are arranged in a serial order with quenching by temperature controlled operation measure which ensures the control of high evolved heat, generated by direct combustion of hydrogen side stream into the main oxygen stream and/or more preferably, oxygen side stream in the hydrogen main stream. The assembly of torch is distinguished by torch's internal and jacket cooling coils, temperature controlled injection of water into and/or in the surrounding area around the torch's flare and the flare pathway within the combustion chamber with internal and/or jacket cooling. The combustion chamber is preferably carried out in a cylindrical refractory lining and/or a refractory skirt with interfacial cooling coils emplaced behind the skirt.

The injection of water into the high temperature combustion flame and the surrounding area enables to prevent the evolvement of uncontrolled high temperature at one side, while at the other side; additional direct saturated, rather than superheated, more preferably ultra-superheated steam is generated.

The Direct Steam generation is carried out by a number of torches that is distinctively fed with:
(a) hydrogen, preferably as primary carrier stream of the torch
(b) oxygen injection into the torch as secondary stream (either pure oxygen or a blend of oxygen-steam)
(c) internal water in different coil of cooling circuits of torches (preferably from BFW of MP steam generation section or combined with CO2-HR section)
(d) Saturated steam injection for cooling behind the refractory skirt merging into the main Direct Steam stream (referred to as "open-end jacket cooling")
(e) Jacket cooling section(s) of the combustion chamber for $CO_2$ superheating and/or $CO_2$ supraheating as part of CO2-HR (referred to as "closed-end jacket cooling")

These characteristic features above distinguishes the torch devices in the present invention for the primary HP Direct Steam and the torch device for re-superheating of Direct Steam in MP/LP sections of the turbine from other $H_2/O_2$ combustion devices e.g. as installed in the super-modern SABRE jet engine.

The evolved process heat from combustion of hydrogen/oxygen above facilitates also the process heat sources for supraheating, re-superheating of $CO_2$ steam generation in MP boiler and superheating of steam for the steam condensation turbine or any back pressure turbine.

The torch device for Direct Steam generation is further distinguished by conditioning of the steam with alkalization of steam i.e. with ammonia injection into the steam stream, similar like the common alkalization of demi-water in boiler feed water preparation in case for application of carbon steel. The extent of alkalization can be easily checked via inline steam condensate analysis.

The present process invention for carbon capture and separation by way of condensation CO2-CC, utilization for heat recovery CO2-HR with ACU and power generation CO2-PG in combination with the HPLTE-Syngas Generator provides the utmost viable commercial way to super-efficient hydrogen based fossil power generation in any scale, preferably large scale power plants. By virtue of the above advantageous features in regards to investment and the O&M (Operation and Maintenance) aspects, the present process for power generation is capable to supplant the nuclear power generation up for long-term future.

With this process, many of presently existing well-known features of conventional fossil power plants are either deleted entirely or reduced in footprint considerably. Specifically, the huge cooling tower of fossil or nuclear power plants, which was necessary to the present time, is deleted out of the power plant facility.

Respectively, the extent of dilapidating of thermal energy in the margin of 40% to over 43% from the fossil or up to 45% in nuclear power plant is recovered by CO2-HR and converted to electricity through CO2-PG section. Instead of the huge cooling tower, small number of cooling water units are considered, because the CO2-HR with regasification of carbon dioxide overtakes the cooling purposes down to 87° F. for most of the annual operation time. The most advantageous feature for recovery of dissipated thermal energy and availing it in a great margin for additional power generation, leads to the opportunity to either reduction of fossil feedstock input into the power plant by keeping the same electric output or increase of additional electric power output by same fossil feedstock input, therefore leading to lower electricity price in either case.

Currently, the very expensive and high maintenance natural gas fed gas turbines are deemed as the best available fossil power plants with a gross efficiency up about 60% with extensive HRSG section and other measures. At the other side, the power generation via conventional fired power plants (based on coal, biomass, oil, natural gas and other resources) requires a huge building for HRSG heat recovery steam generation consisting of great number of tube lined heat exchanger trains for indirect generation of steam resulting in a gross efficiency of 50% to 55% in average.

However, the utilization of CO2-HR, CO2-PG, HP Direct Steam generation and the set of turbines opens the way for super-efficient compact fossil power plants in the margin of 80% to 85%. Higher efficiency can be achieved during the winter season or in the cold region, where the need for ACU is negligible or not necessary.

The Direct Steam according to present process invention (in the context of the new Second Thermodynamic Cycle) is furnished at high pressure (typically 300 bar and 850° C. or higher temperature). The steam under this condition is commonly referred to as ultra-superheated steam. At the present state-of-the-art, the ultra-superheated steam is considered to be furnished by indirect heat exchange like the HRSG of conventional power plants. However, the present process generates the Direct Steam without employing huge HRSG section that is made of carbon steel. The Direct Steam is generated in a very compact way, so stainless steel material can be readily applied without steam conditioning close upstream of the steam turbine and/or in each re-superheating section with steam injected $O_2/H_2$ torch (FIG. 4, B).

The present process for carbon capture, utilization, power generation and chemical conversion of carbon dioxide provides also the technical-commercially feasible way for manufacturing of number of chemicals i.e. ammonia, methanol, ethanol, SNG, propane, butane, as well as liquid fuels i.e. automotive fuels, cerosin manufacturing via MTG or Fischer Tropsch synthesis for gasoline, DME, other commodity products and number of fine chemicals originally produced by natural gas and crude oil without any $CO_2$ emission into the atmosphere. Therefore the present polygeneration process for syngas and power generation performs final products, which all would be also available from natural gas or crude oil by preserving the fossil resources and sustaining present source of energy for farer time horizon.

For instance, the present process deletes the flue gas chimney or the stack in gas turbine power plants with electric precipitator, culprit for emission of harmful constituent and carbon dioxide totally. These latter units in both kinds of plants are replaced with scrubber and CO2-HR units. The cleansed $CO_2$ free offgas downstream of CO2-CC is preheated and directed to an expander turbine before it is released into the atmosphere (FIG. 2).

By virtue of the sections of present process invention, even the scenery of this kind of fossil power plants differs from all other existing kind of fossil power plants. Namely, there is no cooling tower, no chimney for flue gas, no huge plant section for ACR (Acid Gas Removal for $CO_2$ removal by way of Selexol, Rectisol, PSA or Benfield) in chemical plant or gasification plants. There are also no longer huge building for tube lined heat exchanger trails (e.g. HRSG in combustion stream of convention coal fired power plants), more particularly, there is no costly, high maintenance gas turbine (neither in combined cycle nor in single cycle) employed in this kind of super modern fossil power plants. Depending upon final product of a gasification process, the HPLTE-Syngas Generator is capable to either reduce the footprint of cryogenic air separation unit or to delete it entirely by supplying HP/MP pure oxygen from the anodic product of the HPLTE-Syngas Generator. The excess oxygen can be exported as GOX (i.e. for oxyfueling or gasification process) or LOX for sale.

Thus the present process for power generation is based on hydrogen/oxygen combustion; the obtained process water out of the Francis turbine is chemical-bacteriological pure, ready for simplified finalization and reuse as boiler feed water and/or part of the make-up water for HPLTE-Syngas Generator. The other part of water for the HP electrolysis is to be prepared by way of water treatment. This process reduces the scope of the large plant section for boiler feed water, cooling water and waste water treatment installed for steam generation purpose.

Based on the grounds that major part of global carbon emission can be ascribed to fossil power plants, chemical facilities, aluminum, pulp and paper and cement manufacturing the present process furnishes a solid solution for restoration of global GHG. By virtue of super-efficient hydrogen based fossil power plants along with CO2-PG section, resulting in lower power generation costs, the present process provides only remedies for reduction of carbon emission from transportation vehicles, if more electric and hybrid vehicles would be participating on the road.

It shall be highlighted that this process favors the application of high carbon containing fuels for super-efficient fossil power plants. Considering this fact, the more carbon rich is the fuel the more advantageous processing can be achieved respectively. Therefore, the petcoke and coal (high rank or low rank grades) are the most best fuels before other resources e.g. biomass, crude oil, waste carbonaceous materials, which are all ranking before the natural gas (with reference to IEA reports and fuel classifications as regards to carbon emission and GHG for climate control).

Since the high pressure gasification of those bulk solid carbonaceous material Figures the best advanced processing for conversion of those feedstock for chemicals and power generation, the high pressure bulk solid feeding of the high pressure gasifier is the imperative prerequisite for achievement of high efficient chemical processing of syngas to value-added chemicals and the super-efficient hydrogen based fossil power plants as well. In this aspect, the Aerojet Rocketdyne (former PWR) high pressure Dry Pump and the U.S. Ser. No. 13/261,207 (in pursuant to PCT/US2010/002482 or EP 09 012 157.5) are fulfilling the above sine qua non for bulk solid fueled advanced syngas and hydrogen based fossil power plants.

Upon the present technology, the Zero Carbon Emission Concept can be attained with technologically and economically profitable advantages that can be implemented not only in new plants, but also in retrofitting of existing commercial plants for chemicals, aluminum, steel manufacturing, cement, pulp and paper and more beneficially for existing conventional fossil feedstock fired power plants (coal, biomass, petcoke, municipal waste, crude oil, oil distillates, natural gas). The total carbon capture in the sense of present process comprises both the $CO_2$ emission as well the fine soot pollutants, referred to as Black Carbon emission.

In contrast to all presently known carbon capture technologies, which lead to an increase of operation and maintenance costs—respectively to lowering the revenue of plant and inevitably increase of electricity price for fossil power plants, this process allows the total capturing of carbon dioxide with economically profitable aspects. That is achieved, because of the advantageous measure for harnessing of lost waste heats via CO2-HR into useful process heat, additional generation of electric power with CO2-PG section and availing of carbon dioxide as precursor for polygeneration of value-added products are achieved by oxygen and syngas through HPLTE-Syngas Generator as well.

The application of present process will be described on the basis for total carbon capture from flue gas of existing fossil power plants exemplary, without restricting of any other embodiments.

This embodiment of present process is provided (in accordance to the FIG. 2) with the hot $CO_2$ containing Flue Gas 1 downstream of electric precipitator of the plant or stack of gas turbine power plants (typically in the margin of 150° to 170° C. in GTCC). The Flue Gas is first fed to a row flue gas scrubber 2 that removes the majority of particulate pollutants i.e. ash, soot and other aerosols as well as part of gaseous harmful constituents like sulfur oxides, nitrogen oxides, slippage of ammonia from SCR DeNOx section or urea from non-catalytic DeNOx section and other organic constituents like furan. The scrubber 2 recovers those pollutants, in particular soot pollutant that is most second culprit for climate change after carbon dioxide (referred to as Black Carbon emission). The scrubber recoups also the flue gas waste heat by way of circulating water and CCC-HR closed cooling circuit 50, 55, 56 and via CO2-HR through 51, 52, 53, 71 and 74 described.

The row Flue Gas scrubber 2 is fed with discharge water 27 in counter flow of upstream 3 (optionally with row gas blower 4) in row gas wash tower 5. The discharge of laden scrubber water 29, through pump 30 to 32 is subject to waste water treatment and removal and disposal of harmful constituent e.g. via bacteriological waste water treatment, while the other part of circulating scrubber water will be filtered 33 and recycled to scrubber 34). The filtration and recirculation takes likewise in wash tower 5 with 24, 25, 26, 28, wherefore the wash tower is equipped with recirculation sections (28, 51, 25, 52, and 25, 53 with 20, 23 and 21).

The residual of the above pollutant's traces are removed from the Flue Gas by way of row gas wash tower 5, preferably consisting of number of section that is fed with clean process condensate 18, 19, 20, 21 in counter flow from upstream sections i.e. process condensate 18 from the compressor's intercoolers 14 and 15 separators.

The remaining heat of flue gas is recovered in CCC-HR units FIG. 2, B of row gas wash tower, so the most part of water constituent of the Flue Gas—obtained from combustion of carbonaceous feed stock—is removed from the cleansed Flue Gas stream 6, upstream of first compression stage 7. This middle pressure scrubber (referred to as MP Scrubber) shall remove low concentration traces i.e. NOx, SOx as well as volatile constituents i.e. Mercury, Antimony, and other compounds like furan. The Flue Gas outlet temperature of stream 41 will be in a margin of 40° to 30° C. depending on operation condition of CCC-HR.

The set of machinery is consisting of multistage Flue Gas compressor 7 with intercoolers 14 and separators 15 and offgas expander turbine 9 (to some degree resembling the machinery set of dual-pressure nitric acid plants), that is equipped with attached high pressure $CO_2$ multistage expander turbine 8, (optionally in semi-closed cycle whereby part the export gaseous $CO_2$ after the $CO_2$ turbine can be harnessed for EOR/IOR through 69). Because of the positive gross power output in normal mode of operation, the power output is considerably greater than the required power input, so additional power generation is regained by the main generator 12 over 13. The electric propulsion of the machinery set (depicted at the left-hand side of machinery set in FIG. 2; 10) is deemed for start-up period only. The electric propulsion will be de-clutched after the completion of start-up phase 11.

The Flue Gas compressor stages are considered in the meaning of present process invention in a way, that the heat recovery downstream of compressed Flue Gas in every section is recovered by intercooler 14 that is integrated in the CO2-HR units (either in a centralized unit, FIG. 2, B or individually CO2-HR units). Typically the compressor is consisting of three stages, so the outlet of last stage 42 (typically in the margin 75 to 77 barg) will fit the required CO2-CC unit for dehydration and condensation conditions.

The present process includes the removal of very stringent harmful constituent with low partial pressure such As and Hg mercury, furan and dioxin traces through adsorption bed that works intermittently in operation and regeneration once exhausted in capacity (i.e. activated carbon bed, molecular sieves, Pillard Clays adsorbens and/or chemically active solid reactants). The adsorber beds are installed downstream of interim gas-condensate separators and upstream of the next compression stage (referred to as MP Adsorber, not depicted in FIG. 2).

The obtained MP process condensates 19 (typically in margin 10 to 50 barg) are consisting of widely pure water (without any calcium or magnesium carbonate and other water hardening constituents) that can easily recycled and reused after softening with relatively minor technical requirements.

Therefore, the present process considers the power recovery of MP process condensate by use of a Francis turbine, more preferably a Kaplan turbine 16, before discharging the condensate 19 to water treatment or upstream row flue gas scrubber 18.

The widely dry pressurized Flue Gas stream downstream of last compression stage 42 is subject to CO2-HR, CCC-HR, and CO2-CC. The recovered liquid $CO_2$ is further processed to various applications outlined v.s. and/or directed for re-gasification, superheating and supraheating prior to CO2-PG.

The remaining $CO_2$-free offgas 43 is primarily consisting of residual nitrogen that was taken in from intake air manifold of main combustion air blower upstream of combustion chamber. This offgas can be preheated by use of waste heat recovery and conducted over the offgas expander 9, attached to the main shaft of machinery set, and then released into the atmosphere 44 as cleansed offgas without carbon dioxide out of the plant. The Flue Gas compressor is further driven by employment of the $CO_2$, of 67, 68 of the First Thermodynamic Cycle via multi stage $CO_2$ turbine.

Appendix A: Further elaboration for the two new thermodynamic cycles of the present process invention The present appendix is added into the content of this process invention for ease of elaboration for the two new thermodynamic cycles by use of thermodynamic charts (FIGS. 4, A and B respectively).

The First Thermodynamic Cycle is pertaining to availing of any process working media, particularly liquid gases, more specifically liquid carbon dioxide, embarked for heat recovery and power generation. The new Second Thermodynamic Cycle is entered by way of ultra superheated Direct Steam generation by a different thermodynamic trajectory than the classic Rankin cycle. The latter is also pivotal in the present process invention for facilitation of super-efficient power plant technology.

I. The First Thermodynamic Cycle

This cycle is invented for heat recovery power generation. It comprises the recouping of any wasted heat, and optionally the sensible process heat in addition. Those heat sources are availed for the overall thermal energy for driving a working machine. The performed work of the power machine is either intended to drive a working machine e.g. pump, compressor (i.e. Flue Gas, syngas, ACU, natural gas compressor) and/or a generator. For this purpose, by taking on the carbon dioxide as the working fluid, the cycle is consisting of a reservoir of liquid carbon dioxide, which is charged from the main $CO_2$ condenser. The $CO_2$ liquefaction is performed according to CO2-CC section. The waste and process heat recovery is performed via $CO_2$ vaporization, superheating and supraheating in the CO2-HR section.

The superheated/supraheated $CO_2$ is routed to the $CO_2$ multistage turbine in the CO2-PG section. The set of $CO_2$ turbine comprises HP/MP/LP sections, driven with $CO_2$ working media via closed cycle, or preferably via semi-closed cycle, whereas part of the liquid carbon dioxide is extracted from the cycle to another purposes e.i. HPLTE-Syngas Generator. The extracted excess liquid $CO_2$ to the HLPTE-SG is named as "Export Liq-$CO_2$".

The extent of the Export Liq-$CO_2$ relates from two aspects to the generated product streams CO/$2H_2$ and oxygen out of the HPLTE-SG from circulating mass flow rate of $CO_2$ point of view. One is due because these low temperature streams are the prime media for the condensation of $CO_2$ of the First Thermodynamic Cycle along the trajectory 6-7 in FIG. 4,A, so each one can be availed in multiple time via multi-stage expander turbines for syngas and oxygen (illustratively presented for oxygen in FIG. 5A and carbon monoxide in FIG. 5B).

The other aspect is pertaining to the mol stream of the HPLTE-Syngas Generator's products. The HPLTE-Syngas Generator is fed with one mol stream liquid $CO_2$ and two mol streams water via pumping, while 4.5 mol gaseous product streams (CO/$2H_2$ and 3/2 $O_2$) are obtained under e.g. 300 bar and 15° C. primarily. Hence this the both above factors perform a vast potential for condensation capacity of $CO_2$ along the line 6-7 in favor of the First Thermodynamic Cycle. While the product streams are of the HPLTE-Syngas Generator superheated prior each turbine stage (FIGS. 5 A, B). Therefore, the circulating mass flow rate of $CO_2$ in the First Thermodynamic Cycle is interlinked typically between 3 to 20 times of the Export Liq-$CO_2$ mass flow rate, depending on the site location and the season. In addition, the use of thermal energy of the primary fossil input material is reached down to 31° C. that equates nearly the average ambient temperature. The waste heat recovery comprises any kind of wasted heat that is else dissipated from the thermodynamic system. The waste heat sources are process integrated heat sources i.e. downstream of chemical reactors, thermal processing and power generation like the off-steam downstream of the steam condensation turbine (usually in the margin of 120° C. to 130° C. under prevailing pressure of about 0.9 bar a). These thermal energy streams are currently dissipated via cooling water, air cooler and wet cooling tower into the atmosphere.

Operation Field of the First Thermodynamic Cycle

The First Thermodynamic Cycle is illustrated based on temperature-entropy chart via FIG. 4, A. The capture of liquid carbon dioxide is carried out through cooling above the sublimation temperature line at the prevailing pressure, preferably above the critical temperature of 31° C. and critical pressure of 74 bar g. The FIG. 4, A relates to subcritical undercooling 7-1, subcritical-supercritical vaporization 2-3-4 and supraheating 4-5, then supercritical regenerative heat exchange and $CO_2$ condensation without interfering into the two phase zone. The operation of this cycle for subcritical condensation of $CO_2$ with interference into the two-phase-zone is not depicted in this figure. According to the present process, the latter field of operation can be carried out in cold region or in winter season, whereby the ambient temperature below the critical temperature of $CO_2$ can be availed as an additional cooling agent (e.g. via air cooler). At ease of illustration, the reheating stages are not depicted in this Figure either.

Further, the circulating mass flow of carbon dioxide in this cycle comprises typically 3 to 20 times of the mass flow rate of the Export Liq-$CO_2$ to the HPLTE-Syngas Generator, even tough the two mass flow rates are hermetically separated. The cycle commences with liquid $CO_2$ downstream of main condenser by the isobaric at point 1. As regards to the make-up carbon dioxide, this step is presenting CO2-CC section of the new process. The system is distinctively characterized by following stages:

Step-1: Isentropic pressure elevation of liquid $CO_2$ by use of high pressure pump along the trajectory 1-2 e.g. 300 bar that is optionally carried out in a polytropic way as regards to the $CO_2$ pumping (i.e. jacket and shaft cooling of the pump and/or multi-stage pumping/cooling with/or without booster pump)

Step-2: Isobaric subcritical preheating of liquid $CO_2$ carried out below the critical point and upstream of vaporization along the trajectory 2-3. This step resembles the economizer in classic Rankin cycle. The step 2-3 is carried out by waste heat recovery with a waste heat source that performs the preheating of the liquid $CO_2$ prior to the steps 3-4. This step incorporates part of the CO2-HR heat recovery section of this process invention.

Step-3: Isobaric vaporization and superheating of $CO_2$ from subcritical condition over the critical point to the supercritical region along the trajectory 3-4 whereas the routing reaches from the left side of the critical point to superheated area, that is performed for instance by following measures:

(i) Preheating and vaporization is carried out by wasted heat sources, e.g. intercoolers of the compressors employed in the site (e.g. Flue Gas scrubber heat exchanger and Flue Gas compressor of conventional fired power plants, LP/MP syngas compressor from gasification section, etc.), steam downstream of steam turbine, and process gas cooling. This step represents also part of the CO2-HR heat recovery section of this process (ii) The regenerative heating by way of $CO_2$ heat exchange (FIG. 4, B) takes place with i.e. by the off steam downstream of the steam turbine (and/or in connection with the Second Thermodynamic Cycle along the trajectory 10'-1" of the FIG. 4,B). The regenerative heat exchange hereby can take also place with liquid $CO_2$ that is vaporized/superheated along 3-4, thus i.e. along the trajectory 3-4 against 6-7. Preferably, the heat source can be also in part the regenerative heat of the $CO_2$ stream downstream of $CO_2$ turbine (along the path 6-7).

Step-4: Further isobaric CO2-HR superheating, referred to as suprahaeting, along the trajectory 4-5, to any temperature, typically 300° C. to 850° C., for instance. Any source of process heat can be employed for $CO_2$ suprahaeting e.g. process heat in combustion chamber of any firing units (i.e. coal, crude oil, natural gas, gas turbine HRSG section), hot syngas of gasification, Direct Steam heating, auxiliary furnace, i.e. auxiliary HP natural gas-oxygen fired combustion unit via total oxidation, more specifically HP natural gas-oxygen gasification heat, whereby additional syngas is also obtained.

Step-5: Isentropic expansion of suprahaeted $CO_2$ along the trajectory 5-6, whereby the HP and MP sections of a backpressure expander $CO_2$ turbine are employed that releases the suprahaeted $CO_2$ down to lower pressure level.

Step-6: Isobaric regenerative heat exchange and condensation from superheated $CO_2$ over the critical point takes place along the 6-7. Whereby the regenerative heat exchange comprises:

(i) Preheating of cold process media i.e. HP/MP/LP gaseous products of HPLTE-Syngas Generator up/downstream of syngas and oxygen back pressure expander turbines, whereas one and the same product can be availed multiple of time for heat recovery from the CO2 cycle (FIG. 5), (ii) with LP/MP-steam generation consumed and condensed within the process for various plant internal purposes (e.g. utilized for economizer, steam to de-aerator, etc.).

(iii) Preheating of other process media that are inherent part of the plant site (e.g. combustion or process air preheater)

(iv) Residual middle temperature cooling of the system by employing of dry air cooler accommodated in favor of preheating of internal cold process media, see below.

(v) Preheating of desuperheating water for injection into hydrogen-oxygen combustion stream of torch (employed in new Second Thermodynamic Cycle)

Then, the closing of $CO_2$ cycle via supercritical $CO_2$ cooling and condensation downstream of the regenerative heat exchange above performs by minimal condensation heat. The closing of $CO_2$ cycle via supercritical-subcritical cooling and condensation of $CO_2$ downstream of the regenerative heat exchange is considered for cold locations and/or the winter season. In case the condensation is performed by availing of any other cooling media, i.e. ACU, air cooler and/or wet cooling unit, whereby the line 6-7 of FIG. 4, A interferes in part into the two phase zone (not depicted in this Figure). More specifically, v.i. the gaseous products of HPLTE-Syngas Generator are availed as cooling and condensation agent.

Step-7: Isobaric undercooling of liquid $CO_2$ along 7-1 below 31° to 10° C., the acceptable temperature by high pressure pump, whereby a partial vaporization within the pump is safely prevented. The undercooling depends on final outlet pressure of the pump (and/or the pump stages) about ca. 250 to 300 bar, for instance. The undercooling is illustrated in chart 1 along the line 7-1.

Specifically, the $CO_2$ cooling and condensation is considered by preheating of oxygen and syngas streams obtained downstream of HPLTE-Syngas Generator and/or the preheating of those working fluids upstream of each turbine section. This measure is pivotal for the First Thermodynamic Cycle for reason of high thermal energy efficiency. The four stage-preheating of oxygen in a pressure-enthalpy chart for oxygen is illustrated exemplary in FIG. 5, A (in the temperature margin of 15° C. to 170° C. in counter-flow to $CO_2$ stream downstream of $CO_2$ regenerative heat exchangers of $CO_2$ cycle). Like oxygen stream, the cold syngas stream is also harnessed for multiple times for cooling and condensation of $CO_2$ of the First Thermodynamic Cycle. The FIG. 5, B demonstrates illustratively the four stages preheating of CO constituent of syngas $CO/2H_2$ stream down to 40 bar pressure level. Likewise, the concomitant hydrogen of the syngas constituent contributes to cooling and condensation of $CO_2$ of the First Thermodynamic Cycle in the very same multiple of times.

The characteristic features of the First Thermodynamic Cycle

From thermodynamic aspects, the First Thermodynamic Cycle is recognized by some characteristic features that are conducive for some poignant advantages, which can be summarized schematically below:

(i) The pressurized process media is preheated and superheated starting from point 2 at the left side of the critical point. The transformation of liquid phase from the subcritical area to the gaseous phase into supercritical region is performed without the interfering of the two phase zone.

(ii) The preheating and superheating process is recognized by the routing of the isobaric trajectories left of the critical point, which are favorable by a steep upwards routing along the 2-3-4-5 trajectory.

(iii) The isentropic expansion of the superheated/supraheated working fluid (shown in orange) from 5 over the expander turbine is carried out down to an isobaric line, preferably above the critical pressure isobaric, so the condensation requires first a minimum of enthalpy change at one hand, while at the other hand, a regenerative heat exchange is implemented in favor of higher efficiency.

(iv) The regenerative heat exchange section; typically along the isobaric 6-7 above the critical point (shown in part by blue area) is considered for preheating of various internal process media, like ancillary LP steam generation. Further cooling agent for closing the cycle can be executed with the cold gaseous products from HPLTE-Syngas Generator, whereby the $CO_2$ isobaric "slips" from supercritical area over the critical point to subcritical area, with a minimum change of the enthalpy.

(v) Further undercooling of liquid $CO_2$ prior to the high pressure pump is designated e.g. by partially vaporization of the $CO_2$ and re-compressing of that $CO_2$ back to the cycle.

The advantages of this cycle from processing and mechanical design aspects

The characteristic features and advantageous the First Thermodynamic Cycle from processing and mechanical design shall be described as follows:

(i) This cycle allows the reuse of the most part of the low temperature thermal energy which is otherwise wasted with other media like water into the atmosphere, e.g. via the cooling tower and chimney.

(ii) The additional point is in conjunction to relative high molecular weight of $CO_2$, for instance compared with water, it is about 2.4 times heavier, respectively higher potential of kinetic energy through the expander turbines.

(iii) Due to the "dense" routing of the isochors along the line 2-3-4-5, the required heat exchangers are distinguished with high heat exchange coefficient, leading to compact design and size of the equipment. That meets also the requirement for heat exchangers employed for the cooling along the line 6-7-1 as well.

(iv) The excess heat subject to remove out of the system, can be carried out at higher temperature, so dry air cooler can be installed for outbalancing of heat exchange, e.g. under variation of seasonal circumstances.

(v) The regenerative cooling and condensation in this cycle is distinctively flexible with changes in season. For instance, minor part of liquid $CO_2$ can be released to lower pressure that provides significant cooling capability, this part is subject to re-compression, however. As a rule of dumb in extreme case, one part of released $CO_2$ can condensate 4 part $CO_2$ respectively.

(vi) In conjunction with CO2-CC for separation of $CO_2$ by way of condensation the present process invention replaces the large scale plant unit for AGR (Acid Gas Removal) by use of chemicals e.g. Selexol, Rectisol, which certainly is costly in investment and high in maintenance.

II. The Second Thermodynamic Cycle

With present process invention and nearly cost-neutral conversion of $CO_2$ by HPLTE-Syngas Generator, performs the availability of low costs high pressure oxygen, which is substantiated in an unprecedented cost effective feasibility. As the same token, the high pressure low costs hydrogen can also be performed via gasification, more specifically HP gasification. These specific features for low costs hydrogen and oxygen had led to the concept of high pressure supercritical and/or ultra superheated Direct Steam generation that is obtained by direct combustion of hydrogen and oxygen with water injection (deigned for temperature control and desuperheating). By way of $H_2/O_2$ combustion, the system doesn't interfere into the two phase zone. With this measure the ultra superheated, supercritical high pressure Direct Steam is generated in an extraordinary compact footprint, which provides number of far-reaching ease in processing and mechanical design, compared with the classic Rankin cycle for facilitation of ultra superheated steam in future.

Operation Field of the Second Thermodynamic Cycle

The characteristic peculiarities of this cycle are presented on the temperature-entropy chart in FIG. 4, B. Within this chart, the classic Rankin cycle for ultra-superheated steam is embedded (shown in blue area) for reason of distinctive differences with the new invented cycle. The system has the following typical stages without any limitation of the invented process:

Step-1: Sequential combustion of high pressure hydrogen with oxygen or oxygen/steam blends, whereas the high pressure hydrogen is performed by hydrogen compressor, which is obtained first by high pressure Gasification Island. The sequential combustion applies for the primary Direct Steam as well for reheating Direct Steam generation. The high pressure gasification plant island delivers a clean syngas at a pressure equal or higher than the critical pressure of $CO_2$, so the hydrogen is obtained downstream of CO2-CC and upstream of hydrogen compressor at least at 75 bar g pressure. The sequential combustion for Direct Steam generation is performed by special hydrogen-oxygen torches, generating high temperature steam at the point 2' prevailing in the flame of the torch along an isobaric trajectory routing left of the critical point of water and above the critical isobaric of the water (for instance the 300 bar isobaric line). The point 2' is not depicted in the chart.

Step-2: Injection of temperature controlled water from point 1 and desuperheating of the flame steam and in situ generation of additional Direct Steam, whereas the point 2 is attained, close upstream of the HP section of the turbine.

Steps-3-8:
Sequential release of Direct Steam through the typical arrangement of HP/MP/LP section of the steam turbine with individual reheating section, which is carried out by further hydrogen-oxygen combustion. The five turbine stages, spreading from two HP, two MP and one LP section are illustrated by the points 2-3, 3-4, 4-5, 5-6, 6-7, 7-8, 8-9, 9-10 schematically.

Step-9: LP Direct Steam upstream of the LP section of turbine from point 10 to 10'

Step-10: Partial or optionally total condensation of Direct Steam condensate along the line 10' to 1'' and reuse of the water for further purpose, whereby the undercooled steam condensate 1'' is further preheated to point 1 prior to injection.

The characteristic features of the new Second Thermnodynamic Cycle

From thermodynamic aspects, the Second Thermodynamic Cycle is distinguished by four characteristic features for facilitation of ultra superheated steam in a different way than based of Rankin cycle. The Second Thermodynamic Cycle is summarized schematically as follows:

(i) The Second Thermodynamic Cycle is first commenced by combustion point of high pressure gaseous hydrogen and oxygen (i.e. injection of oxygen into the hydrogen stream and/or vise versa), whereby the combustion is preferably executed along an isobaric trajectory—preferably left of the critical isobaric—so no trespass of the two phase zone shall be entered. More preferably the combustion isobaric shall not pass through the plateau, which reduces the extent of cycle's covered area. The combustion of hydrogen-oxygen leads to the point 2'' that is usually in the temperature field of 1800° C. to 2200° C., hence not depicted in the chart. The prevailing high temperature is stable within the field of the flame only. By controlled injection of preheated water from the point 1, the point 2 in the chart is stabilized.

Along this trajectory a shoulder is encompassed that is conducive for higher thermodynamic efficiency of the cycle. This represents the first distinguishing advantages of the new Cycle. Compared with the above Rankin cycle, additional area is gained by the surrounding points 1-2-3-3'-2'-1.

(ii) The second distinguishing characteristic of the new Thermodynamic Cycle is pertaining to high operation temperature (point 2, then the points 4, 6, 8, 10 after each re-superheating in the Orange field), which are conspicuously higher than the typical high temperature points of Rankin cycle for ultra superheated steam. For reason of comparison, the same isobaric trajectories are chosen to demonstrate the points 3, 5, 7 and 9 in the Blue field.

Therefore, the second characteristics demonstrate Dimondale areas in orange color between the superheated points of the two cycles, namely the 3-4-5-5'-1 and 5-6-7-7' and 7-8-9-9'.

The series of points 4, 6, 8 and 10 above represent the four levels of re-superheating stages upstream of each consecutive turbine stages. Respectively, the points 3, 5, 7 and 9 represent the four turbine stages in the Rankin cycle for ultra superheated steam. With the exception of the first isobaric of the new Cycle, all other isobaric are intentionally chosen as the same one in both cycles, determining the same design and working pressure in each superheated point. Thus by this measure the second distinguishing characteristic of the new Thermodynamic Cycle shall be reflected.

(iii) The third distinguishing characteristic is associated with the last stage of the steam turbine. In case of the Rankin cycle, it takes place from the point 9 (on the isobaric 9'-9-10), whereby the point 9 is reached upstream of the LP turbine section. The new Cycle takes place from the point 10 along the LP isobaric 9'-9-10, whereby now, the point 10' is reached out downstream of the LP turbine section, which is lower than the 9' of the Rankin cycle. Compared with the Rankin cycle, the Second Thermodynamic Cycle sets a narrow stripe left at the right side of the Rankin cycle, namely 9-10-10'-9'-9, that contributes also to an increase of the Second Thermodynamic Cycle's operation.

(iv) The fourth distinguishing characteristic advantage of the new Cycle is about the shifting the point 9' at the saturated line to lower point 10' in the new Cycle. This shifting leads to a band along the off-steam pressure downstream of the LP steam turbine.

In the classic water-steam closed Rankin cycle, the condensation line along the line 9'-1' corresponds to the closing-line of the cycle that is carried out by cooling and condensation of the off-steam, usually via cooling tower. The condensation heat in the margin of 80° to 60° C. is dissipated by the Rankin process to the atmosphere. Thus the condensation via cooling tower in Rankin cycle (line 9'-1') overlays the open line of the new Cycle along 10'-1''. The line 10'-1'' represents the condensation of Direct Steam in the new Cycle, which is standing lower than 9' of Rankin cycle. That would lead principally to greater condensation heat due the prevailing to lower pressure downstream of the steam turbine. However, the off-steam in the new Cycle is obtained from chemically pure hydrogen and oxygen that can be even released into atmosphere without any adverse impact. From practically point of view, only part of this pure steam can be regained by way of condensation (e.g. via $CO_2$ cycle) in order to cover the demand for desuperheating water and the make up water for HPLTE-Syngas Generator.

In contrast to the classic water-steam Rankin cycle with carbon steel material in great extent of HRSG section, the Direct Steam can be generated by affordable stainless steel material now because of very compact small footprint.

The advantages of the Second New Thermodynamic Cycle from processing and mechanical design aspects The paramount advantages of the Second Cycle can be summarized as follows:

(i) Particularly, the very costly and high maintenance gas turbine is out of the picture for super efficient fossil power plants.

(ii) The Direct Steam generation is carried out at noticeably higher temperature than the steam generation via Rankin cycle for ultra superheated cycle.

(iii) The point above is primarily founded on the grounds of very small footprint that justifies the application of more expensive stainless steel material instead of extremely large scale boiler and superheating section of Rankin cycle with boiler vessel, circulation heat exchanger trials, steam drum and superheating trials.

(iv) The huge boiler-superheating HRSG building is eliminated entirely. The generation of Direct Steam can take place in one or multiple arrangements of the torches in "pipe(s)" in about 200 feet upstream of the HP section of steam turbine's intake nuzzles, or in shorter distance along the re-superheating sections, respectively. Thus from investment point of view, the mechanical design of the system is tremendously reduced because of very compact footprint.

(v) At the other hand, the applied material can be easily made of stainless steel, in order to regain chemically pure steam condensate without any kind of contamination or adverse impact to the environment.

(vi) As result of Direct Steam generation, the chimney is eliminated. So the most accused element of the fossil energy culprit for emission of harmful constituents e.g. Mercury, Antimony, flying ash, radioactivity from radioactive coal pollutants and Black Carbon emission (during the soot blowing) doesn't take place anymore.

(vii) Other units, removed from the landscape of power plants, are cooling tower, large scale water softening, preparation of demi water and BFW are eliminated out of the scenery of the power plant as well (viii) Respectively, there are far less plant units and equipment subject for investment, operation and maintenance.

Appendix B: Description of the major embodiments via the FIGS. 1 to 5

Brief description of the embodiment in the FIG. 1 and the elements thereto

In the FIG. 1, for the embodiment of the present process applied to pre-combustion carbon capture is presented, whereas the carbon dioxide CO2-CC cooling and condensation section, Auxiliary Cooling Unit ACU, with the sections for heat recovery via the first thermodynamic cycle First Thermodynamic Cycle for the waste and process heat recovery by utilization of liquefied-gaseous CO2 in the CO2-HR and in the power generation CO2-PG are presented. The CO2 turbine in the CO2-PG drives the compressor(s) and/or the generator(s) for additional generation of electricity. A detail description of the First and the Second Thermodynamic Cycle first and the second thermodynamic cycle are presented in the Appendix A. The FIG. 1 presents the pre-combustion carbon capture in connection with a CO2 stream, which could be obtained either by MP/LP gasification or by HP gasification process from any carbonaceous feedstock. These two options are distinctively presented in the element 3 of the FIG. 1.

Figure 6:
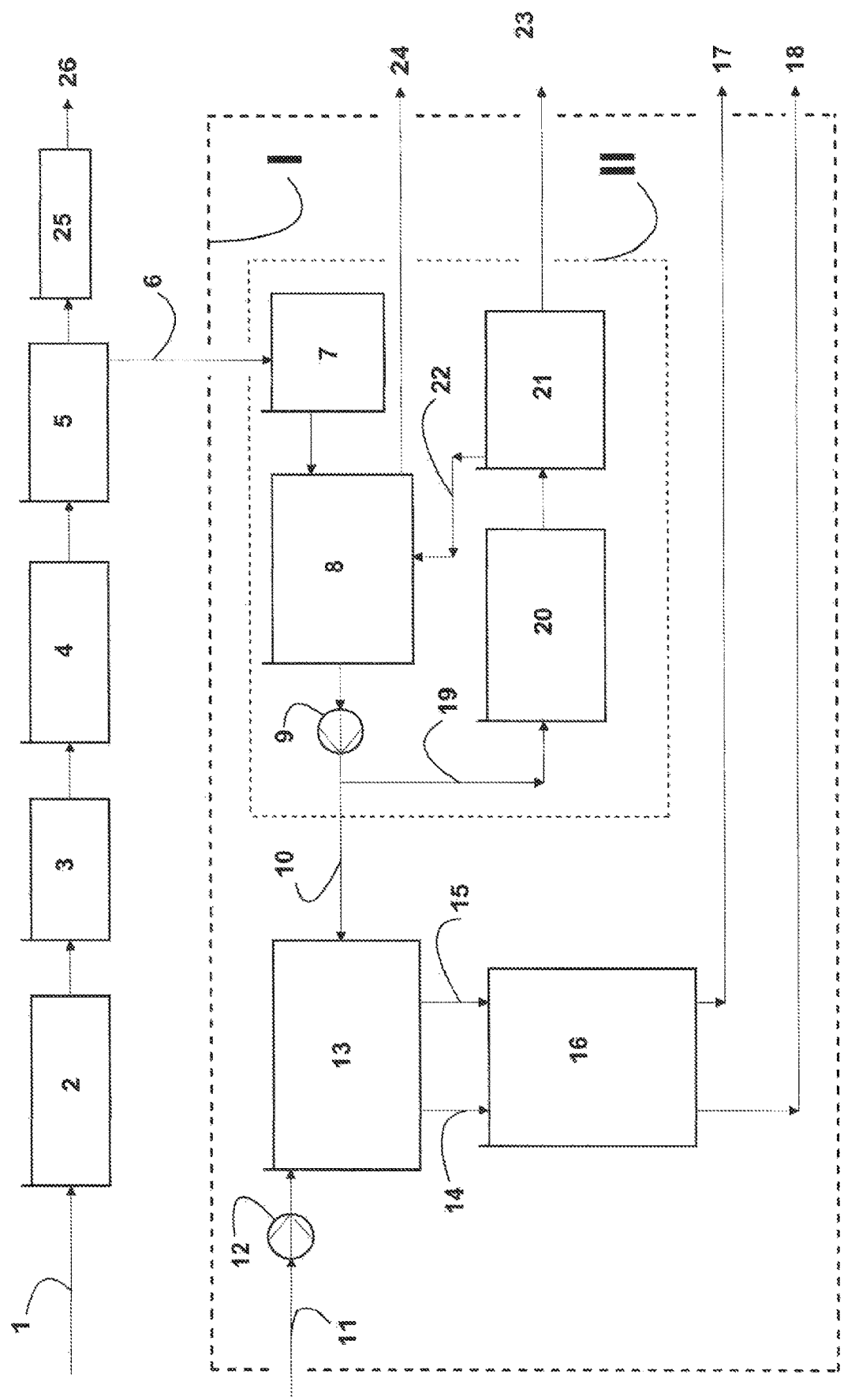

The pertinent processing block diagrams for MP/LP gasification application is illustrated in the FIG. 6. The pertinent processing block diagrams for HP gasification application is illustrated in the FIG. 7.

A detail description of the processing in the embodiment presented in the FIG. 1 has been provided in the body of the process description. The detail descriptions of the block diagrams FIGS. 6 and 7 has been provided in the Appendix C.

| Element | Description of the element |
|---|---|
| 1 | $CO_2$ containing syngas gas from the HP or MP/LP gasification process |
| 2 | Row gas treatment for clean-up from entrained slag and tar particles in syngas scrubber, COS hydrolysis, mercury removal, Acid Gas Removal for separation of sulfur constituents |
| 3 | Two represented cases; one for MP/LP gasification case, wherein an interim compressor for the $CO_2$ containing syngas is presented. In the second case, the $CO_2$ containing syngas is obtained from the HP gasification process. If the high-pressure gasification is operating noticeably above the critical pressure of the carbon dioxide, an interim syngas can be optionally employed in this embodiment. |
| 4 | Cleansed and conditioned $CO_2$ containing syngas upstream of water-shift converter |
| 5 | Injection steam upstream of CO-water shift converters |
| 6 | High temperature, and low temperature CO-water shift converter |
| 7 | Hydrogen syngas gas or hydrogen/carbon monoxide conditioned syngas (e.g. for methanol synthesis) with high portion of carbon dioxide |
| 8 | Super critical gas cooler operating above the critical pressure of carbon dioxide impinged with carbon dioxide free hydrogen stream vs. carbon $CO_2/CO/H_2$ stream upstream of CO2-CC section |
| 9 | Dehydration column for complete dehydration of $H_2$ (CO)/$CO_2$ stream |
| 10 | Subcritical-supercritical $CO_2$ condenser operating in supercritical pressure of carbon dioxide |
| 11 | Subcritical gas cooler(s) for carbon dioxide and gaseous hydrogen rich syngas |
| 12 | Drain of liquefied carbon dioxide entrained from the hydrogen rich syngas downstream of $CO_2$ condensation and $CO_2$ separation tank |
| 13 | Liquefied carbon dioxide and hydrogen rich syngas to $CO_2$ condensation and $CO_2$ separation tank |
| 14 | $CO_2$ condensation and $CO_2$ separation tank |
| 15 | Liquefied carbon dioxide upstream of high pressure feed pump for the First Thermodynamic Cycle for waste heat recovery, specifically for elimination of the cooling tower and chimney |
| 16 | Cooled hydrogen rich syngas below the critical point of carbon dioxide |
| 17 | Carbon dioxide free hydrogen stream vs. carbon $CO_2/CO/H_2$ stream upstream of CO2-CC section |
| 18 | Main condenser for condensation and separation of carbon dioxide |
| 19 | Auxiliary Cooling Unit for the condensation of carbon dioxide, optionally on summer season |

Figure 5A:
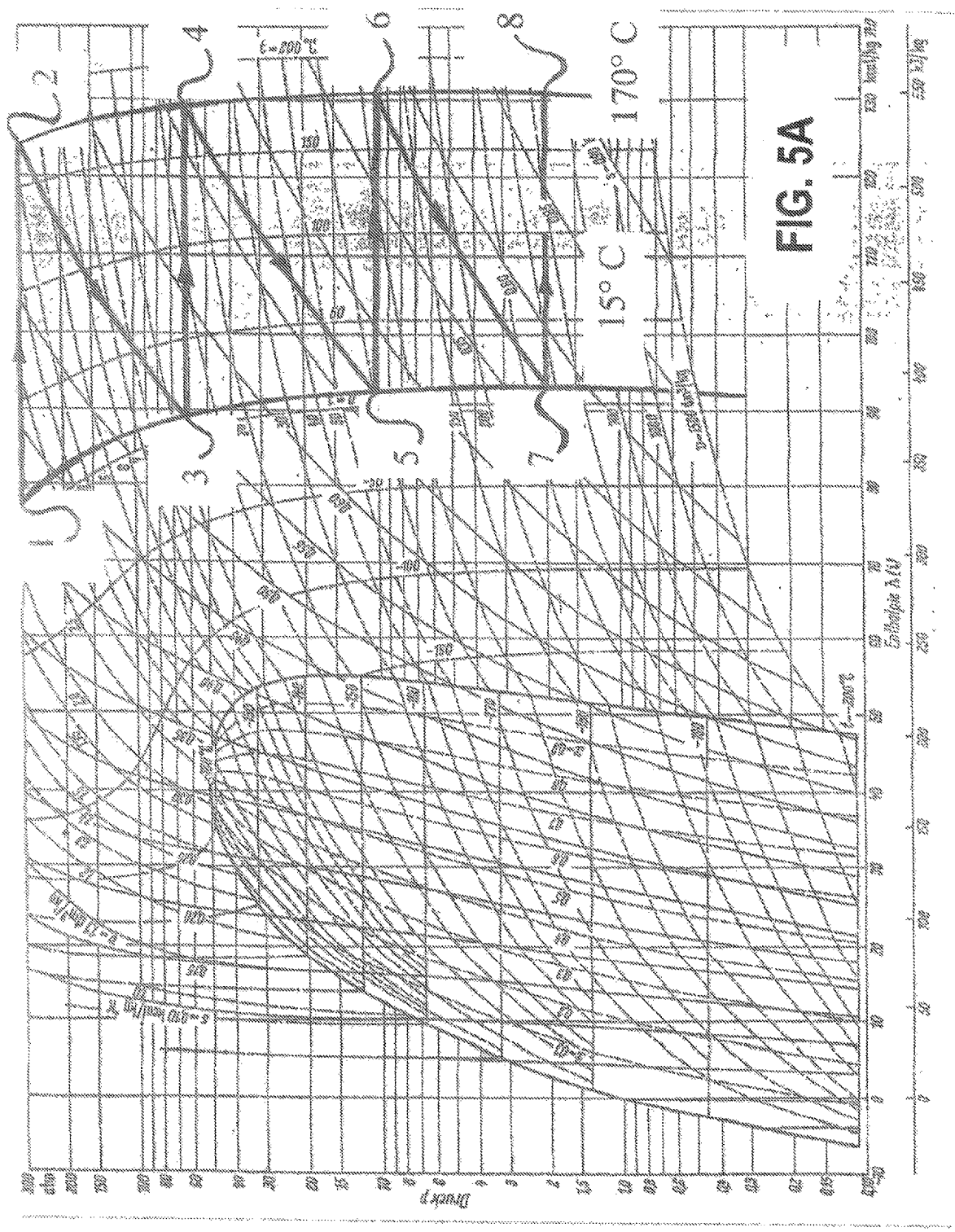
Figure 5B:
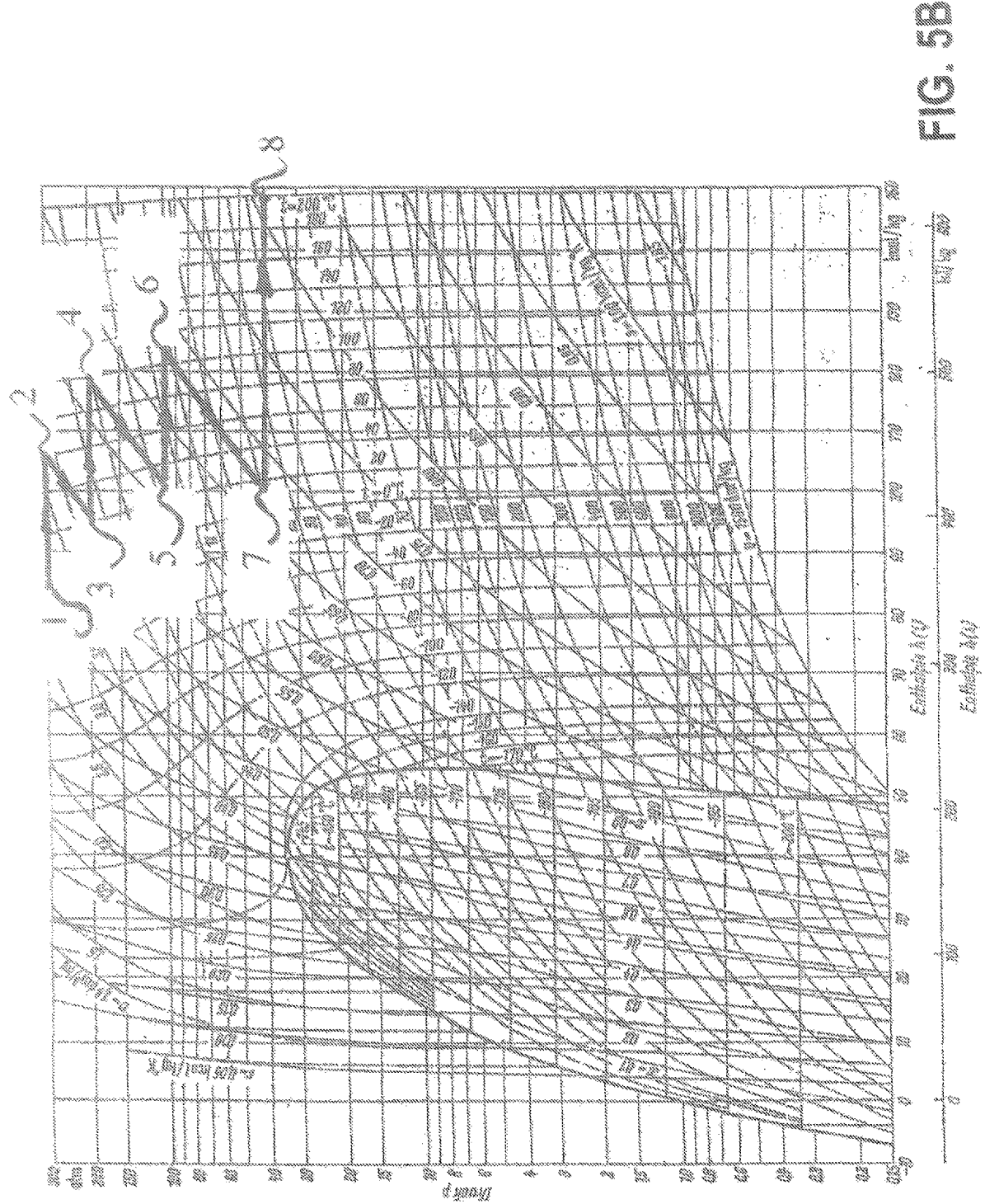

| Element | Description of the element |
|---|---|
| 20 | Export liquefied carbon dioxide, e.g. for urea production, EOR, IOR, sequestration of carbon dioxide or stored and transported as energy career (e.g. for an offsite operating PHLTE-Syngas Generator) |
| 21 | High pressure feed pump for liquefied carbon dioxide of the First Thermodynamic Cycle |
| 22 | Export high pressure liquefied carbon dioxide to the PHLTE-Syngas Generator section |
| 23 | High pressure liquefied carbon dioxide to the economizer, boiler, superheater and re-superheaters of the CO2-PG and utilization section |
| 24 | $CO_2$ economizer |
| 25 | $CO_2$ boiler (evaporator) |
| 26 | Absorber filter for removal of carbon monoxide traces upstream of the $CO_2$ super-heater, operational by any other process heat or run vs. Closed Cooling Circuit |
| 27 | $CO_2$ preheating/superheating vs. process heat upstream of $CO_2$ supraheater |
| 28 | $CO_2$ supraheater(s) operating vs. process heat or auxiliary $CO_2$ supraheater and the set of re-superheater(s) upstream of each $CO_2$ turbine section |
| 29 | Superheated $CO_2$ of the First Thermodynamic Cycle upstream of the HP section of the $CO_2$ turbine |
| 30 | HP section of the $CO_2$ turbine |
| 31 | By-pass line of HP turbine for the ramp up period |
| 32 | $CO_2$ recycle cooler |
| 33 | $CO_2$ recycle chiller upstream of the condenser tank 14 |
| 34 | Recycle liquefied $CO_2$ to condenser tank |
| 35 | $CO_2$ resuperheater |
| 36 | $CO_2$ downstream of the IP section of the $CO_2$ turbine either for export of MP gaseous $CO_2$ or upstream to resuperheater(s) of the LP section of $CO_2$ turbine |
| 37 | $CO_2$ export gas cooler (integrated in the Closed Cooling Circuit for heat recovery) |
| 38 | $CO_2$ de-superheater |
| 39 | LP gaseous $CO_2$ downstream of de-superheater for export (e.g. EOR/IOR/sequestration or seasonal underground storage) |
| 40 | IP/MP section of the $CO_2$ turbine |
| 41 | $CO_2$ resuperheater upstream of the LP section of the $CO_2$ turbine |
| 42 | LP section of the $CO_2$ turbine |
| 43 | Main LP $CO_2$ downstream of the LP section of $CO_2$ turbine to the regenerative heat exchanger and condensers, which operate predominantly vs. oxygen and $H_2$/CO stream from the HPLTE-Syngas Generator with the multistage oxygen turbine as well as vs. multistage hydrogen/carbon monoxide turbines (vide FIGS. 5A and 5B with the Appendix A). The side stream 43 can be temporarily released over the silencer to the atmosphere during an unexpected plant outage. |
| 44 | $CO_2$ generator of the CO2-PG driven by the set of the $CO_2$ turbines (or the attached syngas compressor of the MP/LP gasification, or the set of the flue gas compressors (e.g. as shown in the FIG. 2, element 7) |
| 45 | Recycle gaseous $CO_2$ from the $CO_2$ auxiliary cooling and condensation or the ACU to the $CO_2$ compressor for recirculation |
| 46 | Recycle $CO_2$ compressor |
| 47 | The element 47 for primary Direct Steam torch deleted, and represented by 54 |
| 48 | The element 48 for re-superheating Direct Steam torch deleted, and represented by 54 |
| 49 | The element 49 for subsequent re-superheating deleted, and represented by 54 |
| 50 | LP/MP purified hydrogen from the gasification process and downstream of $CO_2$ separation. The incoming purified hydrogen stream for Direct Steam generation (the stream 50 can stem from portion of the outgoing hydrogen stream 17, yet downstream of a HT/LT CO-water shift and $CO_2$ separation) |
| 51 | HP compressor for MP/LP purified hydrogen upstream of Direct Steam generator torches |
| 52 | HP purified hydrogen upstream for Direct Steam torches |
| 53 | HP purified oxygen upstream for the Direct Steam generation torches |
| 54 | This element represents two kind of torches for Direct Steam generation at high pressure/intermediary pressure and low pressure, termed HP/IP/LP Direct Steam torches:<br>(a) Primary Direct Steam generation by combustion hydrogen into an oxygen stream, or preferably combustion of oxygen into a hydrogen stream or combustion of hydrogen/oxygen at stochiometric ratio<br>(b) The torch for combustion of hydrogen and oxygen in any ratio for re-superheating of a steam stream |
| 55 | HP Direct Steam generated by subsequent re-superheating upstream of HP section of the steam turbine |
| 56 | HP section of the steam turbine |
| 57 | IP steam downstream of the HP section to re-superheating |
| 58 | Re-superheated steam upstream of the IP section of the turbine |
| 59 | IP section of the turbine |
| 60 | Not applicable |
| 61 | IP steam downstream of the IP section of the steam turbine |
| 62 | Reheat steam upstream of the LP section of the turbine |
| 63 | IP section of the steam turbine |
| 64 | Steam vapor at vacuum pressure to the condenser(s) |
| 65 | Main condenser |

| Element | Description of the element |
|---|---|
| 66 | Steam condensate with traces oxygen, or excess hydrogen of the Direct Steam generators |
| 67 | Condensate stripper for regaining of excess hydrogen |
| 67 A | Reboiler of the stripper column |
| 68 | Hydrogen rich vapor off the top section of stripper to the dephlegmator |
| 69 | Recompressor for the recovered hydrogen stream to the IP or LP torches |
| 70 | Recovered hydrogen stream to the IP or LP torches |
| 71 A | Cooler for main condensate stream upstream of hydro turbine |
| 71 B | Partial condenser (dephlegmator) upstream of recompressor |
| 72 | Hydroturbine |
| 73 | Steam condensate to polishing and recycle to the HPLTE-Syngas Generator |
| 74 | Not applicable |
| 75 | IP/LP Direct Steam generation for auxiliary boiler, running seasonally or to balance out the steam turbine at high peak |
| 76 | Not applicable |
| 77 | IP/LP steam generated to outbalance the IP/LP section of the steam turbine |
| 78-89 | Not applicable |
| 90 | Boiler feed water to the auxiliary boiler's economizer |
| 91 | Economizer of the auxiliary boiler |
| 92 | Preheated auxiliary boiler feed water |
| 93 | Auxiliary boiler run by superheated Direct Steam |
| 94 | Demister, droplet water separator of the auxiliary boiler |
| 95 | Saturated auxiliary steam to the superheater |
| 96 | Auxiliary boiler's superheater |
| 97 | Superheated steam to the auxiliary LP turbine |
| 98 | Auxiliary LP turbine running on peak time or on season, detachable from the mail shaft e.g. by hydraulic couple |
| 99 | Auxiliary boiler's vapor to the vacuum condenser |
| 100 | vacuum condenser of the auxiliary turbine |
| 101 | Condensate to condensate polishing and recycle to boiler feed water system |

Brief description of the embodiment in the FIG. 2 and the elements thereto

The FIG. 2 represent the post-combustion carbon capture and reuse of $CO_2$ illustratively for the greatest embodiment of the present process associated with the retrofitting of all currently operational plant, which are according to the Stationary Sources of GHG emissions. This group of the plants that are culprit for nearly 75% of global $CO_2$ emission can be rebuild to zero-net-carbon-emission plants. Hence this, the FIG. 2 represents the principal embodiment for retrofitting these plants illustratively only.

The FIG. 2 is intentionally designated for the retrofitting of the fossil energy coal, crude oil, natural gas fired, biomass and gas turbine power plants to the net-zero-carbon-emission. Some of the presented features in the FIG. 2 are not applicable to other Stationary Sources of $CO_2$ emitting plants like those in ammonia, methanol, iron, steel, and aluminum plants. The illustrative presentation in FIG. 2 does not restrict any other sections for retrofitting of other carbon dioxide emitting plants. The more detail description of the post-combustion carbon capture, waste heat recovery and reuse of carbon dioxide as a new fossil energy resource are extensively described in the block diagrams FIGS. 8 and 9 in the Appendix C.

| Element | Description of the element |
|---|---|
| 1 | $CO_2$ containing gas stream i.e. flue gas of fossil power plants, or any other Stationary Source of the $CO_2$ emission to the atmosphere.<br>The stream 1 represents also the $CO_2$-enriched flue gas that is obtained from the combustion section of the plant by the oxy-fueling with the oxygen, whereas the oxygen for the oxy-fueling stems from the anodic oxygen of the HPLTE-Syngas Generator specifically. |
| 2 | Flue gas hot water scrubber(s), primarily for removal of Black Carbon (during the de-sooting process) and some other pollutants e.g. the water-soluble $NO_x$ or $SO_x$ and other harmful constituents |
| 3 | $CO_2$ containing clean flue gas downstream of the hot-water scrubber |
| 4 | Booster blower/booster compressor, if needed to overcome the pressure drop |
| 5 | Cold water scrubber with by CCC-HR for Closed Cooling Circuit for waste heat recovery |
| 6 | Solid particle free $CO_2$ containing flue gas upstream stream of the compression stages |
| 7 | LP/MP/HP compressors |
| 8 | CO2-PG turbine(s) for driving the compressors by the operation of the First Thermodynamic Cycle, backed up by waste heat recovery in CO2-HR and CCC-HR with optional supraheating auxiliary heater for carbon dioxide cycle |
| 9 | Cleansed $CO_2$ and pollutant free flue gas expander turbine |
| 10 | Electric propulsion attached to the shaft of turbine-compressors during the start-up period of the plant |
| 11 | Clutch coupling (e.g. hydraulic couple) for detachment from the electric propulsion post the ramp up period |

-continued

| Element | Description of the element |
|---|---|
| 12 | Generator for additional AC power obtained from the waste energy by the operation of the First Thermodynamic Cycle |
| 13 | Clutch coupling (e.g. hydraulic couple) for attachment to the compressor-turbine machinery post the ramp up period |
| 14 | Interchanger for cooling, integrated in the CO-HR, CCC-HR with removal of all combustion water including the heat exchanger dehydration of the $CO_2$ stream |
| 15 | Separators for combustion water removal, dehydration section with discharge of pressurized condensate to the hydro turbine 16 |
| 16 | Hydroturbine for discharge of pressurized condensate |
| 17 | Generator attached to the hydro turbine |
| 18 | Combustion water discharge from the interchangers of the compression stage, partly discharged from the system, in part recycled back to flue gas scrubber tower 5 |
| 19 | Discharge of combustion water according to the analysis of most harmful constituent like Antimony, Mercury etc. |
| 20 | Recycle combustion water to flue gas scrubber tower |
| 21 | Recycle water in scrubber tower |
| 22 | Recycle water in scrubber tower |
| 23 | Recycle water in scrubber tower |
| 24 | Discharge of cold water scrubber tower to filtration of solid particles with partial recycle to the circuit of the scrubber tower |
| 25 | Scrubber bottom pump or the tower's recirculation pumps |
| 26 | Scrubber water filter |
| 27 | Filtrated combustion water obtained in the cold scrubber tower to the hot water scrubber for removal of ash, dust, soot |
| 28 | Filtered scrubber water back to cold water scrubber according to the level of solid particle (dust, ash, soot) analysis |
| 29 | Black soot water collected in the bottom of the hot water scrubber |
| 30 | Black soot water pump of the hot water scrubber |
| 31 | Cooled black water to the soot filter |
| 32 | Discharge of the black water to waste water treatment and disposal |
| 33 | Soot and dust filter |
| 34 | Cooled black water back to hot water scrubber |
| 35-39 | Not applicable |
| 40 | Compressed $CO_2$ subcritical and super critical flue gas downstream of each compressor stage, upstream of the heat exchanger of the CO2-HR and CCC-HR sections |
| 41 | Dehydrated cooled $CO_2$ containing flue gas to recompression |
| 42 | Supercritical compressed flue gas over 1070 PSI pressure to CO2-HR, final dehydration, CO2-CC and removal of the liquefied $CO_2$ by subcritical cooling of carbon dioxide containing flue gas below the 87 F. (31 Deg Centigrade) |
| 43 | Cleansed $CO_2$ and pollutant free flue gas (utmost consisting only of the remaining portion of nitrogen post oxy-fueling combustion), preheated upstream of flue gas expander turbine |
| 44 | Cleansed $CO_2$ and pollutant free flue gas back to the atmosphere |
| 45-49 | Not applicable |
| 50 | Hot flue gas heat exchanger, part of CCC-HR section |
| 51-53 | Cold tower flue gas scrubber's heat exchanger, part of CCC-HR section |
| 54 | Not applicable |

FIG. 2, A
Illustrative depiction of CCC-HR Closed Cooling Circuit with Heat Recovery

| | |
|---|---|
| 55 | Hot end of the Closed Cooling circuit with conditioned water for the heat recovery from the low temperature sources that is integrated in the CO2-HR and CO2-PG by use of liq. $CO_2$ economizer and $CO_2$ evaporator and $CO_2$ superheater of the First Thermodynamic Cycle |
| 56 | Cold end of the Closed Cooling Circuit |
| 57-59 | Not applicable |

FIG. 2, B
Illustrative depiction of $CO_2$ recovery system from internal process media

| | |
|---|---|
| 60 | $CO_2$ containing condensates of the $CO_2$ compression stages (like in $CO_2$ containing Flue Gas from the ammonia, methanol, iron, steel, and aluminum industry) to $CO_2$ recovery stripper |
| 61 | Recovered $CO_2$ back to compression stages |
| 62 | Reboiler of $CO_2$ recovery stripper |
| 63 | Circulation condensate, optionally with circulation pump |
| 64 | $CO_2$ recovery stripper |
| 65-66 | Circulating hot water, preferably superheated $CO_2$ for reboiler |
| 67 | Superheated $CO_2$ of the First Thermodynamic Cycle for running the $CO_2$ turbines of the flue gas compression machinery |
| 68 | $CO_2$ steam downstream of the $CO_2$ turbine to regenerative heat exchangers |
| 69 | $CO_2$ discharge downstream of the turbine as heat career for internal purposes (e.g. running the $CO_2$ reboiler 62) Depiction of CO2-HR portion of the First Thermodynamic Cycle illustrated |

-continued

| Element | Description of the element |
|---|---|
| | via CCC-HR Closed Cooling Circuit |
| 70 | Liquefied carbon dioxide of the First Thermodynamic Cycle for CO2-HR and CO2-PG fed to preheater (not depicted in the FIG. 2), upstream to the evaporator 71 |
| 71 | $CO_2$ evaporator integrated in the First Thermodynamic Cycle |
| 72 | Droplet separator |
| 73 | Saturated carbon dioxide to the first superheater |
| 74 | Not applicable |
| 75 | $CO_2$ superheater |
| 76 | Superheated carbon dioxide to the headers for CO2-PG section |

Brief description of the embodiment in the FIG. 3 and the elements thereto

The FIG. 3 present the process section and device for the high pressure low temperature electrochemical conversion (HPTE-Syngas Generator) of the liquefied carbon dioxide blended with purified dematerialized water to the anodic high pressure gaseous oxygen and cathodic syngas at the hydrogen-to-carbon monoxide molar ration of two. Each obtained gaseous products of the HPLTE-SG undergoes further purification down-stream of the HPLTE-SG before these products are processed to further steps.

As some final products, like jet fuel, gasoline, methanol, and ethanol requires, the cathodic syngas may be subject to adjustment in molar ratio, wherein the carbon dioxide will be separated by the same process described and recycled for reuse (vide streams 37 and 48 of FIG. 3). This is performed by high pressure LT and, in case needed, HT CO-water shift converters.

More importantly, the low temperature gaseous products are integrated in the "closing loop of the First Thermodynamic Cycle", whereas the high pressure low temperature gaseous products are employed for the closing loop of the carbon dioxide cycle down-stream of the $CO_2$-regenerative heat exchangers. This peculiarity of the present process is distinguished by multistage oxygen and syngas turbines and reheater (that is the condensing carbon dioxide at the other side of the heat exchangers). This processing allows the HPTESG products to perform the supercritical critical, and subcritical condensation of the $CO_2$ along the line of 6-7 in the thermodynamic chart, presented in the FIG. 4A. The multistage application of the oxygen and syngas in presented in the FIGS. 5A and 5B.

The obtained oxygen will be applied in part for the oxy-fueling like in the existing and/or future fossil power plants or fed to the gasifier (like the high pressure coal gasifier for the super-efficient hydrogen based fossil power plants according to the Second Thermodynamic Cycle of the present process). The other part can be exported for sale for various other applications. Most importantly, the high pressure oxygen is fed to the Direct Steam torches, wherein the oxygen is combusted with hydrogen (preferably obtained from high pressure gasification of carbonaceous material, preferably coal) for the super-efficient hydrogen based fossil power plant of near future (vide block diagram in FIG. 10).

| Element | Description of the element |
|---|---|
| 1-10 | Not applicable |
| 11 | High pressure liq. $CO_2$ from the CO2-CC section (like the stream 22 downstream of $CO_2$ high pressure pump 21 in FIG. 1) upstream of the PLTE-SG's high-pressure pump |
| 12 | Purified water upstream of the high-pressure feed pump |
| 13 | High pressure feed pump for the purified water upstream of the multi-stage mixer-cooler for high pressure water-carbon dioxide electrolyte |
| 14 | The multi-stage mixer-cooler, which is integrated in the CCC-HR for heat recovery of the blend electrolyte at the other side of the cooling coils. |
| 15 | Cooled high pressure water-carbon dioxide electrolyte upstream of the reactor PHTE-SG |
| 16 | AC current obtained from the AC generator of the CO2-PG's $CO_2$ turbine machinery (FIG. 2, element 12) |
| 16.1 | AC current generated from the high-pressure syngas from the HPLTE-SG up-stream of high-pressure water-shift converter |
| 16.2 | AC current generated from the high-pressure oxygen from the HPLTE-SG |
| 17 | AC/DC converter, if the DC power supply supported from the AC generator. The alternative supplementary DC power supply from the fuel cell or solar energy, or thermolelectric generator(s) will join to the line 18, thus by-passing the AC/DC converter (vide claims 59, 60 and 77 to 84). |
| 18 | DC power supply to the HPLTE-Syngas Generator |
| 19 | Not applicable |
| 20 | Body of the HPLTE-Syngas Generator |
| 21 | Headers for positive and negative connections of DC current to the electrodes |
| 22 | Diaphragm of the electrolysis separating cathodic chamber from the anodic chamber of the HPLTE-SG |
| 23 | Integrated cooling coils in the HPLTE-SG for keeping the operation temperature at the default temperature, preferably between 5 to ca. 25 Deg Centigrade. |
| 24 | Integrated cooling coils' headers in the HPLTE-SG |
| 25 | Anode and cathode electrodes |
| 26 | Separation plates, separating the cathodic from the anodic compartment in the lower part of the HPLTE-SG |

| Element | Description of the element |
|---|---|
| 27 | Separation plates, separating the cathodic from the anodic compartment above the level of the electrolyte in the gas phase chamber |
| 28 | Level of the electrolyte |
| 29 | Internal recirculation flow of the electrolyte according to the upstream flux of the generated gaseous products in each cathodic and anodic compartment |
| 30 | Cathodic syngas product |
| 31 | Purification column for cathodic syngas from the oxygen traces (vide process description) |
| 32 | Purified oxygen free syngas to further processing; for cooling and condensation of the $CO_2$ in the First Thermodynamic Cycle; to the HP and IP water shift converters; or to final hydrocarbon products manufacturing |
| 33 | Preheated high pressure syngas (i.e. one of the $CO_2$ condensers of the First Thermodynamic Cycle) |
| 34 | Preheated high pressure syngas blended with steam/water upstream to the next preheater |
| 34.1 | Syngas/steam stream upstream to the high-pressure CO-water-shift converter |
| 35 | High pressure CO-water-shift converter |
| 36 | Hot hydrogen enriched syngas with $CO_2$ to the converter's heat exchanger |
| 37 | Cooled hydrogen enriched or CO conditioned syngas with $CO_2$ to the CO2-CC section for removal of $CO_2$ |
| 38 | Separated liquid $CO_2$ from the hydrogen enriched or CO conditioned syngas. Stream 38 routing to $CO_2$ main condenser (FIG. 1, element 14) or upstream to the high-pressure liquid $CO_2$ pump (FIG. 1, element 21) |
| 39 | Not applicable |
| 40 | High pressure syngas preheater (i.e. one of the carbon dioxide condensers of the First Thermodynamic Cycle) upstream of first syngas expander turbine |
| 41 | Preheated/superheated syngas upstream of the syngas turbine |
| 42 | Syngas expander turbine and generator set (according to the first stage in the FIG. 4A and 5B). Other three expander turbines not depicted in the Figure (vide FIG. 5A and 5B) |
| 43 | High pressure water shift converter for high pressure processing like methanol. This water-shift converter's preheater will be impinged with pressure conditioned syngas downstream of the syngas turbine |
| 44 | Syngas cooler integrated in the CCC-HR |
| 45 | Cooled syngas upstream of steam/water injection (line 65) |
| 45.1 | Steam/hydrogen/CO gas to the water-shift converter |
| 46 | Middle pressure CO-water shift converter with steam or water interjection |
| 46.1 | Syngas preheater upstream of the water-shift-converter, syngas preheated by the exothermic reaction |
| 47 | Converted and/or conditioned CO/Hydrogen syngas to $CO_2/H_2$ stream upstream |
| 48 | Converted syngas to pure hydrogen (like for further ammonia production) and/or conditioned CO/Hydrogen syngas to carbon monoxide separation according to the CO2-CC processing |
| 49 | Recycled liquefied carbon dioxide for further internal processing, e.g. re-feeding to the HPLTE-SG |
| 50 | High pressure oxygen downstream of HPLTE-SG |
| 51 | Electric arc for conversion of the hydrogen traces entrained in the oxygen flow to water |
| 52 | Oxygen purification column for anodic oxygen from the traces of carbon dioxide entrained in the oxygen stream (vide process description) |
| 53 | High pressure purified oxygen downstream of purification column |
| 54 | High pressure purified oxygen to the preheater (like condenser of the $CO_2$ in the First Thermodynamic Cycle) and expander turbine, as described in the Appendix A. |
| 55 | High pressure oxygen preheater (i.e. one of the carbon dioxide condenser of the First Thermodynamic Cycle) |
| 56 | Superheated high pressure oxygen upstream of the first oxygen turbine (according to the first stage in the FIG. 4A and 5B) |
| 57 | The first expander turbine for oxygen, other three expander turbines are not depicted in the Figure (vide FIG. 5A and 5B) |
| 58 | Oxygen stream downstream of the first stage of the oxygen turbine upstream to the carbon dioxide condenser(s) of the First Thermodynamic Cycle |
| 59 | Not applicable |
| 60 | Purified dematerialized water for syngas and oxygen purification downstream of the HPLTE-SG |
| 61 | Discharge of the hydrogen purification column to the $CO_2$ recovery stripper (FIG. 2, B) |
| 62 | Discharge of the oxygen purification column to atmosphere and disposal |
| 63 | Not applicable |
| 64 | Not applicable |
| 65 | Steam or water injection for conditioning prior to the water-shift converter |
| 66-69 | Not applicable |
| 70 | High pressure conditioned syngas for high pressure processing like for methanol manufacturing, or pure hydrogen for Direct Steam torches (preferably during the ramp up period) |

Brief description of the embodiment in the FIGS. 4 A, 4 B, 5A, and 5B

The Appendix A outlines detail description, elaborations by use of the thermodynamic charts (FIGS. 4A, 4B, 5A, and 5B). The Appendix A provides the specifics of each two new cycle in four sub-parts, i.e.:

Elaborative description of the cycle in prolog
The characteristic features of the new cycle
The advantages of this cycle from processing and mechanical design aspects
Operation field of the First and the Second Thermodynamic Cycles Each thermodynamic chart indicates the distinctive points of operation with Roman number that are described in the context either as the Step-1 to Step-7 for the new First Thermodynamic Cycle or with (i), (ii), (iii) and (iv) for the Second Thermodynamic Cycle in itemized structure distinctively.

Specifically, the peculiarity of the First Thermodynamic Cycle with the employed regenerative heat exchangers, yet most importantly "the closing path" along the lines 6-7-1, for the supercritical, critical, and sub-critical condensation of the carbon dioxide by use of the high pressure low temperature gaseous products of the HPLTE-Syngas Generator employed multiple of times (FIGS. 5A and 5B) are delineated in the Appendix A.

Appendix C: Further elaboration for the general inventive concept of the present invention with it's three fundamental features (I), (II) and (III) that addresses the solution to the Stationary Sources of $CO_2$ emission in five principal embodiments according to the FIGS. 6 to 10

This appendix provides the five principal embodiments of the invention presented figuratively by the FIGS. 6, 7, 8, 9 and 10 with the list of the process sections related thereto, without limitation to other fields of application. The elements of each block diagram v.i. are listed in this appendix that outlines the elements of each principal embodiment.

The Appendix C performs the short and detail description of the five principal embodiments of the present process invention, wherein five block diagrams present the five field of application. The FIGS. 6, 7, 8. and 9 are presenting the pre-combustion and pot-combustion carbon capture by $CO_2$ liquefaction, $CO_2$ utilization via First Thermodynamic Cycle, and $CO_2$ electrolysis via HPLTE-SG to oxygen and syngas. These four block diagrams present the application of this process for existing fossil energy plants, referred to Stationary Source of the $CO_2$ emission.

Figure 9:
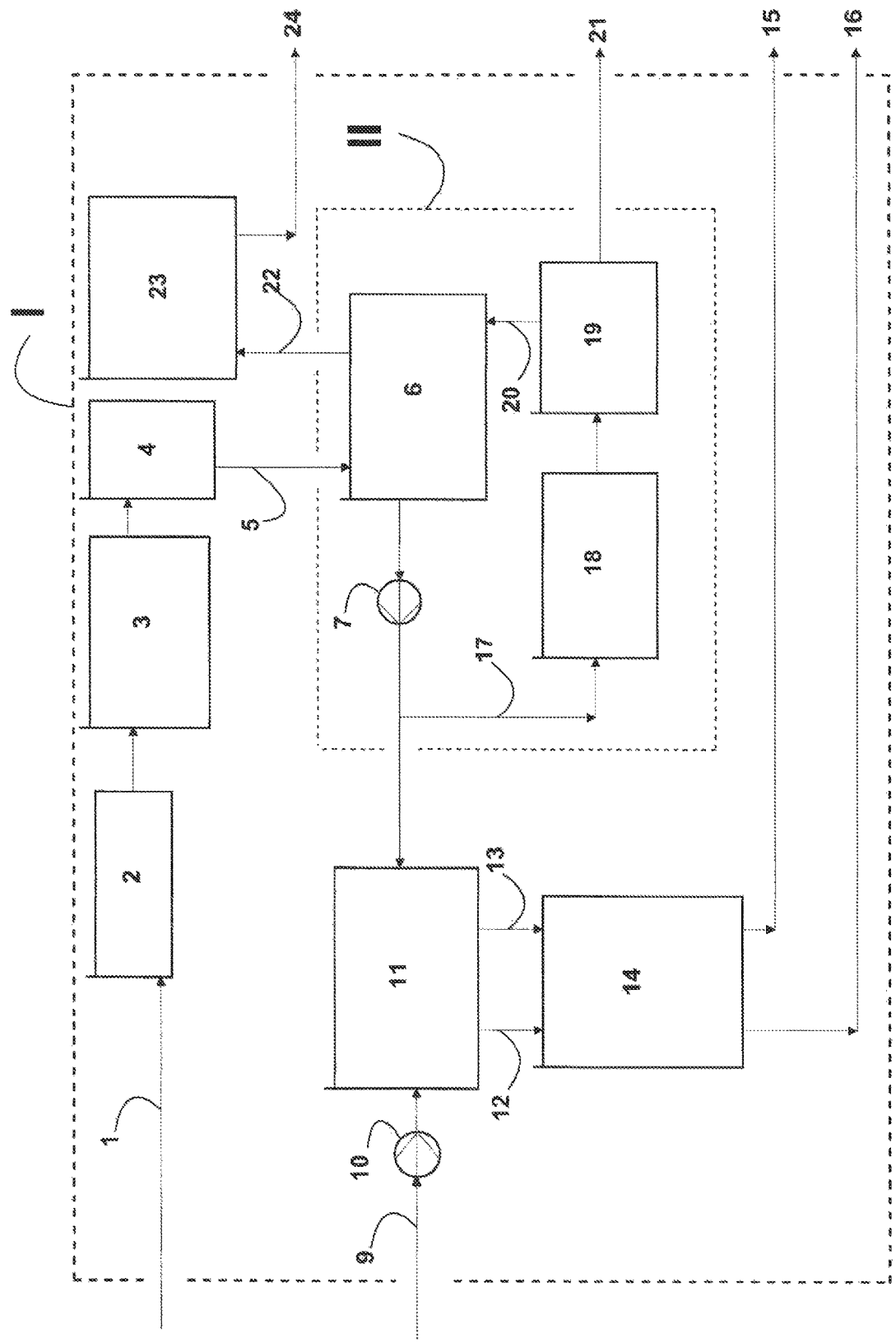
Figure 10:
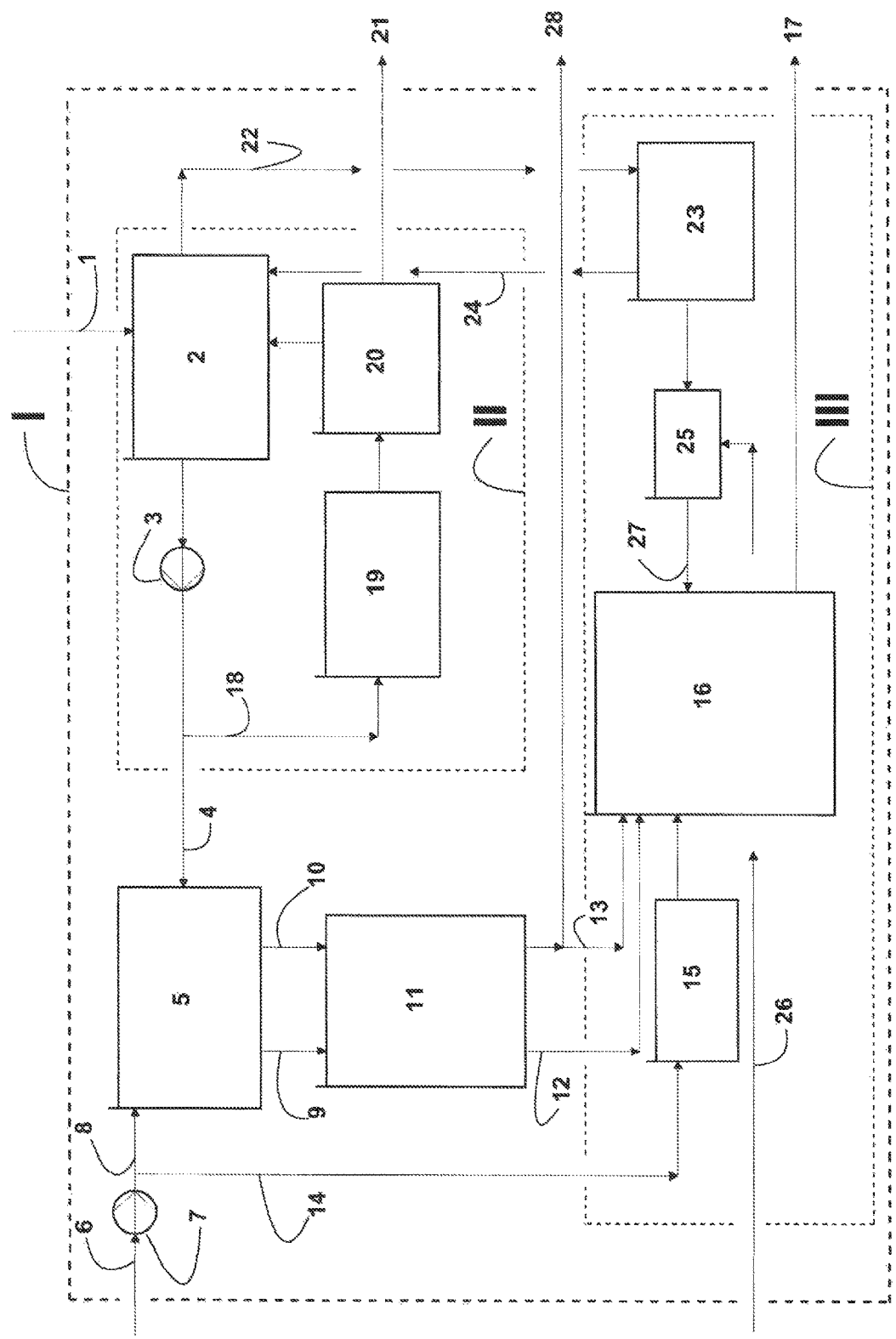

The FIG. 10 pertains to the application of the present process for construction of super-efficient hydrogen-based fossil power generation in future. The Appendix C also provides a list of the individual elements depicted in each FIGS. 6 to 10.

1. Embodiment for of the Invention Associated with the Pre-Combustion Carbon Capture from MP/LP Gasification Presented in FIG. 6

This embodiment presents the operation of the process invention's fundamental principals (I) and (II) applied for the pre-combustion carbon dioxide capture (FIG. 1) out of syngas from the middle pressure MP and low pressure LP gasification of coal, oil, natural gas, biomass and other carbonaceous feedstocks 1. The process steps for gas clean up, COS hydrolysis, row gas treatment 2, water shift gas converter 3, gas cooling and Mercury removal 4, AGR acid gas removal for $H_2S$ only 5, and sulfur recovery 25 are applied according to state-of-the-art processing.

Further processing of LP/MP syngas laden with $CO_2$ below the critical pressure of carbon dioxide 6 includes according to the present invention comprises the sysngas in the boundary limit I the syngas compression 7, wherein the heat recovery of the First Thermodynamic Cycle (FIG. 4A) CO2-HR in integrated. The $CO_2$ laden syngas will be proceeded to the $CO_2$ condensation and regenerative CO2-HR in 8, where the liquid $CO_2$ will be obtained. The The high pressure anhydrous $CO_2$ pump 9 supplies the First Thermodynamic Cycle, line 19 and the HPLTE-SG 10.

The implementation of the First Thermodynamic Cycle within I includes the $CO_2$ waste heat and process heat recovery CO2-HR in 20, the generation of super heated-supraheated $CO_2$ upstream of the $CO_2$ turbine in the section 21. The $CO_2$ stream downstream of the $CO_2$ turbine 22 is directed to CO2-HR and CO2-CC to recycle back (make up $CO_2$) to the 8 in the First Thermodynamic Cycle, whereas the generated AC power is dispatched either for back up of HPLTE-SG or to the grid 23.

The process steps in connection to the equipment and processing related to the high Pressure Low Temperature Electrochemical Syngas generator HPLTE-SG 13 comprises the high pressure anhydrous carbon dioxide 10 as well as purified water 11 and the high pressure water pump 12, which feed the HPLTE-SG 13 (including the elements of the FIG. 3). The HPLTE-SG 13 delivers the HP cathodic syngas 14 and the anodic HP oxygen 15 to gas purifications and power generation with AC/DC Converter in 16 (further detail in FIG. 3), wherein the pure oxygen 17 and $CO/2H_2$ 18 are exported for various manufacturing and/or power generation (e.g. FIG. 10).

The HPLTE-SG 13 delivers the HP cathodic syngas $CO/2H_2$ 14 and the anodic oxygen 15 at low temperature, which are then integrated in the multi stage syngas and oxygen turbines with intercoolers at one side of heat exchangers (FIGS. 5A and 5B which serve as condensing media for the $CO_2$ cycle at the other side of the heat exchangers). The unit 16 includes also the Ancillary Power Generation (FIG. 3) with AC/DC Converter for backup power generation for the HPLTE-SG operation.

---

FIG. 6

Title: Embodiment of the invention associated with the pre-combustion carbon capture (FIG. 1) from MP/LP gasification I  Boundary line of present invention in the embodiment for reuse of $CO_2$ from partial oxidization process i.e. gasification of coal, oil, NG and other hydrocarbons
II Boundary line of the present invention associated with the First Thermodynamic Cycle via FIG. 4A with the elements 7, 8, 9, 19, 20, 21, 22, 23, 24 and with the peculiar connections to the oxygen and syngas heat recovery power generation via FIGS. 5A and 5B Elements of the FIG. 6

1 IP intermediary pressure/LP low pressure syngas (from coal/oil/NG/biomass) downstream of gasification reactor
2 Gas clean-up, COS hydrolysis, row gas treatment
3 HT/LT Water shift gas convertors, i.e. total CO conversion (e.g. for $NH_3$ synthesis) or partial CO conversion e.g. for gasoline, methanol, ethanol, SNG, etc.
4 Gas cooling for Mercury removal
5 AGR for sulfur ($H_2S$) removal only
6 Syngas consisting of $H_2/CO_2$ (optionally $H_2/CO_2/CO$) with the syngas pressure below the critical pressure of $CO_2$
7 Syngas compression with CO2-HR, ($CO_2$ Heat Recovery Section)
8 Syngas cooling by CO2-CC ($CO_2$ Cooling and Condensation with the Regenerative CO2-HR)
9 Anhydrous CO2 high pressure pump
10 Anhydrous $CO_2$ for reuse
11 Purified water
12 High pressure water pump

FIG. 6 -continued

13 Electrochemical CO₂ conversion with water by HPLTE-SG, the High Pressure Low Temperature Electrochemical Syngas Generator (FIG. 3)
14 Cathodic products, i.e. chemically pure syngas in stochiometric composition of CO/2H₂ to the ancillary power generation
15 Anodic product, the chemically pure oxygen to the ancillary power generation
16 Ancillary Power Supply, i.e. two sets of syngas and oxygen turbine, each with generator and intercoolers/reheaters heat exchanger for heat recovery, supplying to the AC/DC convertor for DC backup power of HPLTE-SG interlinked with CO2-HR and CO2-PG
17 Export anodic oxygen product at HP/IP/LP pressure for various purposes e.g. oxy-fueling, oxygen supply to the gasifier, oxidation processes or to dispatch e.g. by bottling and shipment
18 Cathode products, the chemically pure syngas CO/2H₂ at HP/IP/LP for number of final products e.g. gasoline, SNG, ethanol, methanol, ammonia, jet fuel, kerosene, fertilizer, plastics, consumer products
19 Anhydrous CO₂ for CO2-HR & CO2-PG in the First Thermodynamic Cycle
20 CO₂ waste heat and process heat recovery system of CO2-HR
21 CO₂ turbine and generator CO2-PG for power generation via the First Thermodynamic Cycle, either for backup to HPLTE-SG or export of AC power to the grid
22 Recycle CO₂ of the First Thermodynamic Cycle downstream of the CO₂ turbine to CO2-CC, intercoolers of HPLTE-SG (FIGS. 5A and 5B)
23 Additional electricity for dispatch
24 CO₂ free H₂-stream (optionally H₂/CO) at IP/LP pressure for internal use e.g. reheating of intermediary streams (or optionally for export to adjacent site e.g. for manufacturing plastics, gasoline, etc.)
25 Claus process for sulfur recovery, sulfur purification
26 Export sulfur to storage, shipment e.g. for rubber industry, pesticide manufacturing, sulfuric acid manufacture, sulfuric fertilizer etc.

2. Embodiment of the Invention Associated with the Pre-Combustion Carbon Capture from HP-Gasification Presented in FIG. 7

This embodiment comprises the operation of the process invention's fundamental principals (I) and (II) applied for the pre-combustion carbon capture from HP gasification, thus the syngas compression of the previous embodiment (FIG. 6, element 7) is not implemented. The other processing stages are the same steps, though designed at higher pressure level.

Figure 7:
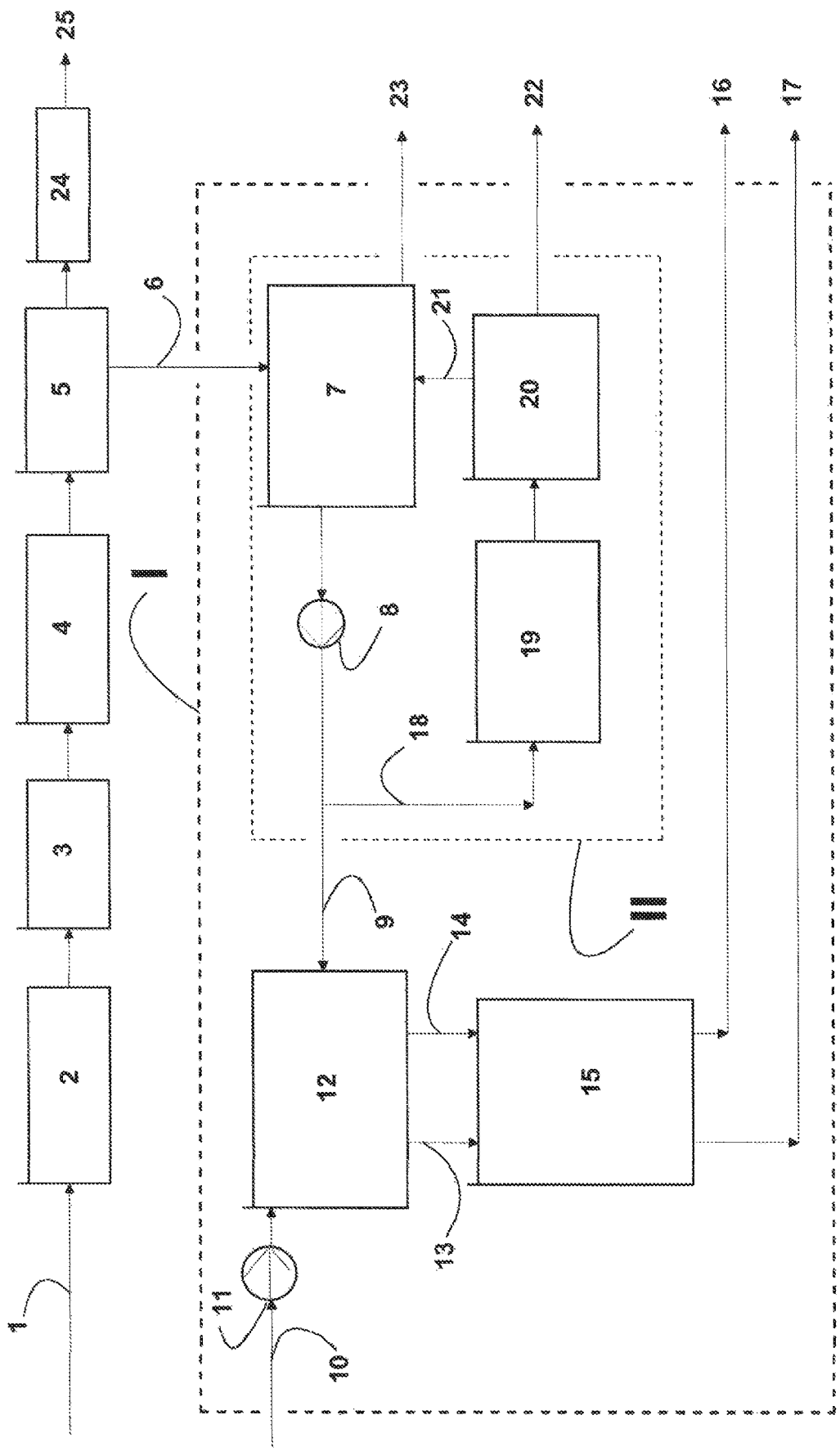

The embodiment in FIG. 7 presents pre-combustion carbon dioxide capture (FIG. 1) out of syngas from the middle pressure MP and low pressure LP gasification of coal, oil, natural gas, biomass and other carbonaceous feedstocks 1. The process steps for gas clean up, COS hydrolysis, row gas treatment 2, water shift gas converter 3, gas cooling and Mercury removal 4, AGR acid gas removal for H₂S only 5, and sulfur recovery 25 are applied according to state-of-the-art processing.

This embodiment considers HP syngas laden with CO₂ above the critical pressure of carbon dioxide 1 in the boundary limit I, wherein the heat recovery of the First Thermodynamic Cycle (FIG. 4A) CO2-HR in integrated in 7, 8, 18, 19, 20 and 22. The CO₂ laden syngas will be proceeded to the CO₂ condensation and regenerative CO2-HR in 7, wherein the liquid CO₂ will be obtained. The The high pressure anhydrous CO₂ pump 8 supplies the First Thermodynamic Cycle to replenish CO₂, line 18 and the HPLTE-SG 9.

The implementation of the First thermodynamic Cycle within I includes the CO₂ waste heat and process heat recovery CO2-HR in 19 with the generation of super heated-supraheated CO₂ upstream of the CO₂ turbine in the section 20. The CO₂ stream downstream of the CO₂ turbine in 21 is directed to CO2-HR and CO2-CC to recycle back to the 7 in the First Thermodynamic Cycle, whereas the generated AC power is dispatched either for back up of HPLTE-SG or to the grid 23.

The process steps in connection to the equipment and processing related to the high Pressure Low Temperature Electrochemical Syngas generator HPLTE-SG 12 comprises the high pressure anhydrous carbon dioxide 8 as well as purified water 10 and the high pressure water pump 11, which feed the HPLTE-SG 12 (including the elements of the FIG. 3). The HPLTE-SG 12 delivers the HP cathodic syngas 13 and the anodic HP oxygen 14 to gas purifications and power generation with AC/DC Converter in 15 (further detail in FIG. 3), wherein the pure oxygen 16 and CO/2H₂ 17 are exported for various manufacturing and/or power generation (e.g. FIG. 10).

The HPLTE-SG 12 delivers the HP cathodic syngas CO/2H₂ 13 and the anodic oxygen 14 at low temperature, which are then integrated in the multi stage syngas and oxygen turbines with intercoolers at one side of heat exchangers (FIGS. 5A and 5B which serve as condensing media for the CO₂ cycle at the other side of the heat exchangers). The unit 15 includes also the Ancillary Power Generation (FIG. 3) with AC/DC Converter for backup power generation for the HPLTE-SG operation.

FIG. 7

Title: Embodiment of the invention associated with the pre-combustion carbon capture (FIG. 1) from HP gasification I Boundary line of present invention in the embodiment for reuse of CO₂ from partial oxidization process i.e. gasification of coal, oil, NG and other hydrocarbons
II Boundary line of the present invention associated with the First Thermodynamic Cycle via FIG. 4A with the elements 7, 8, 9, 19, 20, 21, 22, 23, 24 with the peculiar connections to the oxygen and syngas hear recovery via FIGS. 5A and 5B Elements of the FIG. 7

1 High pressure syngas (from coal/oil/NG/biomass) downstream of HP gasification reactor
2 Gas clean-up, COS hydrolysis, row gas treatment
3 HT/LT Water shift gas convertors, i.e. total CO conversion (e.g. for NH₃ synthesis) or partial CO conversion e.g. for gasoline, methanol, ethanol, SNG, etc.
4 Gas cooling and Mercury removal
5 AGR for sulfur (H₂S) removal only
6 Syngas consisting of H₂/CO₂ (optionally H₂/CO₂/CO) with the syngas pressure below the critical pressure of CO₂
7 Syngas cooling by CO2-CC (CO₂ Cooling and Condensation with the Regenerative CO2-HR)
8 Anhydrous CO₂ high pressure pump
9 Anhydrous CO₂ for reuse
10 Purified water
11 High pressure water pump
12 Electrochemical CO₂ Conversion with water by HPLTE-SG, the High Pressure Low Temperature Electrochemical Syngas Generator (FIG. 3)
13 Cathodic products, i.e. chemically pure syngas in stochiometric composition of CO/2H₂ to the ancillary power generation
14 Anodic product, the chemically pure oxygen to the ancillary power generation
15 Ancillary Power Supply, i.e. two sets of syngas & oxygen turbine, each with generator and intercoolers/reheaters heat exchanger for heat recovery, power supply to the AC/DC convertor for DC backup power of HPLTE-SG
16 Export anodic oxygen product at HP/IP/LP pressure for various purposes e.g. oxy-fueling, oxygen supply to gasifier, oxidation processes or to dispatch e.g. by bottling and shipment
17 Cathode products, the chemically pure syngas CO/2H₂ at HP/IP/LP for number of final products e.g. gasoline, SNG, ethanol, methanol, ammonia, jet fuel, kerosene, fertilizer, plastics, consumer products

FIG. 7

18 Anhydrous $CO_2$ for CO2-HR and CO2-PG
19 $CO_2$ waste heat and process heat recovery system by CO2-HR section of the First Thermodynamic Cycle
20 $CO_2$ turbines and generator CO2-PG for power generation, either for backup to HPLTE-SG or for export of AC power to the grid
21 Recycle $CO_2$ of the First Thermodynamic Cycle downstream of the $CO_2$ turbine to CO2-CC, intercoolers of HPLTE-SG (FIGS. 5A and 5B)
22 Additional electricity for dispatch
23 $CO_2$ free $H_2$/(optionally $H_2$/CO) at IP/LP pressure for internal use e.g. reheating of intermediary streams or export to adjacent site e.g. for manufacturing plastics, gasoline, etc.
24 Claus process for sulfur recovery and sulfur purification
25 Export sulfur storage, shipment e.g. for rubber industry, pesticide manufacturing, sulfuric acid manufacture, sulfuric fertilizer etc.

3. Embodiment of the Invention Associated with the Post-Combustion Carbon Capture of the Flue Gas of Power Plants According to FIG. 8

This embodiment demonstrates the application of the two fundamental principals (I) and (II) for post-combustion carbon capture from the flue gas of fossil power plants, i.e. coal, oil, natural gas fired as well as gas turbine single cycle and combined cycle power plants and the recovery Boiler of pulp and paper downstream of the electrostatic particle precipitator, upstream of the chimney 1 (details in FIG. 2). The flue gas passes the flue gas cooling, heat recovery 2, then the scrubbing unit 3, wherein the harmful constituents e.g. soot, Mercury, Antimon, particle pollutions shall be removed 4. The flue gas passes a multi stage compression stage 5 (attached to the shaft of the flue gas expander turbine 26) with intercoolers interconnected with the CO2-HR section of the First Thermodynamic Cycle as described v.s. in (I).

The pressurized flue gas above the critical point of $CO_2$ passes through the dehydration unit 7, wherein the remaining hurmful constituents and water vapour are removed according to the state-of-the-art processing. The dry flue gas 8 can be then directed to the two new sections of this process invention for the First Thermodynamic Cycle outlined in the boundary limit I that comprises flue gas cooling and condensation CO2-CC, regenerative CO2-HR 9 where the anhydrous $CO_2$ is obtained upstream of the $CO_2$ high pressure pump 10. The high pressure liquid $CO_2$ stream 10 is forwarded to the section for HPLTE-SG 11 while the stream 20 supplies the make up $CO_2$ for the First Thermodynamic Cycle.

The high pressure anhydrous carbon dioxide 11 feeds the HPLTE-SG 14 from one side, while the purified water 12 feeds the HPLTE-SG with the high pressure water pump 13 from the other line. The HPLTE-SG 14 delivers the HP cathodic syngas $CO/2H_2$ 15 and the anodic oxygen 16 at low temperature, which are then integrated in the multi stage syngas and oxygen turbines with intercoolers at one side of heat exchangers (FIGS. 5A and 5B which serve as condensing media for the $CO_2$ cycle at the other side of the heat exchangers). The unit 17 includes also the Ancillary Power Generation (FIG. 3) with AC/DC Converter for backup power generation for the HPLTE-SG operation.

The cleansed decarbonized HP flue gas 25 is preheated by harnessing process waste heat and heat recovery of the intercoolers of the flue gas compressor. The preheated cleansed decarbonized HP flue gas 25 drives the flue gas expander turbine (that is attached to the shaft of the flue gas compressor) before being released to the atmosphere 27.

FIG. 8

Title: Embodiment of the invention associated with the post-combustion carbon capture of the Flue Gas of power plants I Boundary line of the present invention in the embodiment for $CO_2$ reuse from partial oxidization processes i.e. gasification of coal, oil, NG and other hydrocarbons
II Boundary line of the present invention associated with the First Thermodynamic Cycle via FIG. 4A with the elements 7, 8, 9, 19, 20, 21, 22, 23, 24 with the peculiar connections to oxygen and syngas hear recovery via FIGS. 5A and 5B

Figure 8:
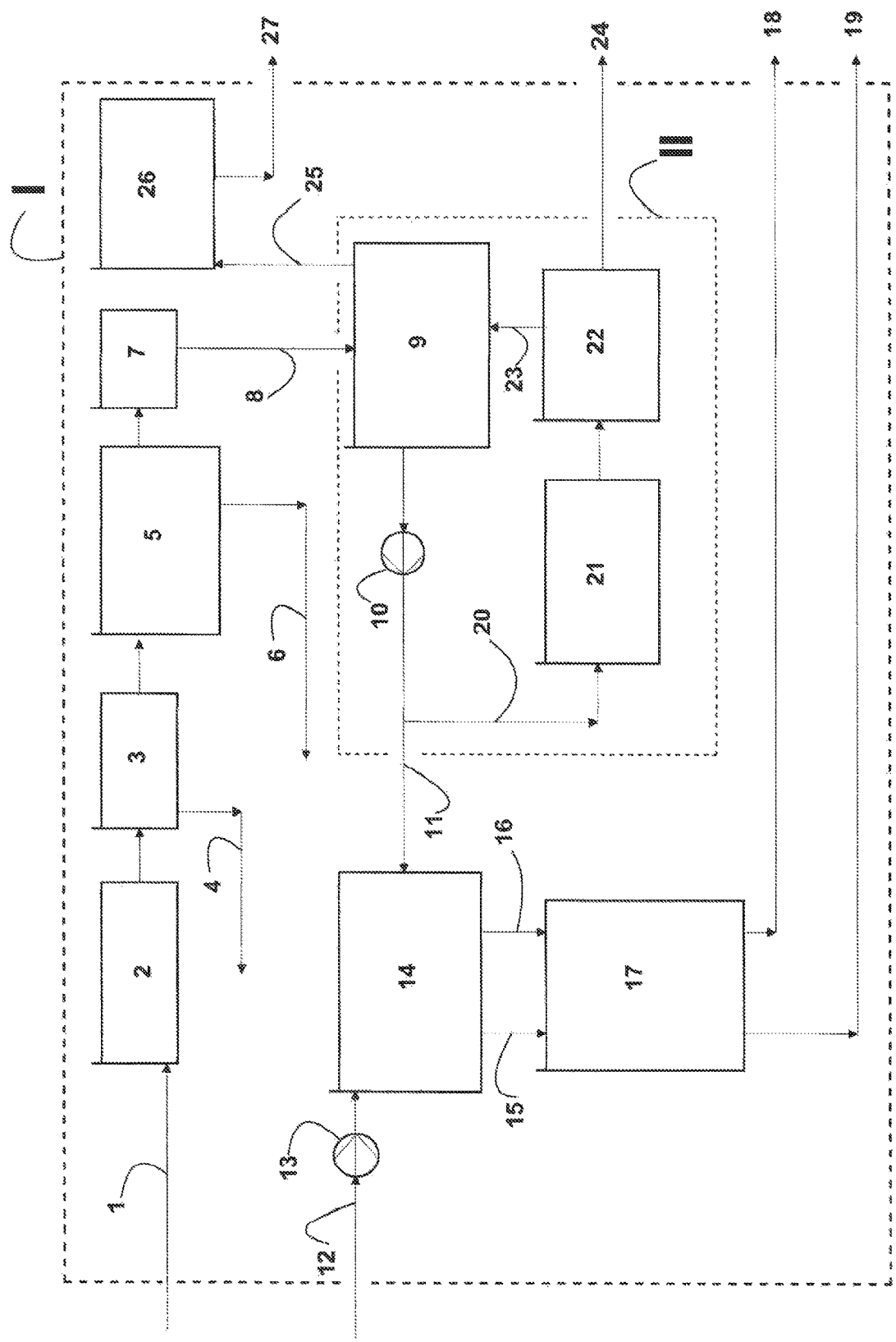

Elements of the FIG. 8

1 Flue Gas from coal/oil/NG fired fossil power plants or gas turbine single cycle or combined cycle or Recovery Boiler of pulp & paper, downstream of electrostatic particle precipitator, upstream of chimney
2 Flue gas cooling and waste heat recovery
3 Flue gas LP pressure scrubbing (FIG. 2)
4 Removal of harmful particle constituent e.g. soot, particle pollution
5 Flue gas compression and waste heat recovery condensate removal
6 Removal of harmful soluble constituent e.g. $SO_x$, $NO_x$, Mercury, Antimony, etc.
7 Flue gas dehydration
8 Dry flue gas laden with $CO_2$, $N_2$, residual $O_2$
9 Syngas cooling by CO2-CC ($CO_2$ Cooling and Condensation with the Regenerative CO2-HR)
10 Anhydrous $CO_2$ high pressure pump
11 Anhydrous $CO_2$ for reuse
12 Purified water
13 High pressure water pump
14 Electrochemical $CO_2$ Conversion with water with HPLTE-SG, the High Pressure Low Temperature Electrochemical Syngas Generator (FIG. 3)
15 Cathodic products, i.e. chemically pure stochiometric composition of $CO/2H_2$ to ancillary power generation
16 Anodic product the chemically pure oxygen to ancillary power generation
17 Ancillary Power Supply, i.e. two sets of syngas and oxygen turbine, each with generator and intercoolers/reheaters heat exchanger for heat recovery, power supply to the AC/DC convertor for DC backup power of the HPLTE-SG
18 Export anodic oxygen product at HP/IP/LP pressure for various purposes e.g. oxy-fueling, oxygen supply to gasifier, oxidation processes or to dispatch e.g. by bottling and shipment
19 Cathodic products, the chemically pure syngas $CO/2H_2$ at HP/IP/LP for number of final products e.g. gasoline, SNG, ethanol, methanol, ammonia, jet fuel, kerosene, fertilizer, plastics, consumer products
20 Anhydrous $CO_2$ for CO2-HR and CO2-PG
21 $CO_2$ waste heat and process heat recovery system CO2-HR
22 $CO_2$ turbines and generator CO2-PG for power generation, either for backup to HPLTE-SG or for export of AC current to the grid
23 Recycle $CO_2$ of the First Thermodynamic Cycle downstream of the $CO_2$ turbine to CO2-CC, intercoolers of HPLTE-SG (FIGS. 5A and 5B)
24 Additional electricity to dispatch
25 Preheated HP/MP cleansed $CO_2$ free tail gas upstream of tail gas expander
26 Tail gas expander turbine for power supply, or for driving of the flue gas compressor
27 Cleansed flue gas to atmosphere ($N_2$ and residue of $O_2$)

4. The Embodiment of the Invention Associated with the Post-Combustion Carbon Capture of the Stationary Flue Gas Other than Power Plants According to FIG. 9

This block diagram in FIG. 9 pertains to the embodiment of this process invention for post-capture carbon from Stationary Sources of $CO_2$ emission other than fossil power plants, i.e. from refinery processes, methanol, ammonia plants, $CO_2$ containing gaseous streams from aluminum, steel and geothermal sources, collectively termed Flue Gas 1. The two fundamental principals of the invention, (I) the First Thermodynamic Cycle with 6, 7, 17, 18, 19, 20 and 21. The second fundamental principal (II) is depicted with the elements 9, 10, 11, 12, 13, 14, 15 and 16 (the detail of this sections are presented in FIG. 2, FIG. 4A).

The Flu Gas 1 undergoes the section for cooling and waste heat recovery by CO2-HR in 2 first. The compression of the Flue Gas with integrated CO2-HR interlinked with the intercoolers of the compressor 3, before the pressurized Flue Gas will be dehydrated 4, wherein the traces of water and other impurities are removed from the Flue Gas. Downstream of the dehydration unit 4, the CO2-CC with regenerative CO2-HR 6 will be carried out, whence the liquid carbon dioxide will be obtained. The $CO_2$ high pressure pump 7 feeds the HPLTE-SG reuse 8 and recycle liquid carbon dioxide 17 back to the First Thermodynamic Cycle. The purified water 9 and HP water pump 10 feeds the other line to the HPLTE-SG 11 (The details of this section is presented in FIGS. 3, 5A and 5B).

The HPLTE-SG 11 delivers HP anodic oxygen 13 and HP syngas $CO/2H_2$ in 14 for Ancillary Power Supply 14. This part of HPLTE-SG delivers AC current that is converted to DC by AC/DC converter for backing up the electrolysis. The multi-stage oxygen turbine, syngas turbine and generator for the AC power. The reheater heat exchangers for the turbines will be impinged of one side with the oxygen and syngas from HPLTE-SG 11, while the oxygen and syngas heat exchangers at the other side serve as condensers of CO2-CC for the $CO_2$ condensation from the First Thermodynamic Cycle. The IP/LP anodic oxygen 15 are delivered for further processing e.g. oxy-fueling application and HP/IP syngas $CO/2H_2$ 16 transferred for the adjacent plant for gasoline, methanol, ethanol, ammonia, SNG, kerosine, fertilizer or other manufacturing processes.

| FIG. 9 |
|---|
| Title: Embodiment of the invention for $CO_2$ containing flue gas other than from fossil power plants, generically referred to as Flue Gas (FIG. 2) |

I Boundary line of the present invention in the embodiment for reuse of $CO_2$ from partial oxidization process i.e. gasification of coal, oil, NG and other hydrocarbons
II Boundary line of the present invention associated with the First Thermodynamic Cycle via FIG. 4A with the elements 7, 8, 9, 19, 20, 21, 22, 23, 24 with the peculiar connections to oxygen and syngas hear recovery via FIGS. 5A and 5B

| Elements of the FIG. 9 |
|---|

1 Stationary $CO_2$ off gas streams referred to Flue Gas, clean $CO_2$ stream or $CO_2$ containing gaseous off gas streams from chemical plants (e.g. ammonia, methanol, ethanol, refinery plants of oil & gas, natural gas treatment units $CO_2$ containing gaseous stream (e.g. steel, aluminum, geothermal sources)
2 Flue Gas cooling and waste heat recovery
3 Flue Gas compression and waste heat recovery condensate removal
4 Flue Gas dehydration and pre-treatment
5 Dry Flue Gas laden with $CO_2$, $N_2$ and excess oxygen
6 Syngas Cooling ($CO_2$ condensation CO2-CC and regenerative CO2-HR)
7 Anhydrous $CO_2$ high pressure pump
8 Anhydrous $CO_2$ for reuse
9 Purified water
10 High pressure water pump
11 Electrochemical $CO_2$ Conversion with water with HPLTE-SG, the High Pressure Low Temperature Electrochemical Syngas Generator (FIG. 3)
12 Cathodic products, i.e. chemically pure syngas in stochiometric composition of $CO/2H_2$ to the ancillary power generation
13 Anodic product, the chemically pure oxygen to the ancillary power generation
14 Ancillary Power Supply, i.e. two sets of syngas and oxygen turbine, each with generator and intercoolers/reheaters heat exchanger for heat recovery, power supply to the AC/DC convertor for DC backup power of the HPLTE-SG
15 Export anodic oxygen product at HP/IP/LP pressure for various purposes e.g. oxy-fueling, oxygen supply to gasifier, oxidation processes or to dispatch e.g. by bottling and shipment
16 Cathode products, the chemically pure syngas $CO/2H_2$ at HP/IP/LP for number of final products e.g. gasoline, SNG, ethanol, methanol, ammonia, jet fuel, kerosene, fertilizer, plastics, consumer products
17 Anhydrous $CO_2$ for CO2-HR and CO2-PG
18 $CO_2$ waste heat and process heat recovery system CO2-HR
19 $CO_2$ turbines and generator CO2-PG for power generation, either for backup to the HPLTE-SG or for export of AC current to the grid
20 Recycle $CO_2$ of the First Thermodynamic Cycle downstream of the $CO_2$ turbine to CO2-CC, intercoolers of HPLTE-SG (FIGS. 5A and 5B)
21 Additional electricity to dispatch
22 HP/MP cleansed $CO_2$ free tail gas, preheated upstream of tail gas expander
23 Tail gas expander turbine for power supply, or for driving of the flue gas compressor
24 Cleansed flue gas to atmosphere ($N_2$ and residue of $O_2$)

5. FIG. 10, Embodiment of the Invention for Super-Efficient Hydrogen Based Fossil Power Generation Associated with the Pre-Combustion Carbon Capture and Reuse of Carbon Dioxide from HP-Gasification The block diagram in FIG. 10 presents the acme of this process invention wherein all three fundamental principles, i.e. (I) the First Thermodynamic Cycle; (II) the HPLTE-SG and (Ill) the Second Thermodynamic Cycle are employed with all its specific features, vide FIGS. 1, 3, 4A, 4B, 5A and 5 B. Similar to the other block diagrams, the boundary lines for the First and Second Thermodynamic Cycle are outlined by II and Ill, whereas the remaining part within the entire boundary line I represents the HPLTE-SG including the peripheral units for Ancillary Power Generation, oxygen and syngas turbines, oxygen and syngas reheater heat exchangers as well the AC/DC Converter (details in FIG. 3).

This embodiment leads to super-efficient hydrogen based fossil power and chemical generation wherein the thermal efficiency for power generation reaches out to 85% to around 90% (depending on the location of the plant and the season) while Zero-Carbon Emission can be achieved by reuse of captured carbon dioxide as a new fossil energy resource. The average costs of electricity generated by means of fossil energy is lowered to over 30% to 35% compared with the electricity generated by the gas turbine combined cycle.

The embodiment for super-efficient fossil power and chemicals stands on the grounds of syngas $CO/H_2/CO_2$ generated by high pressure gasification of carbonaceous feedstock like crude oil, natural gas, biomass, predominantly coal served as the primary resource that is indicated in FIG. 10 by the stream 1.

It is proposed that the cleansed dehydrated syngas 1 in this embodiment has already undergone the processing steps for syngas cooling, removal of entrained slag particles, removal of harmful constituents like Antimony, Mercury before AGR for sulfur removal which has been described in FIG. 7, elements 2, 3, 4, 5 and 6.

The $CO_2$ containing syngas 1 passes to CO2-CC, with regenerative CO2-HR 2, wherefrom the anhydrous carbon dioxide will be obtained and discharged to the Main $CO_2$ Condenser tank (like in the other block diagrams, the other liquid $CO_2$ from the First Thermodynamic Cycle downstream of its $CO_2$ Condensers (which are the reheating heat exchangers of the (HPLTE-SG at the other side). The anhydrous $CO_2$ forwarded by the $CO_2$ HP pump(s) 3 supplies the First Thermodynamic Cycle 18 as well as via stream 4 the HPLTE-SG 5.

The purified water 6, is to be supplied by the HP water pump 7 feeds the HPLTE-SG via line 8 as well the Second Thermodynamic Cycle via line 14 for jacket cooling of the Direct Steam torches, water injections for the primary HP Direct Steam injections, as well as to the Direct Steam torches for reheating and re-superheating of steam upstream of each section of the steam turbine, all indicated v.i. with 15 and 16.

The HPLTE-SG 5 delivers the HP anodic oxygen 9 and the HP cathodic syngas 10 first for further harnessing used as condensing media for CO2-CC, reheating and superheating upstream of the turbines and generators of the Ancillary Power Supply 11. The oxygen stream 12 downstream of the oxygen turbine section 12 serves for primary and the reheating Direct Steam generation in 16. The hydrogen for the HP/IP/LP Direct Steam torches can come either from the HPLTE-SG 13 after CO-water shift and CO2-CC (not depicted in FIG. 10) or more preferably from the gasification island after CO water shift, CO2-CC via lines 22 and unit 23, where the separated carbon dioxide 24 can be routed to the Main $CO_2$ Condenser in the section 2. It is from economics perspective and level of the purity more advantageous to supply the syngas of the HPLTE-SG 28 to an adjacent plant for manufacturing of the high end final products like gasoline, methanol, ethanol, fertilizer, SNG and other final products.

In case the operation pressure of the HP Direct Steam would be higher than the pressure level of the hydrogen from HP Gasification Island and the sections 2 and 23, this hydrogen stream shall undergo a compression 25. If there is a hydrogen stream from lower pressure levels (like presented in FIG. 6), this hydrogen stream shall undergo also the hydrogen compression 25. The hydrogen lines 13 and 27 supply along the oxygen line 12 and injection water 14 and 15 the section 16 for Direct Steam generation, Steam turbine and generator with the export electricity 17 to the grid from the Second Thermodynamic Cycle of the present invention (boundary limit III).

| FIG. 10 |
|---|
| Title: Embodiment of the invention for Super-Efficient hydrogen-based fossil power generation associated with the pre-combustion carbon capture and reuse of carbon dioxide (FIGS. 1, 3, 4A, 4B, 5A and 5B) from HP gasification |

| | |
|---|---|
| I | Boundary line of present invention in the embodiment for reuse of $CO_2$ from partial oxidization process i.e. gasification of coal, oil, NG and other hydrocarbons |
| II | Boundary line of the present invention associated with the First Thermodynamic Cycle via FIG. 4A with the elements 7, 8, 9, 19, 20, 21, 22, 23, 24 with the peculiar connections to oxygen and syngas hear recovery via FIGS. 5A and 5B |
| III | Boundary line of the present invention associated with the Second Thermodynamic Cycle, HPLTE-SG, interlinked with peculiar connections to the oxygen and syngas hear recovery via FIGS. 4B, 5A and 5B. |

Elements of the FIG. 10

| | |
|---|---|
| 1 | High pressure syngas from HP gasification |
| 2 | Syngas cooling and $CO_2$ condensation via CO2-CC with regenerative CO2-HR |
| 3 | Anhydrous $CO_2$ high pressure pump |
| 4 | Anhydrous $CO_2$ for reuse |
| 5 | Electrochemical $CO_2$ conversion with water with the HPLTE-SG, the High Pressure Low Temperature Electrochemical Syngas Generator |
| 6 | Purified water |

-continued

| FIG. 10 |
|---|

| | |
|---|---|
| 7 | High pressure water pump |
| 8 | HP purified feed water to the HPLTE-SG |
| 9 | Anodic oxygen product at HP/IP/LP pressure for ancillary heat recovery, preheating, super heating, oxygen turbine-generator set, and condensation media for the CO2-CC, excess oxygen for intern purposes e.g. oxy-fueling, oxygen supply to gasifier or to dispatch e.g. by bottling and shipment |
| 10 | Cathode products, the chemically pure syngas $CO/2H_2$ at HP/IP/LP pressure for ancillary heat recovery, preheating, superheating, syngas turbine-generator set, and condensation media for the CO2-CC and for HP/IP/LP Direct Steam generation via Direct Steam torches |
| 11 | Ancillary Power Supply with heat recovery, preheating, oxygen-syngas purifications, HP/IP CO converters, condensation media in CO2-CC section, $CO_2$ separation, recycle of anhydrous $CO_2$ for reuse and the sets of syngas and oxygen turbine-generator machineries with recovery heat exchangers, as well as the AC/DC convertor for HPLTE-SG's backup power |
| 12 | High pressure anode pure oxygen for HP/IP/LP oxygen supply to the HP/IP/LP Direct Steam torches |
| 13 | HP/IP cathodic syngas post HP-purification, HP/IP HT/LT CO converters, HP/IP CO2-CC units for $CO_2$ separation and recycling of the anhydrous $CO_2$ back to the $CO_2$ streams, main hydrogen stream for the HP/IP/LP Direct Steam torches. |
| 14 | HP/IP/LP purified water for Direct Steam torches |
| 15 | HP/IP/LP preheaters, jacket cooling of the Direct Steam torches prior to the injections for desuperheating of HP/IP/LP Direct Steams |
| 16 | HP/IP/LP Direct Steam generators, superheating, reheating, re-superheating sections with the set of steam turbines and generator |
| 17 | Export electricity to power grid |
| 18 | Anhydrous $CO_2$ for CO2-HR and CO2-PG |
| 19 | $CO_2$ waste heat and process heat recovery system CO2-HR |
| 20 | $CO_2$ turbines and generator CO2-PG for power generation, either for backup to the HPLTE-SG or export of AC current to the grid |
| 21 | Additional Electricity for power grid |
| 22 | HP gasification's syngas $H_2$/CO stream |
| 23 | HT/LT CO Water Shift converters, $CO_2$ capture and $CO_2$ separation at HP-gasification pressure margin |
| 24 | Recycle $CO_2$ to CO2-CC for the First Thermodynamic Cycle |
| 25 | Hydrogen compression for resupply of HP hydrogen stream |
| 26 | Hydrogen from MP/LP gasification and other side streams |
| 27 | HP/IP/LP hydrogen streams to HP/IP/LP Direct Steam torches |
| 28 | Chemically pure cathode syngas $CO/2H_2$ for number of final products e.g. gasoline, SNG, ethanol, methanol, kerosene, fertilizer, Fine Chemicals |

Appendix D: List of the abbreviations, acronyms, special expressions, and elements in the embodiments according to the FIGS. 1 to 10

Abbreviations

ACU

Auxiliary Cooling Unit employed to perform the condensation of residual carbon dioxide from the CO2-Stream downstream of CO2-CC. The ACU may run on hot season on occasion or run continuously in warm regions.

Ancillary CO2-HR

Any process integrated source of thermal energy from the process, which can be integrated in the First Thermodynamic Cycle, most importantly, the currently wasted thermal energy that is dissipated to the atmosphere through the cooling tower and flue gas of the power plants and chemical plants Auxiliary CO2-HR Any external heat recovery, re-superheating plant unit that performs the indirect super-heating and supraheating of carbon dioxide in the First Thermodynamic Cycle in the zone 4-5-6 of the FIG. 4A. The auxiliary CO2-HR is an external furnace operated by combustion of natural gas with oxygen or by a high-pressure gasification of natural gas, steam, and oxygen, wherein the oxygen is preferably obtained from the HPLTE-SG.

AC/DC Alternative current/Direct current
AC Generator Alternative Current generator, typically driven by turbines
AC/DC Converter Converter for conversion of alternative current to direct current
CO2-CC Cooling and condensation sections for $CO_2$. The CO2-CC includes the peculiarity of the First Thermodynamic Cycle, wherein the high pressure, low temperature anodic oxygen and high pressure, low temperature cathodic syngas from the HPLTE-SG are employed by the operation of multi-stage oxygen and syngas turbines with reheater sections according to the thermodynamic charts illustrated in the FIGS. 5A and 5B
CO2-HR Heat recovery sections employed for the First Thermodynamic Cycle, wherein the working media $CO_2$ is utilized according to the thermodynamic chart illustrated in the FIG. 4A
CO2-PG Power generation according to the First Thermodynamic Cycle, both utilized with $CO_2$ as working media for the driving compressor(s) or generator according to the thermodynamic chart illustrated in the FIG. 4A
CO2-Stream $CO_2$ containing gas, e.g. flue gas of fossil power plants or any other Stationary Source of carbon dioxide emission (vide definition for Stationary Sources of $CO_2$ emission)
CO2-Utilization Utilization of $CO_2$ as working media in general, like in CO2-HR and CO2-PG, including the integration of $CO_2$ economizer in the zone 1-2-3-7, in the thermodynamic chart of the First Thermodynamic Cycle in the FIG. 4A and the regenerative heat ex-changer(s) in the zones 3-4-6-7, and specifically the preheating and evaporation of the liquefied $CO_2$
CCC-HR Closed Cooling Circuit-Heat Recovery for the recovery of medium and low temperature thermal energy e.g. from the flue gas heat recovery, which employs a circulation of a heat carrier like conditioned water in a closed loop between the sources of medium and low temperature thermal energy at one end and recovery of that thermal energy into the working $CO_2$ media of the First Thermodynamic Cycle
Direct Steam High pressure, intermediary or low-pressure steam generated by direct combustion of hydrogen and oxygen i.e. via torches
Direct Steam torches
  The Direct Steam torches are presented in this process comprises two kind of special torches as inherent device part o the process, these are:
  (a) The primary high-pressure high temperature steam generated from the direct combustion of hydrogen and oxygen (obtained from the HPLTE-SG section) up stream of the HP section of the steam turbine.
  (b) Direct Steam torch for re-superheating of steam up stream of the IP and LP sections of the steam turbine.
  The Direct Steam torches according to the present process operates by hydrogen preferably from a high pressure gasification of coal, crude oil, natural gas, and the oxygen obtained from the HPLTE-SG supplant the huge section of HRSG (Heat Recovery Steam Generation) section of present power plants
EOR/IOR/CCS All these three acronyms present the application of captured carbon dioxide and sequestration of the captured carbon in underground locations, hence:
  EOR for Enhanced Oil Recovery by sequestration of captured carbon into the depleted oil fields, wherein a recovery of the crude oil can be carried out because of the inherent increase of the pressure level
  IOR refers to Improved Oil Recovery for sequestration of carbon in the oil fields which tends to deplete or require higher well output, CCS stands doe Carbon Capture and Sequestration of carbon in naturally hallow underground structures
Heat Exchange The generic term for heat exchange in the sense of the present process for the First Thermodynamic Cycle, HPLTE-SG and the Second Thermodynamic Cycle and encompasses distinctively the direct and the indirect heat transfer, whereas the direct heat exchange is specified by:
  (i) injection of liquid carbon dioxide into the superheated carbon dioxide stream in the First Thermodynamic Cycle upstream of for cooling purpose;
  (ii) injection of liquid carbon dioxide into the superheated carbon dioxide cycle upstream of the reheat section(s);
  (iii) injection of water into the generated Direct Steam by combustion of hydrogen and oxygen to delimit the rise of very high temperature;
  (iv) injection of saturated steam for the jacket cooling of the Direct Steam torches;
  (v) resuperheating of the steam downstream of each steam turbine section(s) for the purpose of reheating by use of hydrogen-oxygen combustion via Direct Steam torch (es);
as well as the heat transfer by indirect heat exchange which is carried out by the heat exchanger(s) with the following specific features in the following distinctive purposes;
  (vi) shell-and-tube heat exchangers i.e. with smooth tubes; with structured tubes; with bi-metall compound tubes; with ripped tubes; with fin tubes, which are used in the three fields of the present processes to execute the heat transfer between the various process intern media, i.e. in the First Thermodynamic Cycle, in the process and design of the HPLTE-SG and the Second Thermodynamic Cycle
  (vii) heat pipe heat exchanger(s) are employed in the three fields of the present processes to execute the heat transfer between the various process intern media, i.e. in the First Thermodynamic Cycle, in the process and design of the HPLTE-SG and the second thermodynamic cycle, and/or
  (viii) and/or to execute the heat transfer between the various process intern media with process external media, i.e. air cooler(s) and/or air-hybrid cooler(s) for the $CO_2$ condensation of the First Thermodynamic Cycle or for the Direct Steam condensation in the Second Thermodynamic Cycle
  (ix) as well as indirect heat transfer that is carried out specifically for $CO_2$ condensation of the carbon dioxide, both in the First Thermodynamic Cycle and also for the condensation of the carbon dioxide out of the Flue Gas by the evapuration cooling of carbon dioxide as cooling agent, recompression of the evapuraated carbon dioxide and it's recycle (freffered to as ACU, Auxiliary Cooling Unit)
HPLTE-SG High Pressure, Low Temperature Electrochemical Syngas Generator by electrochemical conversion of high pressure electrolyte i.e. the liquefied $CO_2$ and water
HP High pressure, e.g. high pressure oxygen, syngas, steam, $CO_2$, water and liquefied $CO_2$
HRSG Heat Recovery Steam Generation facility, commonly constructed in the fossil power plants as well as some other plants e.g. in ammonia, methanol plants or the Recovery Boiler of pulp and paper industry
LOX/GOX Liquid oxygen, gaseous oxygen
Liq. $CO_2$/Export Liq-$CO_2$ Liquefied carbon dioxide obtained by thee present processing via operation of the (i) First Thermodynamic Cycle; (ii)CO2-HR; (ii)CO2-CC; (iii)CO2-PG from the Stationary Sources of $CO_2$ emission, which then can be utilized for electrolysis with water to oxygen and syngas; be export to other sites as a new energy career; be applied for the production of ammonia, urea, and hydrocarbons i.e. jet fuel, gasoline, methanol, dimethylether and ethanol.

LP Low pressure

MP/IP Medium or intermediary pressure

Oxy-fueling The oxy-fueling according to the present process implies the addition of oxygen into the combustion air in order to reduce the amount of the intake combustion air. According to the present process invention, the oxygen for the oxy-fueling stems from the anodic stream of HPLTE-SG. The paramount advantage of this oxy-fueling results to much lower $CO_2$ containing flue gas, which in turn reduces the processing efforts of $CO_2$ capture and condensation, i.e. noticeable less number of flue gas compressors, size of the compressors, and sizes of the flue gas cleaning section as well as CO2-HR and CO2-CC sections Acronyms and Special Expressions Pre-Combustion $CO_2$ Capture According to the prevailing usage in clean energy, the pre-combustion capture of $CO_2$ comprises the $CO_2$ separation of $CO_2$ containing process gases before the process gas is processed in the processing of the chemical plants (e.g. gas turbines operated with syngas or ammonia plants). The processing for pre-combustion capture of $CO_2$ encompasses mostly the separation of $CO_2$ obtained from the LP/IP/HP gasification of coal, crude oil, petcoke, biomass and another carbonaceous feedstock.

Post-Combustion $CO_2$ Capture

The post-combustion separation of $CO_2$ comprises the capture of utmost greatest sources of the $CO_2$ emission culprit for the global Green House crisis, e.g. the fossil power plants, chemical plants, pulp and paper, cement industry, aluminum, and steel manufacturing. This group of the plants, commonly termed as the Stationary Sources of $CO_2$ emission, encompass nearly 75% of all global sources for the $CO_2$ emission (vide Stationary Source of $CO_2$ emission).

Reuse of $CO_2$ Net-Zero-Carbon Emission, and the Carbon Neutral Cycle in the Advanced Fossil Energy The Advanced Fossil Energy (or occasionally termed as carbon-neutral-cycle) implies those technologies, which are capable to perform net-zero-carbon-emission. All these technologies operate with the $CO_2$ capture, and conversion of the captured $CO_2$ to high value final products like jet fuel, gasoline, hydrocarbons etc. These technologies are commonly including the reuse of the captured $CO_2$ as a new fossil energy resource. The reuse of the carbon dioxide can resolve the global warming at one perspective, while from the other perspective it reduces the need for the primary fossil energy resource i.e. the need for crude oil and natural gas.

Nearly all Advanced Fossil Energy technologies in the present day running fossil energy plants, which are on operation currently with coal, crude oil, natural gas, and biomass are capable to turn these plants to Zero $CO_2$ emission and Zero pollution plants.

Because of the high yield in $CO_2$, the Advanced Fossil Energy processes favor the reuse of the captured carbon dioxide preferably with high rank coal, followed by low rank coal ahead of crude oil, natural gas, and biomass. Hence, only the Advanced Fossil Energy technologies can resolve the global warming. From economic perspective, only the Advanced Fossil Energy can also forge ahead due to the capability in commercially profitable solution that leads to lowering the costs for power and chemical production.

Stationary Sources of $CO_2$ Emission

A stationary point source of $CO_2$ is any source that is a single localized emitter, such as fossil fuel power plants, oil refineries, industrial process plants and other heavy industrial sources.

$CO_2$ from the Stationary Sources of $CO_2$ emission comprises typically the $CO_2$ from the fossil power plants, fuels or minerals, natural gas sweetening, cement production, refineries, iron and steel manufacturing, aluminum manufacturing, pulp and paper, other petrochemical productions like ammonia, methanol, hydrogen, ethylene and other hydrocarbon productions.

CLAIMS

Vide separate sheets enclosed

ABSTRACT OF THE DISCLOSURE

Vide separate sheet enclosed

SEQUENCE LISTING

Not applicable. Some generic publications in the carbon capture, sustainable energy by reuse of captured carbon dioxide, electrochemical conversion of carbon dioxide with water to syngas and oxygen in the Advanced Fossil Energy can be viewed via:

[1] Journal of Organic Chemistry, Perspective, 74, 487-498, January 2009 Chemical recycling of carbon dioxide to methanol and dimethyl ether from Green House Gas to renewable, environmentally carbon neutral fuels and synthetic hydrocarbons.
By: George A. Olah, Alain Goeppert, and G. K. Surya Prakash Loker Hydrocarbon Research Institute and Department of Chemistry, university of Southern California, Los Angeles, Calif., U.S.A.

[2] Graves, C. R. in Recycling $CO_2$ into Sustainable Hydrocarbon Fuels: Electrolysis of $CO_2$ and $H_2O$. Columbia University (2010)

The invention claimed is:

1. A high pressure process for at least one of post-combustion and/or pre-combustion $CO_2$ capture from a $CO_2$-containing stream, wherein the general inventive concept of this invention is grounded upon the operation of the three principal features, as follows:

(I) first the present process utilizes the chemically pure $CO_2$ as working media for a first new thermodynamic cycle defined as liquid-gaseous subcritical-supercritical $CO_2$ power cycle that converts currently useless wasted energy of power and commodity chemical plants to useful power, wherein the $CO_2$ containing gas at a desired concentration (between 0.4 Vol % to 35 Vol % from the flue gases of fossil power plants and/or 75 Vol % to 99 Vol % from other plants) is taken, then concentrated and compressed to supercritical pressure and then is cooled below the $CO_2$ critical temperature 31.06 Deg C; thus the $CO_2$ is separated from the compressed $CO_2$ Stream by way of supercritical-subcritical condensation in order to obtain liquid $CO_2$ from that $CO_2$ Stream wherein the distinctive processing stages of the new super-critical $CO_2$ thermodynamic power cycle are defined via following thermodynamic steps:

Step-1: isentropic pressure elevation of liquid $CO_2$ by use of high-pressure pump;

Step-2 isobaric subcritical preheating of liquid $CO_2$ carried out below the critical point;

Step-3: isobaric vaporization and superheating of $CO_2$ from subcritical condition over the critical point to the supercritical region;

Step-4: further isobaric $CO_2$-HR (heat recovery) which accomplishes primarily the recovery of the waste heat first; by then re-superheating of that $CO_2$ by use of any process heat utilization;

Step-5: isentropic expansion of supercritical supra-heated $CO_2$ by a backpressure expander $CO_2$ turbine in the $CO_2$-PG section which encompasses the power for driving compressor(s) and generator(s) wherein the latter AC power can be converted to DC power for backing up the HPLTE-SG electrolysis;

Step-6: isobaric regenerative heat exchange and the condensation of $CO_2$ from superheated supercritical $CO_2$ by using an ACU (Auxiliary Cooling Unit with coolant), refrigerants or partial expansion of liquid carbon dioxide to lower pressure and temperature in order to function liquid carbon dioxide as condensing media;

Step-7: isobaric undercooling of liquid $CO_2$ after the condensation and return of the undercooled liquid $CO_2$ back to the Step-1 thus the closing of the cycle is performed and then followed by:

(II) wherein then the obtained liquid $CO_2$ from that said concentrated $CO_2$-Stream is further processed via blending and cooling the liquid $CO_2$ with the purified water in order to prepare an electrolyte at high pressure and low temperature between the sublimation pressure of 5.5 bar and 1000 bar and 5° C. to 1000° C. and by then feeding to a High Pressure Low Temperature Electrochemical Syngas Generator (HPLT-SG); wherein the electrochemical dissociation of that electrolyte is carried out under the same pressure and temperature to an anodic oxygen stream and a cathodic syngas stream ($CO/2H_2$) whereas either of the two product streams (that is cathodic syngas in $2H_2/CO$ ratio and oxygen) are integrated in the subpart (I) as condensing media for the supercritical-subcritical $CO_2$ of the first new thermodynamic cycle repeatedly typically three to eight times over syngas and oxygen turbine;

(III) super-efficient hydrogen based fossil power generation with an overall efficiency of 90% to 95% is then attained by operation of a new second thermodynamic cycle wherein the cathodic pure hydrogen from a high pressure gasification is combusted with the anodic oxygen at various pressures; between 0.01 bar and 1000 bar operation pressure and up to 1000° C. via torches wherein the thermodynamic steps of the second new thermodynamic cycle are as follows:

Step-1: sequential combustion of high-pressure hydrogen with oxygen or oxygen/steam blends whereas that high pressure hydrogen is performed from a syngas which is obtained first by a gasification carried out at least above 73.84 bar yet typically at 300 bar and/or the syngas stems from an IP/LP Gasification Plant Island that operates below the 73.84 bar; then by the sequential combustion for Direct Steam generation is performed by special hydrogen-oxygen torches for generation of high temperature steam at a point 2' prevailing in the flame's tong of the torch along the isobaric trajectory defined by the routing left of the critical point of water and above the critical isobaric of the water;

Step-2: injection of temperature controlled water from point 1 and de-superheating of the flame steam and in situ generation of additional Direct Steam whereas the point 2 is attained close upstream of the HP section of the turbine;

Steps-3-8: sequential release of Direct Steam through the typical arrangement of HP/IP/LP (high pressure/intermediary pressure/low pressure) section of the steam turbine with individual reheating section which is carried out by further hydrogen-oxygen combustion;

Step-9: a final isentropic expansion step down in the last stage as LP (low pressure) Direct Steam upstream of the LP section of a turbine;

Step-10: partial or, optionally, total condensation of Direct Steam condensate and reuse of the water for further purpose whereby the undercooled steam condensate is further preheated prior to injection.

2. A process for $CO_2$ separation from post-combustion and/or pre-combustion, according to claim 1, by way of condensation of the $CO_2$ from that said $CO_2$-Stream is carried out first by compression above the critical point of CO then processed by way of supercritical cooling of $CO_2$-Stream via gas cooler heat exchanger(s) whereas downstream of that gas cooler a $CO_2$-free gaseous media is obtained and then the dehydration of $CO_2$-Stream is carried out with consequential $CO_2$ subcritical cooling of that $CO_2$-Stream via second gas cooler heat exchanger(s) with downstream residue gases (also referred as $CO_2$ purge gas) whereby a partial supercritical-subcritical condensation of $CO_2$ takes first place before the total condensation of $CO_2$ from that said $CO_2$-stream is executed with the $CO_2$ main Condenser and the carbon dioxide captured in a liquid $CO_2$ collector and/or in a pressurized storage tank whereas the processing assembly of those two supercritical and subcritical heat exchangers then dehydration column then the Main Condenser by then liquid $CO_2$ collector and storage tank are referred to $CO_2$—CC (carbon dioxide capture and condensation) section of the process.

3. A process according to claim 2 wherein the sources of said $CO_2$-stream comprises—either pure CO; form and/or in a $CO_2$ containing gaseous media and/or $CO_2$-enriched high concentrated $CO_2$-Stream which is referred to the Stationary $CO_2$ source of emission wherein at least one of flue gas of fossil power plants and/or flue gas of primary steam reformer and/or ammonia and/or methanol and/or gasoline and/or diesel and/or SNG and/or cement and/or steel manufacturing and/or COs of incineration and/or COs removed from natural gas and/or $CO_2$ containing off gas of oil and gas refineries and/or $CO_2$ obtained from treatments from refined oil and/or oil fractions and/or coke preparation from coal for the steel manufacturing and/or aluminum manufacturing and/or pulp and paper process and/or geothermal resources and/or fermentation off gases and the ubiquitous $CO_2$ from the air.

4. The process according to claim 2 wherein the process comprises specifically the removal of $CO_2$ from the $CO_2$-Stream of MP/LP gasification processes of coal and/or biomass and/or natural gas and/or crude oil and/or waste carbonaceous material by shunting of an interim compression stage up to the margin of 74 bar and 500 bar for HP gasification process whereby the $CO_2$-Stream of row syngas downstream of syngas cleaning and $CO_2$ and $H_2S$ removal is processed upstream of the $CO_2$—CC in the margin of 74 bar to 500 bar.

5. The process according to claim 2, wherein the condensation of the $CO_2$ from that $CO_2$-Stream is carried out at an operation pressure from 5.5 bar and $-56°$ C. over the sublimation line of $CO_2$ in the range of subcritical pressure of 5.5 bar to supercritical pressure at 500 bar and $-55°$ C. and $31°$ C.

6. The process according to the claim 2, wherein the supercritical heat exchanger cools the $CO_2$-Stream in the margin of $0.1°$ C. to $20°$ C. close over the critical temperature of $CO_2$ with $CO_2$-free and/or $CO_2$-diluted purge gases downstream of the $CO_2$—CC section in counter flow whereby the water is removed by way of condensation out of that $CO_2$-Stream first.

7. The process according to claim 2 wherein the remaining water traces are dehydrated by way of adsorption such as via at least one of molecular sieves and/or Pillared Clays and/or organic and/or inorganic hygroscopic agents and/or silica gel in adsorber beds operating intermittently at a $CO_2$ supercritical temperature margin of $31.06°$ C. to $100°$ C. whereby the adsorption is either carried out under polytropic condition and/or isothermal condition with indirect cooling of adsorber.

8. The process according to claim 2 wherein the supercritical dehydrated $CO_2$-Stream is further cooled down by the subcritical gas cooling heat exchanger(s) wherein a partial condensation of $CO_2$ out of that $CO_2$-Stream takes place by cooling with $CO_2$-free and/or $CO_2$-diluted purge gas downstream of $CO_2$—CC section in counterflow is carried out.

9. The process according to claim 2 wherein the total condensation of $CO_2$ is accomplished by use of a Cooling Media and/or such as at least one of cooling water and/or air cooler and/or hybrid cooler and/or refrigerant cooling and/or Freon and/or ammonia absorption cooling and/or thermoelectric generator heat exchanger and/or internal liquid and/or gaseous low temperature process media that is/are the gaseous products of HPLTE-Syngas Generator yet more preferably by an Auxiliary Cooling Unit (ACU) or any combination of them in the Main Condenser.

10. The process according to claim 2 wherein the ACU is performed by expansion of part of the obtained HP liquid $CO_2$ down to lower pressure in the margin from the critical temperature and pressure of 73.8 bar and $31.06°$ C. and above the sublimation line of $CO_2$ at 5.6 bar and at $-55.6°$ C. whereby the released ACU's $CO_2$ will be recompressed and cooled with $CO_2$-HR and/or Closed Cooling Cycle for Heat Recovery unit (in the CCC-HR section).

11. A process for liquid $CO_2$-supercritical $CO_2$ power cycle, according to claim 1, wherein heat recovery power generation with a pure $CO_2$ as working media of this power cycle is carried out with a or a number of liquid $CO_2$ pump(s) for pressure elevation of cycle's liquid $CO_2$ before the vaporization and supercritical superheating of power cycle's $CO_2$ ($CO_2$ re-gasifying) takes place by recuperation from any kind of waste heat sources with/without consecutive supraheating of power cycle's $CO_2$ by heating the superheated $CO_2$ via any process heat whereby the superheated/supraheated power cycle's $CO_2$ is directed to a set of expander turbines which will be driving generator(s) and/or other craft machines that is a or number of $CO_2$-Stream compressor(s) and/or will be driving $CO_2$ pump(s) is carried out for that liquid $CO_2$ obtained from the $CO_2$-Stream and/or liquid $CO_2$ pump of the power cycle.

12. The process according to claim 11 wherein the pressurization of liquid $CO_2$ for the supercritical $CO_2$ power cycle is carried out by pumping in single and/or in number of stages under simultaneous cooling below the critical temperature in the margin of $10°$ C. to $25°$ C. and at an outlet pressure of 5.6 bar to 1000 bar.

13. The process according to claim 11 wherein the preheating of liquid $CO_2$ and vaporization of liquid $CO_2$ as well as the superheating of $CO_2$ in the supercritical $CO_2$ power cycle is carried out in the margin of $30°$ C. to $1000°$ C. and working pressure of 5.6 bar to 1000 bar comprising the use of waste heat upstream of $CO_2$-Stream and all other waste heat resources such as at least one of residual LP off steam heat downstream of backpressure and/or condensation steam turbine(s) in all the fossil as well as nuclear power plants and/or the waste heat downstream of the supercritical $CO_2$ backpressure expander and/or pressure release expander turbine(s) and/or the waste heat of reflux steam condensate and/or flue gas heat prior to the chimney of fossil power plants with coal and/or petcoke and/or biomass and/or crude oil and/or refined oil fractions and/or flue gas stack of single cycle and/or combined cycle gas turbine power plants and/or $CO_2$ and waste heat of flue gas of steam reformer(s) and/or cracking furnaces and/or heat recovery of jacket cooling of reactors and/or the jacket and internal device cooling of equipment and/or intercooler(s) of compressors.

14. The process according to claim 11, wherein the waste heat recovery for $CO_2$ re-gasifying and superheating in the supercritical $CO_2$ power cycle is performed via heat exchangers directly coupled with the captured $CO_2$ stream and/or indirectly via one or a number of centralized Closed Cooling Circuits with a heat carrier wherein preferably on operation with conditioned water as heat carrier wherein the vaporization and superheating of the power cycle's $CO_2$ is carried out in the margin of $31.06°$ C. to $1000°$ C.

15. The process according to claim 11 for the power cycle wherein the sources for supraheating of $CO_2$ in the margin of $200°$ C. to $1000°$ and working pressure of 5.6 bar to 1000 bar takes place with the process heat sources such as at least one of combustion chamber of conventional fired power plants and/or gas turbine power plants and/or recovery boiler and bark boiler of pulp and paper manufacturing and/or process heat recovery of chemical processes that is CO water shift converter and/or ammonia and methanol synthesis section and/or absorption heat of absorber towers and/or solution heat of HP carbon dioxide with water (upstream of HPLTE-Syngas Generator) and/or Hot Syngas Gas cooler of gasifier and/or supraheating of $CO_2$ that is via indirect natural gas fired furnace (that is in the start-up furnace of ammonia/methanol plants) and/or natural gas gasification and/or H2/O2 sequential combustion (that is associated with super-efficient hydrogen based fossil power generation).

16. The process according to claim 11 wherein the power generation of superheated and/or supraheated carbon dioxide is carried out via a set of backpressure expander turbines consisting of HP/MP/LP stages each with/or without re-superheating of $CO_2$ takes place and whereby the set of the expander turbines drive(s) the generator and/or the ACU's $CO_2$; recycle compressor and/or for the Flue Gas compressor driven by the new first thermodynamic cycle.

17. The process according to claim 11 characterized that the inlet pressure to HP $CO_2$ expander turbine operates between 5.6 bar and 1000 bar and a temperature margin of $32°$ C. to $1000°$ C.

18. The process for liquid $CO_2$-supercritical $CO_2$ power cycle according to claim 17, wherein the $CO_2$ stream downstream of HP supercritical $CO_2$ expander turbine section of the power cycle will be returned back to the $CO_2$—CC for CO2-HR and reliquefication in $CO_2$—CC in pursuant to semi-closed liquid-gas $CO_2$ power cycle while the other part of $CO_2$ is then directed to MP $CO_2$ expander turbine section—with and/or without re-superheating—so the MP $CO_2$; stream is performed for heat recovery and temperature control with $CO_2$ de-superheating ready for sequestration and/or EOR and/or IOR (Improved Oil Recovery) in an open and/or semi-closed new first thermodynamic cycle for other MP applications.

19. The process according to claim 18 wherein the excess $CO_2$ is exported in liquid aggregate of state from $CO_2$ HP-pump for liquid CO: applications that is for the urea manufacturing and/or HPLTE-Syngas Generator.

20. The process according to claim 1, wherein for at least one of carbon capture from $CO_2$-Stream wherein the obtained liquid $CO_2$ and/or the excess liquid $CO_2$ from that said $CO_2$-Stream is pressurized by pump(s) to higher pressure and blended with high pressurized purified water under simultaneous $CO_2$ subcritical cooling in multiple mixing/cooling stages and fed to a high pressure low temperature electrochemical reactor (referred to HPLTE-Syngas Generator) that delivers cathodic syngas 2H2/CO and anodic oxygen 3/2 $O_2$ in a way that either of HPLTE-SG product streams can be used for various other applications.

21. The process according to claim 20 wherein the applications of the cathodic $2H_2$/CO intermediate product will comprise specifically $2H_2$/CO for methanol and/or after ratio conditioning with water-gas shift converter for ethanol and/or SNG and/or gasoline and/or kerosene and other transportation fuels as well as methanol and/or DME dimethyl ether and/or aviation fuel in every grade and any other hydrocarbons.

22. The process according to claim 20 wherein the applications of the cathodic intermediate product $2H_2$/CO encompass the conversion of syngas with steam/water via catalytic CO water shift converter to $3H2/CO_2$ stream whereby the pure HP/MP/LP hydrogen is obtained after the $CO_2$ separation by $CO_2$—CC wherein the HP/MP/LP hydrogen is supplied for chemicals that is for the ammonia synthesis and/or hydrogenation of middle and/or heavy hydrocarbons to light fraction hydrocarbons for the purpose of automotive fuels and/or gasoline and/or diesel and/or kerosene.

23. The process according to claim 20 wherein the applications of cathodic intermediate product $2H_2$/CO of HPLTE-Syngas Generator comprises the conversion of syngas with steam/water via catalytic CO water shift converter of to $3H2/CO_2$ stream whereby the pure HP/MP/LP hydrogen is obtained after the CO separation by $CO_2$—CC wherein the HP/MP/LP hydrogen—either with or without other hydrogen streams obtained from HP/MP/LP gasification processes and/or steam reforming and/or dry reforming with $CH/CO_2$ is performed for super-efficient hydrogen based fossil power generation.

24. A process wherein an anodic HP/IP/LP oxygen from said HPLTE-SG is applied for oxygen supply for gasification process and/or oxy-fueling of conventional fossil power plant and/or oxy-fueling of gas turbine power plants and/or recovery boiler of pulp and paper and/or chemical plants that is for nitric acid plants and/or oxidation reactors and/or cracking furnaces and/or more advantageously for super-efficient hydrogen based power generation.

25. The process according to claim 20 wherein the operation pressure of HPLTE-Syngas Generator is carried out between the sublimation pressure of 5.5 bar and 1000 bar and 5° C. to 1000° C. preferably between 5° C. to 50°.

26. The process according to claim 20 wherein the HPLTE-Syngas Generator's gaseous products namely the $2H_2$/CO cathodic syngas and anodic 3/2 $O_2$ oxygen are either totally and/or partially preheated for and then directed to back pressure expander turbine(s) for generating of ancillary power—driving AC current generator—whereby the AC current is converted to DC supporting the electricity for the electrochemical conversion in general for the HPLTE-SG reactor.

27. The process according to claim 20 wherein the preheating of the HPLTE-Syngas Generator's gaseous products takes place repeatedly upstream of each stage of turbine section of the syngas and/or the oxygen back pressure turbine distinguished in the way that the preheating of HPLTE-Syngas Generator's gaseous products are interlinked with the new first thermodynamic cycle wherein the preheating of syngas and/or oxygen stream upstream of each turbine section is employed to cool and/or condensate the $CO_2$ from the $CO_2$-Stream.

28. The process according to claim 27 wherein the new first thermodynamic cycle for liquid $CO_2$-supercritical $CO_2$ power cycle employs regenerative heat exchanger(s) downstream of the supercritical-subcritical $CO_2$ expander turbine as a heating source for the preheating of vaporized and/or superheated $CO_2$ stream of the $CO_2$-PG power cycle and/or any gaseous stream more specifically oxygen and $2H2$/CO of HPLTE-Syngas Generator with/or without indirect steam generation with/or without utilization for chemical reactors with/or without reboiler of stripper towers and the Boiler Feed Water economizer.

29. The process according to the claim 28 wherein the preheating of the HPLTE-Syngas Generator's gaseous products takes place repeatedly upstream of each stage of turbine section of the syngas and/or the oxygen back pressure turbine which is carried out to perform the cooling and/or condensation of the supercritical and/or subcritical $CO_2$ from the $CO_2$ circulating process stream in the new first thermodynamic cycle and/or from the $CO_2$-containing syngas from the gasification and/or steam reforming and/or the Dry Reforming.

30. The process according to claim 27, wherein for at least one of carbon capture and utilization and power generation and chemical conversion via HPLTE-Syngas Generator whereby the HP/MP/LP generated $O_2$ streams and the $H_2$ stream obtained originally from the cathodic product—either with or without other hydrogen streams obtained from HP/MP/LP gasification processes and/or steam reforming and/or dry reforming with $CH_4/CO_2$ will be subject to sequential $2H2/O2$ combustion whereby Direct Steam stream(s) more specifically HP ultra-superheated Direct Steam is performed for the new second thermodynamic cycle.

31. The process according to the claim 30 wherein the sequential combustion $2H_2/O_2$ is carried out via sequential injection of hydrogen into the main oxygen stream and/or more preferably oxygen injection(s) takes place into the main hydrogen stream by use of $H_2/O_2$ torches.

32. The process according to the claim 30 wherein the generated HP Direct Steam and the heat via sequential HP/MP/LP combustion of $H_2/O_2$ is availed for preheating of any process intermediates more specifically for the preheating of the high pressure superheated and circulating $CO_2$ stream of the first new thermodynamic cycle upstream of the supercritical $CO_2$ cycle in the CO2-PG section.

33. The process according to the claim 30 wherein at least one part of the oxygen obtained from the HPLTE-Syngas Generator is taken for combustion with hydrogen obtained from a gasification process so the HP ultra-superheated Direct Steam is performed upstream of steam turbine while the other oxygen side streams are performed for at least one of oxygen streams such as LOX and/or GOX for gasification process and/or oxy-fueling and/or oxy-fueling in combustion processes for power generation (that is designated for the conventional fossil and/or gas turbine power plants) while at least one other part is prepared as LOX.

34. The process according to the claim 30 wherein the oxygen stream and the hydrogen stream (either from HPLTE-Syngas Generator or obtained from gasification process) is availed for supplementary firing in existing conventional power plant and/or HRSG section of gas turbine combined cycle plants.

35. A process for Direct Steam generation by way of sequential combustion of $H_2/O_2$ via torches wherein the torch is specially distinguished with an:
a) external jacket cooling integrated in the Closed Cooling Circuit;
b) internal indirect skirt cooling coils impinged via Boiling Feed Water of MP HRSG section referred to as closed-end jacket cooling;
c) injection of saturated steam into the skirt cooling section of the torch referred to as open-end jacket cooling;
d) injection of water dispersed into the flame path of torch;
e) and/or injection of water in the surrounding field of the flame for de-superheating of the Direct Steam flame by way of temperature controlled measurement so the Direct Steam HP ultra-superheated Direct Steam is formed.

36. The process according to claim 35 that the generation of Direct Steam by way of sequential $H_2/O_2$ torches particularly HP ultra-superheated Direct Steam with re-superheating stage(s) is claimed wherein the generated Direct Steam is reheated by above torches in one or more re-superheating stages which then drives MP/LP sections of a the steam turbine(s) that facilitates the new second thermodynamic cycle that is either executed in a semi-open cycle whereby the steam downstream of that said LP turbine section is released into the atmosphere or it is condensed for reuse in a closed cycle or a combination of the two latter embodiments.

37. The process, according to claim 10, wherein the entire heat recovery units ($CO_2$-HR and CCC-HR) with the set of $CO_2$ turbines ($CO_2$-PG) and with the HP Direct Steam generation in combination with its set of Direct Steam turbines with/without indirect steam generation in combination with the set of indirect steam turbines facilitates the new generation of super-efficient hydrogen based fossil power generation.

38. The process for at least one of carbon capture and liquefaction and utilization and chemical conversion according to the claim 37, wherein the entire heat and/or process recovery units ($CO_2$-HR and CCC-HR) with the set of $CO_2$ turbines ($CO_2$-PG) and regenerative heat exchanger(s) of the first thermodynamic cycle with the HP Direct Steam generation in combination with the set of Direct Steam turbines with/or without under-cooled Direct Steam condensate turbine with MP indirect steam generation in combination with the set of indirect steam back pressure turbines and/or indirect steam condensation turbine of the second thermodynamic cycle facilitates the new generation for super-efficient hydrogen based fossil power generation characterized with the overall gross plant efficiency in the margin of 60% to 99% more specifically in the margin of overall gross efficiency of 90% to 95% with effective carbon capture in margin of 60% to 100%, more specifically in margin of 90% to 100% in either case depending on seasonal and regional ambient conditions according to the claim 1 in CID).

39. The process for at least one of post-combustion carbon capture and liquefaction and utilization and chemical conversion and power generation, according to claim 11, wherein low and/or middle pressure subcritical $CO_2$ gaseous and other $CO_2$ pollution emitting sources are first subjected to scrubbing and/or cleaning with Flue Gas heat recovery and compression of Flue Gas over the supercritical pressure of $CO_2$ that is carried out in either single or multiple compression stage(s) with the associated intercooler/final gas cooler and heat recovery and dehydration of that said Flue Gas takes place before the compressed Flue Gas is treated in $CO_2$—CC for separation of liquid $CO_2$ out of the that Flue Gas wherein the $CO_2$-free Flue Gas (off gas) is eventually preheated and then released back into the atmosphere downstream of the off gas expander turbine(s).

40. The device according to claim 1, consisting of a high pressure low temperature electrochemical reactor (referred to as HPLTE-Syngas Generator) that comprises of two reaction chambers for cathodic (2 $H_2$/CO) syngas and anodic oxygen (3/2 $O_2$) production with gas lock and/or liquid lock and/or liquid-gas separation at the top and a diaphragm compartment that is concentric emplaced within the circulating cathodic liquid phase at one side while the anodic liquid phase is circulating at the other side of diaphragm whereby the very high circulation flow of each liquid phase is facilitated on the principals for Mammoth Pump by the evolved gaseous products in each reaction chamber while the migration of ions through the diaphragm in the liquid phase is intensified whereby the HPLTE-Syngas Generator is distinguished preferably with one or more of the peripheral equipment and sections with/without internal cooling coils to govern isothermal reaction condition according to.

41. The device according to the claim 40 the reactor is fed with a blend of liquid $CO_2$ and water so that either stream is pressurized by pumping under cooling at high pressure and cooled below the critical temperature of CO while the mixing and cooling of liquid $CO_2$-water blend is taking place simultaneously.

42. The device according to the claim 40 wherein the operation pressure of the HPLTE-SG reactor is in the margin of 5.5 bar to 1000 bar and the operation temperature in the margin of $-56.57°$ C. and $+31.06°$ C. more preferably in the range of 200 to 400 bar and temperature of $+5°$ to $25°$ C.

43. The device according to claim 40 wherein the pressurization of reactor precursors that is water and the liquid carbon dioxide is carried out in the margin of 5.5 bar (over the sublimation pressure of $CO_2$) and 1000 bar for the operation pressure of HPLTE-Syngas Generator according to the claim 42.

44. The device according to the claim 40 wherein the cooling of reactor precursors that is water and liquid $CO_2$ is carried out while their pressurizing and mixing is performed in the margin of $-56.57°$ C. (sublimation temperature of $CO_2$) and $+31.06°$ C. the critical temperature of $CO_2$.

45. The device according to the claim 40 wherein the blending under subcritical temperature of $CO_2$ is carried out by multiple injection stages of liquid $CO_2$ into the water and/or $CO_2$-water blend under simultaneous mixing and cooling in every injection stage so an aqueous solution of $CO_2$ in water in particular high concentrated electrolyte yet more preferably $CO_2$ saturated aqueous undercooled solution of $CO_2$ is obtained at any ratio up to the stochiometric ration of $CO_2$/H2O of 1:2.

46. The device according to the claim 40 wherein the feedstocks of HPLTE-Syngas Generator is fed into the reactor either by one blend stream of $CO_2$—$H_2O$ wherein the leveling of mass flow rates of both chambers is carried out by diaphragm and/or two separated streams of $CO_2$—$H_2O$ electrolyte into the anodic and cathodic reaction chamber individually in the bottom section of cathodic and anodic reaction chamber wherein the compensation of liquid level occurs through the diaphragm.

47. The device according to the claim 40 wherein the reactor is further distinguished by purification measures for each gaseous product.

48. The device according to the claim 40 wherein the removal of $O_2$ traces out of the cathodic syngas $2H_2/CO$ is either by molecular sieve on the basis of pressure swing adsorption (PSA) and/or absorption and/or chemisorption and/or non-catalytic chemical conversion and/or preferably by a trickle reactor and catalytic conversion of oxygen traces with accompanied hydrogen to water and/or more preferably by passing the cathodic gases through an electric arc momentarily wherein the reaction of oxygen traces with the concomitant hydrogen is performed immediately upstream of water absorber for $CO_2$ removal.

49. The device according to the claim 40 wherein the removal of $CO_2$ traces out of the cathodic 2H2/CO takes place in a separate absorber via water and/or more preferably with water in the same trickle reactor above.

50. The device according to claim 40 wherein the discharge of absorber preferably the above trickle reactor is carried out by way of flush pressure release and/or preferably by way of HP thermal desorption carried out with heater that is an electric heater whereas the desorber's off gas of syngas purification section is led to the off gas combustion along with the off gas downstream of anodic oxygen purification section for heat recovery.

51. The device according to claim 40 wherein the removal of H: traces out of the anodic oxygen stream downstream of the reactor is carried out by either molecular sieve on the basis of pressure swing adsorption (PSA) and/or absorption and/or chemisorption and/or non-catalytic chemical conversion and/or more preferably by passing the anodic gas through an electric arc wherein the conversion of hydrogen traces takes place momentarily that is carried out immediately upstream of $CO_2$ absorber for removal of $CO_2$ out of anodic oxygen stream.

52. The device according to claim 40 wherein the desorber off gas of the anodic oxygen purification section is led to off gas combustion along with the off gas downstream of cathodic syngas purification section for heat recovery.

53. The device according to the claim 40 wherein the high pressure anodic purified HP oxygen gas stream is preheated repeatedly via any heat sources from the prevailing operation temperature of HPLTE-Syngas Generator of +5° to in one and/or a multiple stage of heat exchanger(s) before it is fed to HP/IP/LP multi-stage oxygen backpressure expander turbine(s) repeatedly that drives an ancillary generator whereas oxygen upstream of the final stage of the oxygen turbine operates to a higher temperature in the margin of 500° C.

54. The device according to the claim 40 wherein the device invention of HPLTE-Syngas Generator comprises the HP/IP/LP multi-stage cathodic gas preheating repeatedly of +5° to −30° C. to in one and/or a multiple stage of heat exchanger(s) before it is fed to each HP/IP/LP multi-stage syngas and/or hydrogen backpressure expander turbine(s) that drives an ancillary generator whereas the final stage of syngas turbine operates to a higher temperature in the margin of 600° C.

55. The device according to claim 54 wherein the preheating stages of the gaseous products of HPLTE-Syngas Generator in upstream of each stage of back pressure turbine section is interconnected with the first thermodynamic cycle whereas these product gases are employed for the condensation of circulating $CO_2$ stream in the $CO_2$-PG downstream of the supercritical-subcritical $CO_2$ turbine and/or the regenerative heat exchangers of the $CO_2$ power cycle.

56. The device according to the claim 55 wherein the syngas heat downstream of back pressure expander is integrated as part of syngas preheating in order to accommodate the temperature level of syngas in the water gas shift reactor and/or by way of water injection into the syngas upstream of HP/MP water shift converter.

57. The device according to claim 55 wherein the device invention HPLTE-Syngas Generator encompasses the AC/DC converter for the conversion of gained ancillary AC current to DC current for backing up the power supply of HPLTE-Syngas Generator.

58. The process for high pressure low temperature electrochemical conversion of the electrolyte liquid carbon dioxide-water blend, according to claim 1, is backed up by supplementary DC power supply current gained by use of the solar power DC generation.

59. The process for high pressure low temperature electrochemical conversion of the electrolyte liquid carbon dioxide-water blend, according to claim 1, is backed up by supplementary supply of DC current gained by use of the fuel cells for DC back up line which is generated by the combustion of oxygen downstream of the oxygen turbine and the hydrogen downstream of the CO-water shift converters and CO removal either from the (i)HPLTE-SG cathodic product downstream of low pressure section of syngas and/or hydrogen turbine and/or from the (ii) from gasification.

\* \* \* \* \*